(12) United States Patent
Su

(10) Patent No.: US 9,388,164 B2
(45) Date of Patent: Jul. 12, 2016

(54) METHODS OF USING PYRUVATE KINASE ACTIVATORS

(75) Inventor: Shin-San M. Su, Newton, MA (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 133 days.

(21) Appl. No.: 14/115,290

(22) PCT Filed: May 3, 2012

(86) PCT No.: PCT/US2012/036406
§ 371 (c)(1),
(2), (4) Date: Feb. 14, 2014

(87) PCT Pub. No.: WO2012/151448
PCT Pub. Date: Nov. 8, 2012

(65) Prior Publication Data
US 2014/0155374 A1    Jun. 5, 2014

Related U.S. Application Data

(60) Provisional application No. 61/482,165, filed on May 3, 2011.

(51) Int. Cl.
| | | |
|---|---|---|
| *A61K 31/535* | (2006.01) | |
| *C07D 471/04* | (2006.01) | |
| *C07D 401/12* | (2006.01) | |
| *A61K 31/397* | (2006.01) | |
| *A61K 31/4427* | (2006.01) | |
| *A61K 31/4725* | (2006.01) | |
| *A01N 1/02* | (2006.01) | |
| *C07D 401/14* | (2006.01) | |

(52) U.S. Cl.
CPC ............ *C07D 401/12* (2013.01); *A01N 1/0226* (2013.01); *A61K 31/397* (2013.01); *A61K 31/4427* (2013.01); *A61K 31/4725* (2013.01); *C07D 401/14* (2013.01)

(58) Field of Classification Search
CPC ............................. A61K 31/535; C07D 471/04
USPC .............................. 514/234.2; 544/127, 234.2
See application file for complete search history.

(56) References Cited

U.S. PATENT DOCUMENTS

2014/0194402 A1    7/2014 Su

FOREIGN PATENT DOCUMENTS

| | | |
|---|---|---|
| JP | H07165708 A | 6/1995 |
| JP | 2008514590 A | 5/2008 |
| WO | 9948490 A1 | 9/1999 |
| WO | 0117956 A1 | 3/2001 |
| WO | 2006033628 A1 | 3/2006 |
| WO | 2010105243 A1 | 9/2010 |
| WO | 2010118063 A2 | 10/2010 |
| WO | 2010124082 A1 | 10/2010 |
| WO | 2011002817 A1 | 1/2011 |
| WO | 2012052102 A1 | 4/2012 |
| WO | 2012083246 A1 | 6/2012 |

OTHER PUBLICATIONS

Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.
Boxer, et al. "Evaluation of Substituted N,N'-Diarylsulfonamides as Activators of the Tumor Cell Specific M2 Isoform of Pyruvate Kinase" Journal of Medicinal Chemistry (2010) vol. 53, pp. 1048-1055.
European Search Report for European Application No. 11808773.3 dated Apr. 9, 2014.
International Search Report and Written Opinion for International Application No. PCT/US2012/036406 dated Jul. 6, 2012.
International Search Report and Written Opinion for International Application No. PCT/US2013/069193 dated Feb. 26,2014.
International Search Report dated Apr. 4, 2012 for related Application PCT/US2011/065633.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.

*Primary Examiner* — Raymond Henley, III
(74) *Attorney, Agent, or Firm* — Lando & Anastasi, LLP

(57) ABSTRACT

Described herein are methods for using compounds that activate pyruvate kinase.

25 Claims, No Drawings

METHODS OF USING PYRUVATE KINASE ACTIVATORS

CLAIM OF PRIORITY

This application is a national stage application under 35 U.S.C. §371 of International Application No. PCT/US2012/036406, filed May 3, 2012, and published as International Publication No. WO 2012/151448 on Nov. 8, 2012, which claims priority from U.S. Ser. No. 61/482,165, filed May 3, 2011. The contents of each of these applications which is incorporated herein by reference in its entirety.

BACKGROUND

Pyruvate kinase deficiency (PKD) is one of the most common enzyme defects in erythrocytes in human due to autosomal recessive mutations of the PKLR gene (Zanella, A., et al., *Br J Haematol* 2005, 130 (1), 11-25). It is also the most frequent enzyme mutation in the central glycolytic pathway and only second to glucose-6 phosphate dehydrogenase (G6PD) deficiency (Kedar, P., et al., *Clin Genet.* 2009, 75 (2), 157-62) of the hexose monophosphate shunt.

Human erythrocytes are unique in that they anucleate when mature. Immature erythrocytes have nuclei but during early erythropoiesis prior to becoming circulating reticulocytes they extrude nuclei as well as other organelles such as mitochondria, endoplasmic reticulum, and golgi apparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate $NAD^+$ through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic haemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}$>Met associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet.* 2009, 75 (2), 157-62; Fermo, E. et al., *Br J Haematol* 2005, 129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}$>Trp and $Arg^{510}$>Gln, while mutations $Arg^{479}$>His, $Arg^{490}$>Trp and $Asp^{331}$>Gly were more frequently found in Asian patients (Kedar, P., et al., *Clin Genet.* 2009, 75 (2), 157-62).

The present invention provides a method for increasing lifetime of the red blood cells (RBCs) in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention further provides a method for regulating 2,3-diphosphoglycerate levels in blood in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention also provides a method for treating hereditary non-spherocytic haemolytic anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating sickle cell anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

In one embodiment, provided is a compound of formula (I):

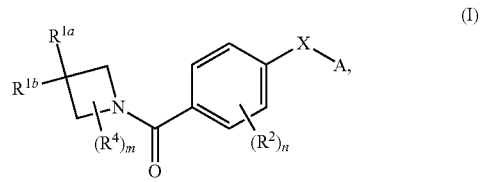

or a pharmaceutically acceptable salt thereof, wherein:
A is aryl or heteroaryl, wherein the aryl or heteroaryl is optionally substituted, and the aryl or heteroaryl is optionally fused to an optionally substituted carbocyclyl or an optionally substituted heterocyclyl;
X is selected from —NH—S(O)$_2$—, —N(alkyl)-S(O)$_2$—, —S(O)$_2$—N(H)—, and —S(O)$_2$—N(alkyl)-;

$R^{1a}$ is selected from hydrogen, alkyl, aryl, and arylalkyl; and $R^{1b}$ is selected from $OR^3$, $N(alkyl)R^3$ and $NHR^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, $C(O)R^a$, and $C(O)N(H)R^a$, wherein $R^a$ is selected from alkyl, alkenyl, aryl, heteroaryl, arylalkyl and heteroarylalkyl; and wherein any aryl or heteroaryl portion of $R^a$ is optionally substituted;

each $R^4$ is independently selected from haloalkyl, alkyl, alkoxy and hydroxyl n is 0, 1, or 2;

m is 0, 1, or 2.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl).

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkynyl" refers to a monovalent straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively.

The term "aralkylamino" refers to a —NH(aralkyl) radical.

The term "alkylaminoalkyl" refers to a (alkyl)NH-alkyl-radical.

The term "dialkylaminoalkyl" refers to a (alkyl)$_2$N-alkyl-radical.

The term "mercapto" refers to an —SH radical.

The term "thioalkoxy" refers to an —S-alkyl radical.

The term "thioaryloxy" refers to an —S-aryl radical.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems may be alternately characterized as being an aryl or a heteroaryl fused to a carbocyclyl or heterocyclyl, particularly in those instances where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

All ring systems (i.e, aryl, heteroaryl, carbocyclyl, cycloalkyl, heterocyclyl, etc.) or ring system portions of groups (e.g., the aryl portion of an aralkyl group) are optionally substituted at one or more substitutable carbon atoms with substituents independently selected from: halo, —C≡N, $C_1$-$C_4$ alkyl, =O, $C_3$-$C_7$ cycloalkyl, $C_1$-$C_4$ alkyl, —OH, —O—($C_1$-$C_4$ alkyl)-, —SH, —S—($C_1$-$C_4$ alkyl), —($C_1$-$C_4$ alkyl)-N($R^b$)($R^b$), —N($R^b$)($R^b$), —O—($C_1$-$C_4$alkyl)-N($R^b$)($R^b$), —($C_1$-$C_4$ alkyl)-O—($C_1$-$C_4$ alkyl)-N($R^b$)($R^b$), —C(O)—N($R^b$)($R^b$), —($C_1$-$C_4$ alkyl)-C(O)—N($R^b$)($R^b$), —O-(heteroaryl), —O-(heterocycle), —O-phenyl, -heteroaryl, -heterocycle, and -phenyl, wherein:

- each $R^b$ is independently selected from hydrogen, and —$C_1$-$C_4$ alkyl; or
- two $R^b$ are taken together with the nitrogen atom to which they are bound to form a 4- to 8-membered saturated heterocycle optionally comprising one additional heteroatom selected from N, S, S(=O), S(=O)$_2$, and O,
- any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$; and
- any carbon atom on a phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$;

All heterocyclyl ring systems (and any heterocyclyl substituents on any ring system) is optionally substituted on one or more any substitutable nitrogen atom with —$C_1$-$C_4$ alkyl, or fluoro-substituted $C_1$-$C_4$ alkyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

The term "activator" as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Compounds

Described herein are compounds and compositions that activate wild type PKR and/or various mutant PKRs such as those mutants described herein.

In one embodiment, provided is a compound of Formula I, wherein m is 0 (i.e., there are no $R^4$ substituents on the azetindinyl ring), the compound having Formula (Ia):

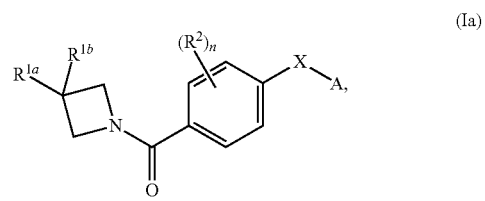

or a pharmaceutically acceptable salt thereof, wherein:

A is aryl or heteroaryl, wherein the aryl or heteroaryl is optionally substituted; and the aryl or heteroaryl is optionally fused to an optionally substituted carbocyclyl or an optionally substituted heterocyclyl;

X is selected from —N(H)—S(O)$_2$—, —N(alkyl)-S(O)$_2$—, —S(O)$_2$—N(alkyl)- and —S(O)$_2$—N(H)—;

$R^{1a}$ is selected from hydrogen, alkyl, aryl, and arylalkyl; and $R^{1b}$ is selected from OR$^3$, N(alkyl)R$^3$ and NHR$^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted; and n is 0, 1, or 2.

In certain aspects of the above embodiment, A is an optionally substituted bicyclic heteroaryl. In a more specific aspect, A is quinolin-8-yl and the compound has the structure set forth in formula (II), or a pharmaceutically acceptable salt thereof:

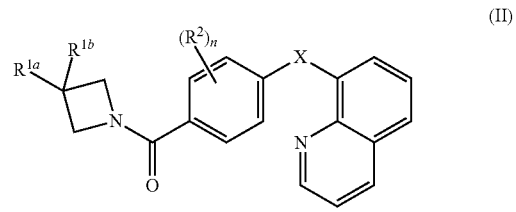

wherein:

$R^{1a}$, $R^{1b}$, $R^2$, $R^3$, X, and n are as defined for Formula Ia.

In certain embodiments of Formula I, Ia or II, $R^{1a}$ is hydrogen.

In certain embodiments of Formula I, Ia or II, $R^{1a}$ is optionally substituted phenyl.

In some embodiments of Formula I, Ia or II, $R^{1a}$ is alkyl. In one aspect of these embodiments, $R^{1a}$ is methyl.

In certain embodiments of Formula I, Ia or II, $R^{1a}$ is arylalkyl, wherein the aryl portion is optionally substituted. In one aspect of these embodiments, $R^{1a}$ is optionally substituted benzyl.

In some embodiments of Formula I, Ia or II, $R^{1b}$ is —OR$^3$. In one aspect of these embodiments, $R^{1b}$ is hydroxyl. In an alternate aspect $R^{1b}$ is —O-alkyl. In a more specific aspect, $R^{1b}$ is methoxy. In still another aspect $R^{1b}$ is optionally substituted phenoxy. In another aspect $R^{1b}$ is optionally substituted benzoxy. In another aspect $R^{1b}$ is optionally substituted —OC(O)-benzyl. In still another aspect, $R^{1b}$ is optionally substituted —OC(O)-pyridinyl. In another aspect, $R^{1b}$ is —OC(O)NH(alkyl). In a more specific aspect, $R^{1b}$ is —OC(O)NH(CH(CH$_3$)$_2$). In another aspect, $R^{1b}$ is optionally substituted —OC(O)NH(heteroaryl). In a more specific aspect, $R^{1b}$ is optionally substituted —OC(O)NH(pyridinyl).

In some embodiments of Formula I, Ia or II, $R^{1b}$ is $NHR^3$ or $N(alkyl)R^3$. In one aspect of these embodiments, $R^{1b}$ is $NHR^3$. In an alternate aspect $R^{1b}$ is $N(CH_3)R^3$. In another aspect of these embodiments $R^3$ is optionally substituted aryl. In a more specific aspect, $R^3$ is optionally substituted phenyl. In another aspect of these embodiments $R^3$ is optionally substituted aralkyl. In a more specific aspect, $R^3$ is optionally substituted benzyl. In another aspect of these embodiments $R^3$ is optionally substituted heteroaryl. In a more specific aspect, $R^3$ is optionally substituted pyridinyl. In another aspect of these embodiments $R^3$ is optionally substituted —C(O)-heteroaryl. In a more specific aspect, $R^3$ is optionally substituted —C(O)-pyridinyl. In another aspect of these embodiments $R^3$ is optionally substituted —C(O)—NH-heteroaryl. In a more specific aspect, $R^3$ is optionally substituted —C(O)—NH-pyridinyl. In still another aspect of these embodiments $R^3$ is —C(O)—NH-alkyl or —C(O)—NH-alkenyl. In a more specific aspect, $R^3$ is —C(O)—NH—CH(CH_3)_2$. In another more specific aspect, $R^3$ is —C(O)—NH—CH_2—CH=CH_2$.

In certain embodiments of Formula I, Ia or II, n is 0 or 1. In one aspect of an embodiment where n is 1, $R^2$ is selected from fluoro, methyl, and methoxy.

In certain embodiments of Formula I, Ia or II, X is —NH—S(O)_2 or —S(O)_2—NH.

In certain embodiments of Formula II, $R^{1a}$ is phenyl or benzyl, wherein the ring portion of $R^{1a}$ is optionally substituted; and is $R^{1b}$ is hydroxyl. In certain aspects of this embodiment n is 0 or 1; and $R^2$, when present, is selected from methyl, and methoxy. In other aspects of this embodiment, X is —NH—S(O)_2.

In some embodiments of Formula II, $R^{1a}$ is hydrogen, and $R^{1b}$ is selected from —NH-phenyl, phenoxy, —NH-pyridin-2-yl, —N(CH_3)-phenyl, wherein the phenyl or pyridinyl portion of $R^{1b}$ is optionally substituted. In certain aspects of this embodiment n is 0 or 1; and $R^2$, when present, is selected from methyl, and methoxy. In other aspects of this embodiment, the phenyl or pyridinyl portion of $R^{1b}$ is optionally substituted with methoxy.

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 8. Compounds described herein are also useful as activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

A compound described herein may be an activator of a PKR, for example, a wild type (wt) or mutated PKR (e.g., R510Q, R532W, OR T384W). Exemplary compounds are shown in Table 1. As shown in Table 1, A refers to a compound that has a % activation at 1 µM of from 1 to 100. B refers to an a compound that has a % activation at 1 µM of from 101 to 500. C refers a compound that has a % activation at 1 µM of >500.

In Table 1, a compound described herein may also have an AC50 of wild type PKR, PKR R532W, PKR T384W, PKR G332S, PKR G364D, PKR G37E and/or PKR R479H. AA refers to an AC50 less than 100 nM, BB refers to an AC50 from 101 nM to 500 nM and CC refers to an AC50 greater than 500 nM.

TABLE 1

| Structure | % Act. R510Q | % Act. R532W | % Act. T384W | Act. % WT | PKR WT AC50 (µM) |
|---|---|---|---|---|---|
| (phenoxy-azetidinyl-carbonyl-phenyl-sulfonamide-quinoline structure) | B | B | B | B | BB |

TABLE 1-continued

| Structure | | | | | |
|---|---|---|---|---|---|
| benzyl-hydroxy-azetidine-benzamide-quinoline sulfonamide | B | B | B | B | AA |
| pyridine-carboxylate-azetidine-benzamide-quinoline sulfonamide | B | A | B | B | |
| pyridine-carboxamide-azetidine-methylbenzamide-quinoline sulfonamide | B | A | B | B | BB |
| pyridine-carboxamide-azetidine-benzamide-quinoline sulfonamide | B | A | B | B | |
| benzyl-methoxy-azetidine-benzamide-quinoline sulfonamide | B | B | B | B | |
| phenoxy-azetidine-methylbenzamide-quinoline sulfonamide | B | A | A | A | AA |
| phenoxy-azetidine-fluorobenzamide-quinoline sulfonamide | B | B | B | B | |
| pyridylmethoxy-azetidine-benzamide-quinoline sulfonamide | B | B | B | B | BB |
| benzyl-methylamino-azetidine-methylbenzamide-quinoline sulfonamide | B | B | A | B | |

TABLE 1-continued

| Structure | | | | | |
|---|---|---|---|---|---|
| (pyridine-carbonyloxy-azetidine-methylphenyl-sulfonamide-quinoline) | B | A | A | A | |
| (pyridine-carboxamide-azetidine-phenyl-sulfonamide-quinoline) | B | B | B | B | CC |
| (phenylamino-azetidine-phenyl-sulfonamide-quinoline) | A | A | A | A | |
| (methoxyphenylamino-azetidine-phenyl-sulfonamide-quinoline) | B | A | A | A | |
| (methoxyphenylamino-azetidine-methylphenyl-sulfonamide-quinoline) | B | A | A | A | |
| (methoxyphenylamino-azetidine-fluorophenyl-sulfonamide-quinoline) | A | A | A | A | |
| (methoxyphenylamino-azetidine-phenylsulfonyl-quinolinylamine) | B | B | A | B | |
| (methoxyphenyl-N-methyl-azetidine-phenyl-sulfonamide-quinoline) | B | B | A | B | |
| (phenylamino-azetidine-fluorophenyl-sulfonamide-quinoline) | B | B | B | B | CC |

TABLE 1-continued
| Structure | | | | |
|---|---|---|---|---|
| 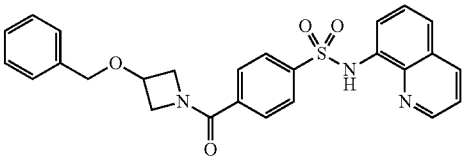 [SMILES: O=C(c1ccc(S(=O)(=O)Nc2cccc3cccnc23)cc1)N1CC(OCc2ccccc2)C1] | B | A | B | B |
| 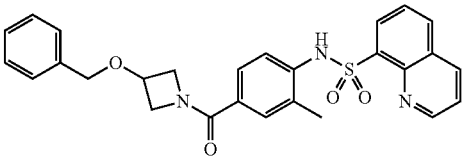 [SMILES: Cc1cc(C(=O)N2CC(OCc3ccccc3)C2)ccc1NS(=O)(=O)c1cccc2cccnc12] | B | A | B | B |
| 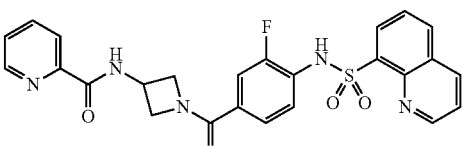 | B | A | B | B |
| 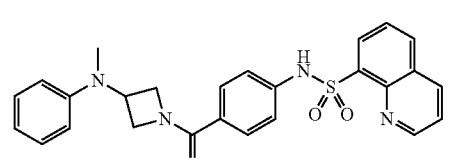 | B | B | B | B |
| 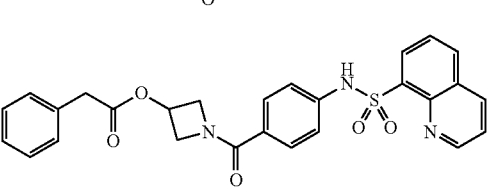 | B | A | B | B |
| 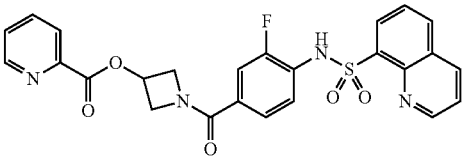 [SMILES: O=C(OC1CN(C(=O)c2ccc(NS(=O)(=O)c3cccc4cccnc34)c(F)c2)C1)c1ccccn1] | B | B | B | B |
| 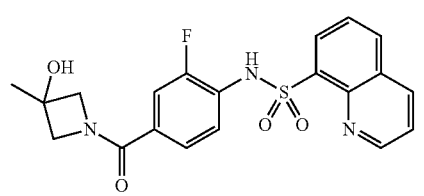 [SMILES: CC1(O)CN(C(=O)c2ccc(NS(=O)(=O)c3cccc4cccnc34)c(F)c2)C1] | B | A | B | B |
| 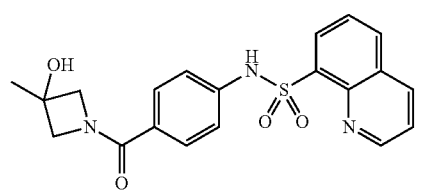 [SMILES: CC1(O)CN(C(=O)c2ccc(NS(=O)(=O)c3cccc4cccnc34)cc2)C1] | B | A | B | B |
| 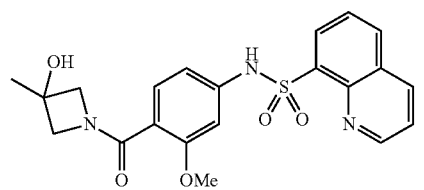 [SMILES: COc1cc(NS(=O)(=O)c2cccc3cccnc23)ccc1C(=O)N1CC(C)(O)C1] | B | A | B | B |

TABLE 1-continued

| Structure | | | | | |
|---|---|---|---|---|---|
| (2-methoxyphenyl-N-methyl-azetidinyl benzamide quinoline sulfonamide) | B | A | B | B | |
| (2-methoxyphenoxy-azetidinyl benzamide quinoline sulfonamide) | B | A | B | B | |
| (3-benzyl-3-hydroxy-azetidinyl 2-methoxy-benzamide quinoline sulfonamide) | B | B | B | B | |
| (3-benzyl-3-hydroxy-azetidinyl 3-methyl-benzamide quinoline sulfonamide) | B | A | B | B | |
| (isopropyl carbamate azetidinyl 3-methyl-benzamide quinoline sulfonamide) | B | B | A | B | |
| (isopropyl carbamate azetidinyl 2-methoxy-benzamide quinoline sulfonamide) | B | B | B | B | |
| (isopropyl carbamate azetidinyl 2-fluoro-benzamide quinoline sulfonamide) | B | A | B | B | |
| (isopropyl carbamate azetidinyl benzamide quinoline sulfonamide) | B | B | B | B | |
| (3-phenyl-3-hydroxy-azetidinyl benzamide quinoline sulfonamide) | B | B | B | B | BB |

TABLE 1-continued

| Structure | | | | |
|---|---|---|---|---|
| (3-hydroxy-3-phenylazetidine-methylbenzene-sulfonamide-quinoline) | B | B | B | B |
| (3-hydroxy-3-phenylazetidine-OMe-benzene-sulfonamide-quinoline) | B | B | B | B |
| (allyl urea azetidine-benzene-sulfonamide-quinoline) | B | B | B | B |
| (allyl urea azetidine-OMe-benzene-sulfonamide-quinoline) | B | B | B | B |
| (3-hydroxyazetidine-benzene-sulfonamide-quinoline) | B | B | B | B |
| (3-hydroxyazetidine-methylbenzene-sulfonamide-quinoline) | B | B | A | B |
| (3-hydroxyazetidine-OMe-benzene-sulfonamide-quinoline) | B | B | A | B |
| (3-hydroxy-3-methylazetidine-methylbenzene-sulfonamide-quinoline) | B | B | B | B |

TABLE 1-continued

| Structure | | | | |
|---|---|---|---|---|
| (phenylamino-azetidine carbonyl-methylphenyl sulfonamide quinoline) | B | B | B | B |
| (N-benzyl-N-methyl-azetidine carbonyl-phenyl sulfonamide quinoline) | B | B | B | B |
| (benzylamino-azetidine carbonyl-phenyl sulfonamide quinoline) | B | B | B | B |
| (2-methoxypyridin-3-ylamino-azetidine carbonyl-methylphenyl sulfonamide quinoline) | B | B | B | B |
| (3-methoxypyridin-2-ylamino-azetidine carbonyl-methylphenyl sulfonamide quinoline) | B | B | B | B |
| (2-methoxyphenoxy-azetidine carbonyl-methoxyphenyl sulfonamide quinoline) | A | B | B | B |
| (pyridin-2-ylamino-azetidine carbonyl-methylphenyl sulfonamide quinoline) | A | A | B | A |
| (pyridin-4-ylamino-azetidine carbonyl-methylphenyl sulfonamide quinoline) | A | A | A | B |
| (4-methoxypyridin-3-ylamino-azetidine carbonyl-methylphenyl sulfonamide quinoline) | A | A | B | B |

TABLE 1-continued
| Structure | | | | | |
|---|---|---|---|---|---|
| 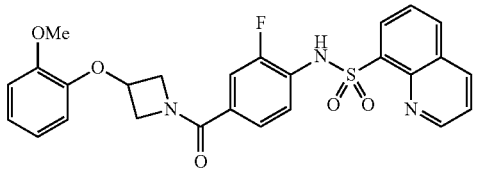 [SMILES: COc1ccccc1OC1CN(C(=O)c2ccc(NS(=O)(=O)c3cccc4cccnc34)c(F)c2)C1] | A | B | B | B | |
| 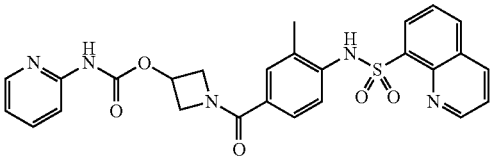 [SMILES: Cc1cc(C(=O)N2CC(OC(=O)Nc3ccccn3)C2)ccc1NS(=O)(=O)c1cccc2cccnc12] | B | B | A | A | |
| 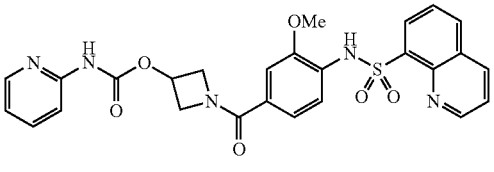 [SMILES: COc1cc(C(=O)N2CC(OC(=O)Nc3ccccn3)C2)ccc1NS(=O)(=O)c1cccc2cccnc12] | B | A | A | A | |
| 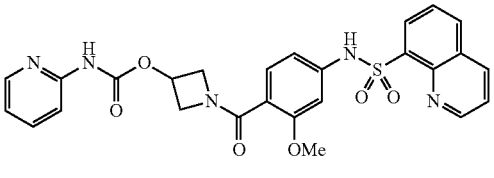 [SMILES: COc1cc(NS(=O)(=O)c2cccc3cccnc23)ccc1C(=O)N1CC(OC(=O)Nc2ccccn2)C1] | B | B | B | B | |
| 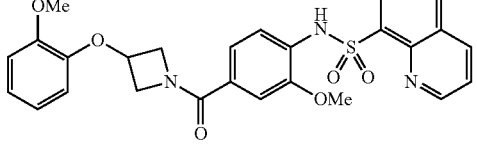 | B | B | B | B | |
| 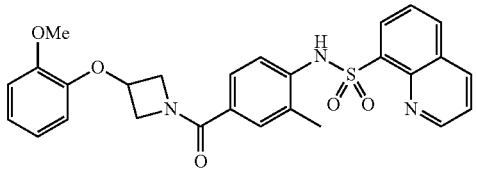 [SMILES: COc1ccccc1OC1CN(C(=O)c2ccc(NS(=O)(=O)c3cccc4cccnc34)c(C)c2)C1] | B | B | A | B | AA |
| 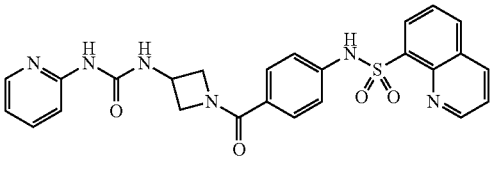 [SMILES: O=C(Nc1ccccn1)NC1CN(C(=O)c2ccc(NS(=O)(=O)c3cccc4cccnc34)cc2)C1] | B | B | B | B | |
| 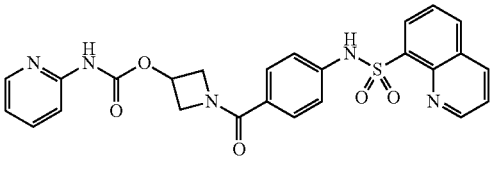 [SMILES: O=C(Nc1ccccn1)OC1CN(C(=O)c2ccc(NS(=O)(=O)c3cccc4cccnc34)cc2)C1] | B | B | B | B | |
| 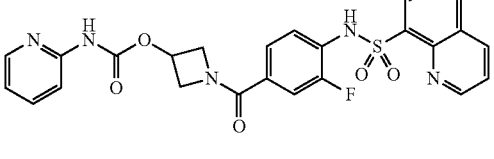 | B | B | B | B | |

TABLE 1-continued

| Structure | | | | |
|---|---|---|---|---|
| (isopropyl urea azetidine benzamide sulfonamide quinoline) | B | B | B | B |
| (isopropyl urea azetidine methyl-benzamide sulfonamide quinoline) | B | B | B | B |
| (benzylidene azetidine benzamide sulfonamide quinoline) | A | A | A | A |

| Structure | PKR R510Q AC50 (μM) | PKR R532W AC50 (μM) | PKR T384W AC50 (μM) | PKR G364D AC50 (μM) | PKR R479H AC50 (μM) |
|---|---|---|---|---|---|
| (phenoxy azetidine benzamide sulfonamide quinoline) | CC | AA | BB | | |
| (benzyl hydroxy azetidine benzamide sulfonamide quinoline) | BB | AA | AA | BB | AA |
| (pyridine carboxylate azetidine benzamide sulfonamide quinoline) | | | | | |
| (pyridine carboxamide azetidine methyl-benzamide sulfonamide quinoline) | CC | BB | BB | | |
| (pyridine carboxamide azetidine benzamide sulfonamide quinoline) | | | | | |

TABLE 1-continued
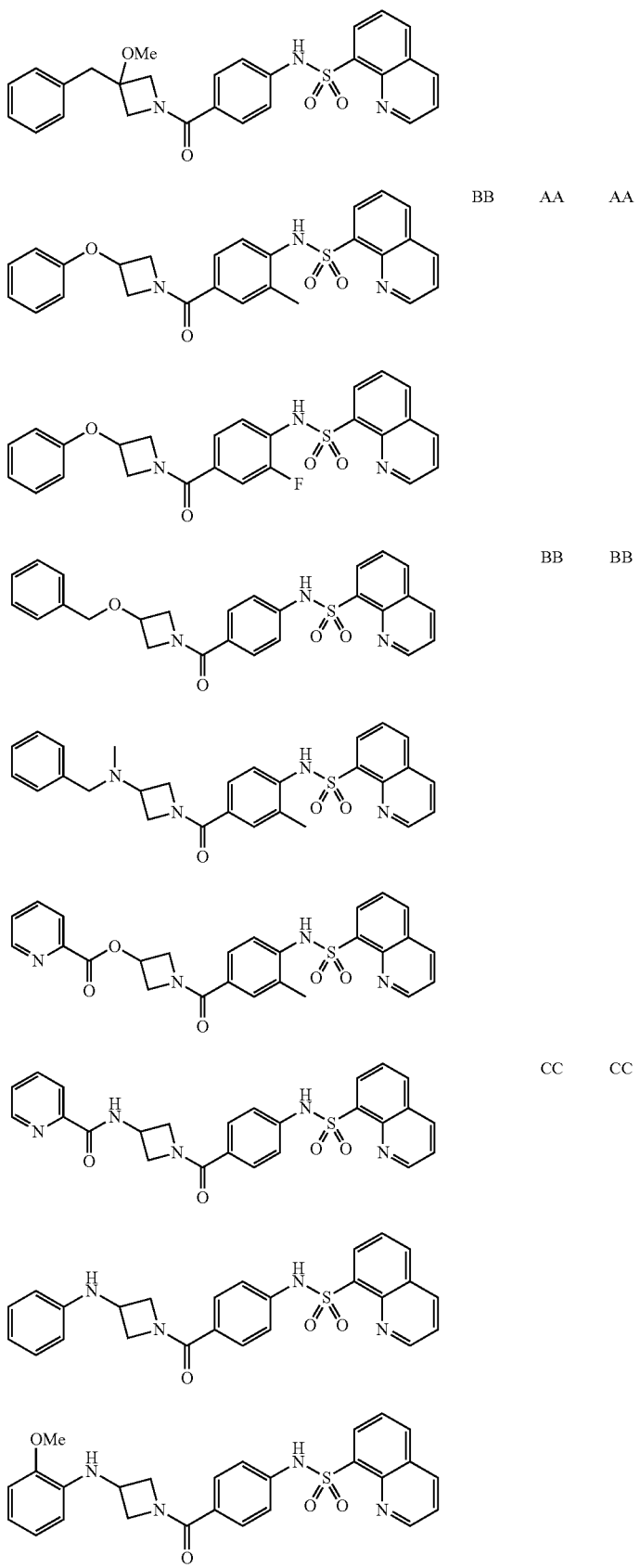
|  | BB | AA | AA |
|---|---|---|---|
|  | BB | BB |  |
|  | CC | CC |  |

TABLE 1-continued
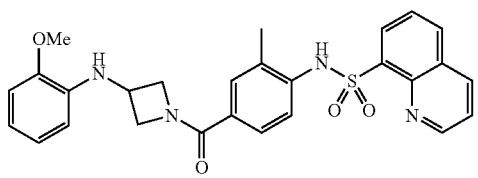 [SMILES: COc1ccccc1NC1CN(C(=O)c2ccc(NS(=O)(=O)c3cccc4cccnc34)c(C)c2)C1]
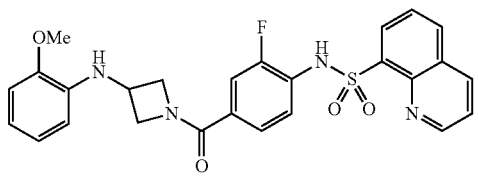 [SMILES: COc1ccccc1NC1CN(C(=O)c2ccc(NS(=O)(=O)c3cccc4cccnc34)c(F)c2)C1]
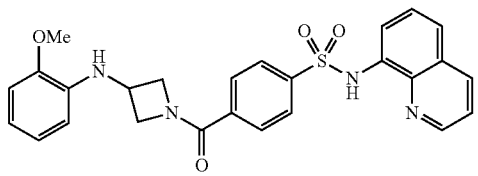 [SMILES: COc1ccccc1NC1CN(C(=O)c2ccc(S(=O)(=O)Nc3cccc4cccnc34)cc2)C1]
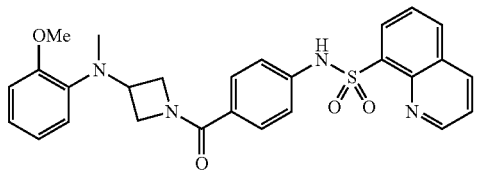
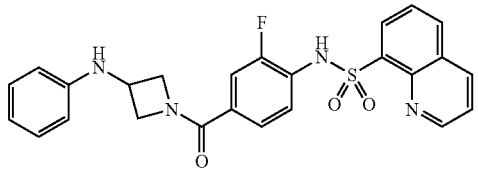 [SMILES: O=C(c1ccc(NS(=O)(=O)c2cccc3cccnc23)c(F)c1)N1CC(Nc2ccccc2)C1]  CC    CC    CC
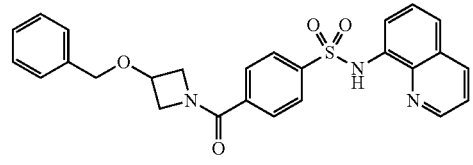 [SMILES: O=C(c1ccc(S(=O)(=O)Nc2cccc3cccnc23)cc1)N1CC(OCc2ccccc2)C1]
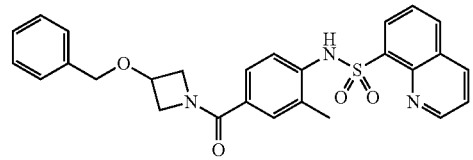 [SMILES: Cc1cc(C(=O)N2CC(OCc3ccccc3)C2)ccc1NS(=O)(=O)c1cccc2cccnc12]
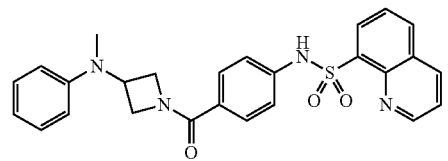 [SMILES: CN(c1ccccc1)C1CN(C(=O)c2ccc(NS(=O)(=O)c3cccc4cccnc34)cc2)C1]

TABLE 1-continued
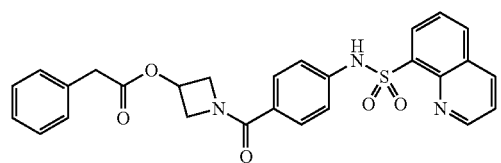 [SMILES: O=C(Cc1ccccc1)OC1CN(C(=O)c2ccc(NS(=O)(=O)c3cccc4cccnc34)cc2)C1]
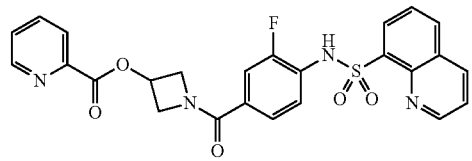 [SMILES: O=C(OC1CN(C(=O)c2ccc(NS(=O)(=O)c3cccc4cccnc34)c(F)c2)C1)c1ccccn1]
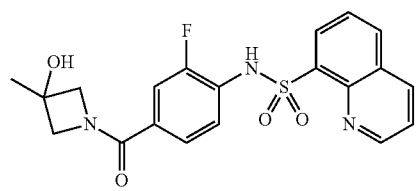
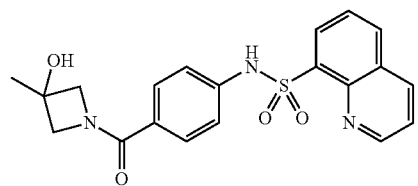 [SMILES: CC1(O)CN(C(=O)c2ccc(NS(=O)(=O)c3cccc4cccnc34)cc2)C1]
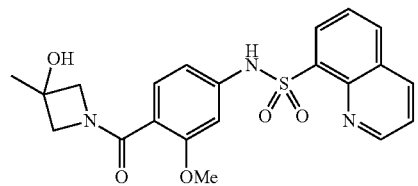 [SMILES: COc1cc(NS(=O)(=O)c2cccc3cccnc23)ccc1C(=O)N1CC(C)(O)C1]
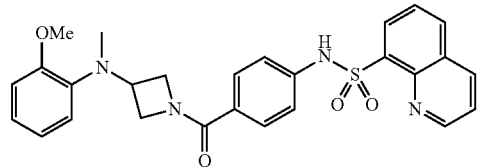 [SMILES: COc1ccccc1N(C)C1CN(C(=O)c2ccc(NS(=O)(=O)c3cccc4cccnc34)cc2)C1]
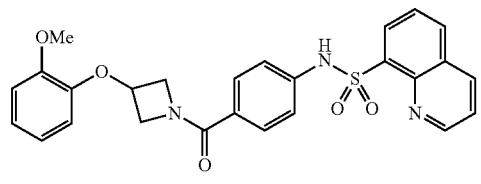 [SMILES: COc1ccccc1OC1CN(C(=O)c2ccc(NS(=O)(=O)c3cccc4cccnc34)cc2)C1]
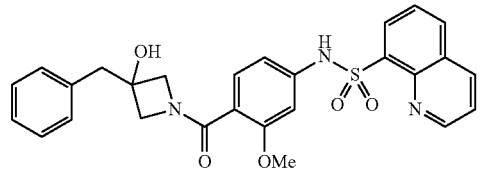 [SMILES: COc1cc(NS(=O)(=O)c2cccc3cccnc23)ccc1C(=O)N1CC(O)(Cc2ccccc2)C1]

TABLE 1-continued
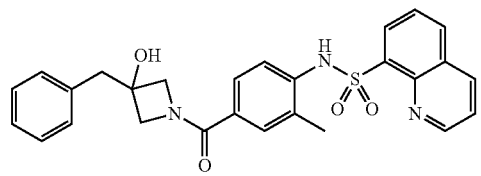 [SMILES: Cc1cc(C(=O)N2CC(O)(Cc3ccccc3)C2)ccc1NS(=O)(=O)c1cccc2cccnc12]
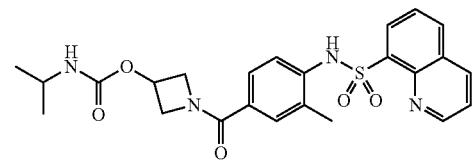 [SMILES: Cc1cc(C(=O)N2CC(OC(=O)NC(C)C)C2)ccc1NS(=O)(=O)c1cccc2cccnc12]
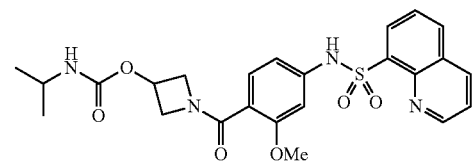 [SMILES: COc1cc(NS(=O)(=O)c2cccc3cccnc23)ccc1C(=O)N1CC(OC(=O)NC(C)C)C1]
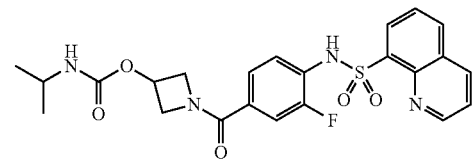 [SMILES: CC(C)NC(=O)OC1CN(C(=O)c2ccc(NS(=O)(=O)c3cccc4cccnc34)c(F)c2)C1]
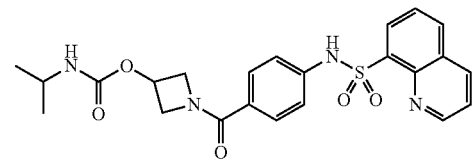 [SMILES: CC(C)NC(=O)OC1CN(C(=O)c2ccc(NS(=O)(=O)c3cccc4cccnc34)cc2)C1]
| | | | | |
|---|---|---|---|---|
| CC | BB | BB | CC | CC |
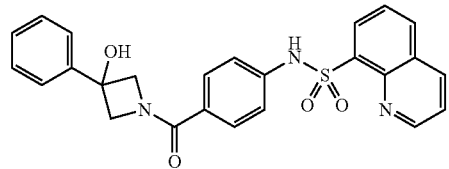 [SMILES: O=C(c1ccc(NS(=O)(=O)c2cccc3cccnc23)cc1)N1CC(O)(c2ccccc2)C1]
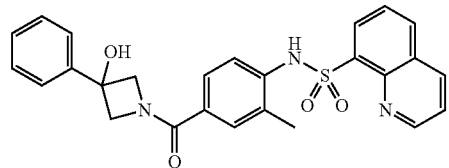 [SMILES: Cc1cc(C(=O)N2CC(O)(c3ccccc3)C2)ccc1NS(=O)(=O)c1cccc2cccnc12]
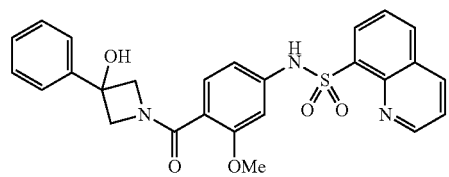 [SMILES: COc1cc(NS(=O)(=O)c2cccc3cccnc23)ccc1C(=O)N1CC(O)(c2ccccc2)C1]
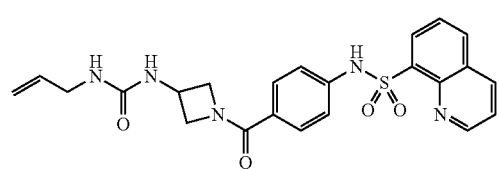 [SMILES: C=CCNC(=O)NC1CN(C(=O)c2ccc(NS(=O)(=O)c3cccc4cccnc34)cc2)C1]

TABLE 1-continued
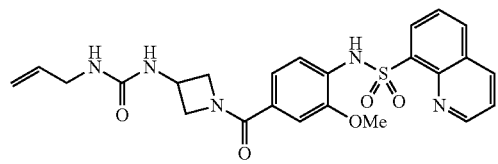 [SMILES: C=CCNC(=O)NC1CN(C(=O)c2ccc(NS(=O)(=O)c3cccc4cccnc34)c(OC)c2)C1]
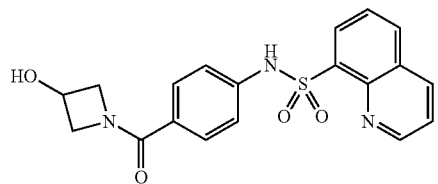 [SMILES: O=C(c1ccc(NS(=O)(=O)c2cccc3cccnc23)cc1)N1CC(O)C1]
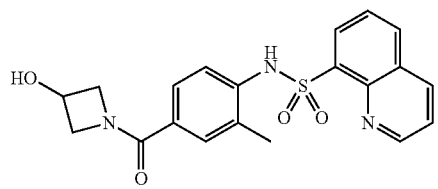 [SMILES: Cc1cc(C(=O)N2CC(O)C2)ccc1NS(=O)(=O)c1cccc2cccnc12]
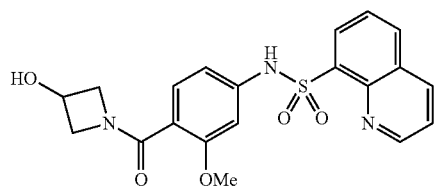 [SMILES: COc1cc(NS(=O)(=O)c2cccc3cccnc23)ccc1C(=O)N1CC(O)C1]
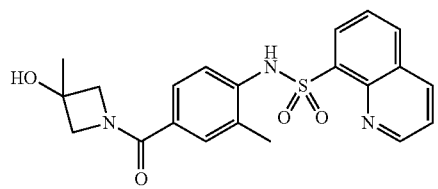 [SMILES: Cc1cc(C(=O)N2CC(C)(O)C2)ccc1NS(=O)(=O)c1cccc2cccnc12]
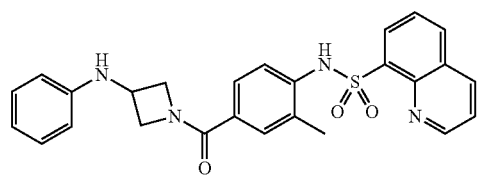 [SMILES: Cc1cc(C(=O)N2CC(Nc3ccccc3)C2)ccc1NS(=O)(=O)c1cccc2cccnc12]
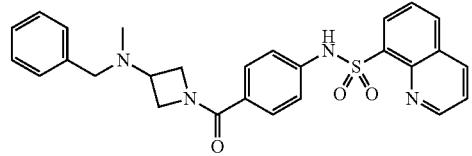 [SMILES: CN(Cc1ccccc1)C1CN(C(=O)c2ccc(NS(=O)(=O)c3cccc4cccnc34)cc2)C1]
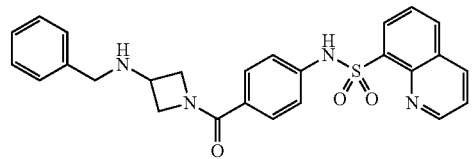 [SMILES: O=C(c1ccc(NS(=O)(=O)c2cccc3cccnc23)cc1)N1CC(NCc2ccccc2)C1]

TABLE 1-continued
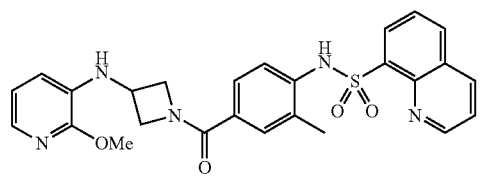 [SMILES: COc1ncccc1NC1CN(C(=O)c2ccc(NS(=O)(=O)c3cccc4cccnc34)c(C)c2)C1]
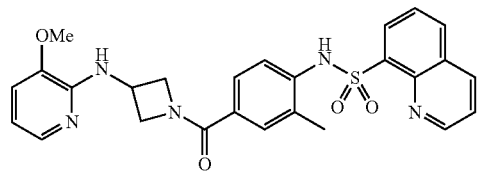 [SMILES: COc1cccnc1NC1CN(C(=O)c2ccc(NS(=O)(=O)c3cccc4cccnc34)c(C)c2)C1]
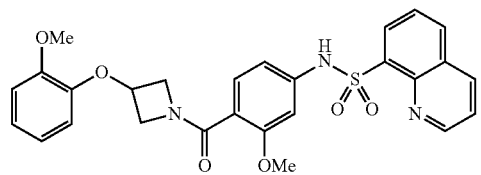 [SMILES: COc1ccccc1OC1CN(C(=O)c2ccc(NS(=O)(=O)c3cccc4cccnc34)cc2OC)C1]
BB
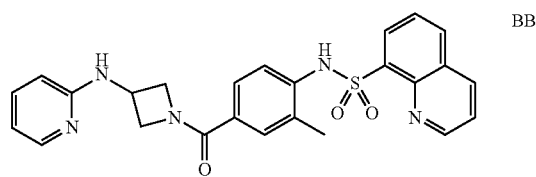
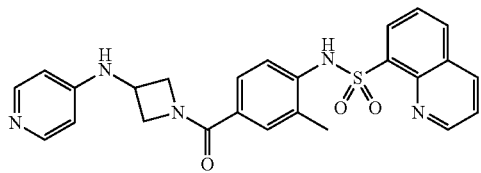 [SMILES: Cc1cc(C(=O)N2CC(Nc3ccncc3)C2)ccc1NS(=O)(=O)c1cccc2cccnc12]
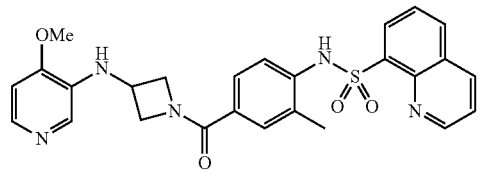 [SMILES: COc1ccncc1NC1CN(C(=O)c2ccc(NS(=O)(=O)c3cccc4cccnc34)c(C)c2)C1]
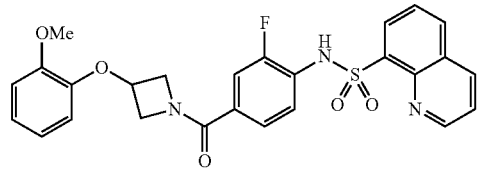 [SMILES: COc1ccccc1OC1CN(C(=O)c2ccc(NS(=O)(=O)c3cccc4cccnc34)c(F)c2)C1]
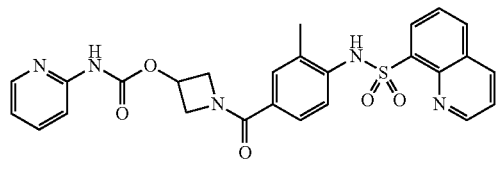 [SMILES: Cc1cc(C(=O)N2CC(OC(=O)Nc3ccccn3)C2)ccc1NS(=O)(=O)c1cccc2cccnc12]
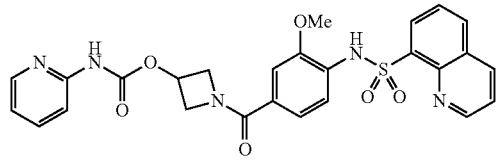 [SMILES: COc1cc(C(=O)N2CC(OC(=O)Nc3ccccn3)C2)ccc1NS(=O)(=O)c1cccc2cccnc12]

TABLE 1-continued
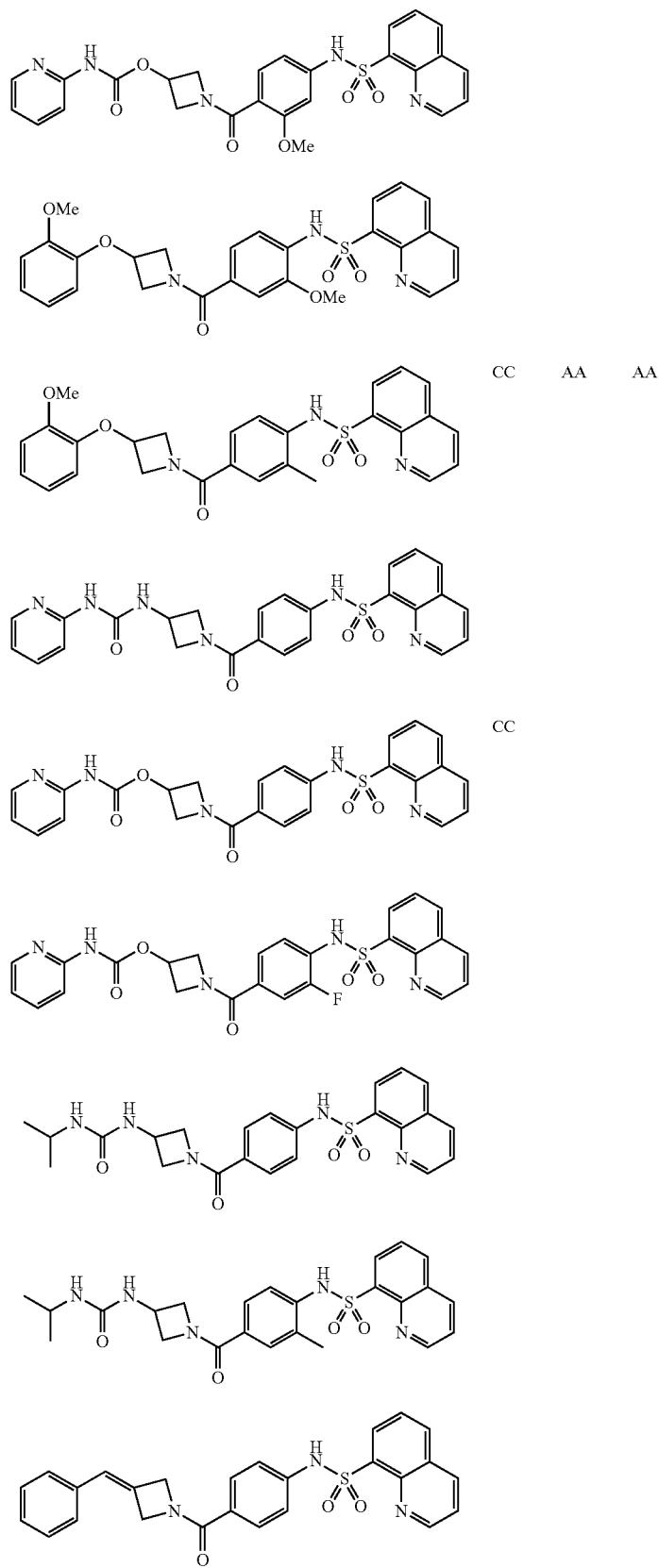

In yet another embodiment, the compound is selected from any one of the compounds set forth in Table 2, below:

TABLE 2

Exemplary Compounds of Formula I:

| Compound | Structure |
|---|---|
| 100 | 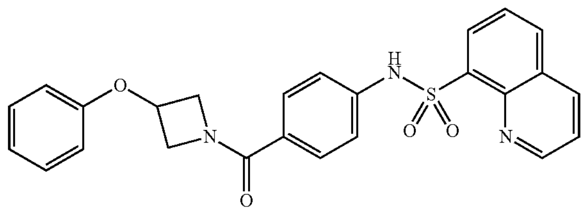 [SMILES: O=C(c1ccc(NS(=O)(=O)c2cccc3cccnc23)cc1)N1CC(Oc2ccccc2)C1] |
| 101 | 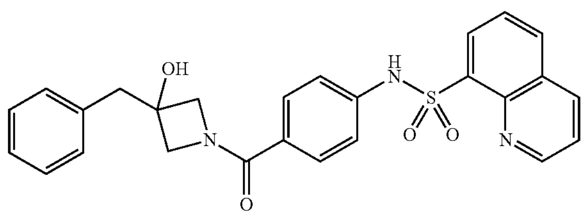 [SMILES: O=C(c1ccc(NS(=O)(=O)c2cccc3cccnc23)cc1)N1CC(O)(Cc2ccccc2)C1] |
| 102 | 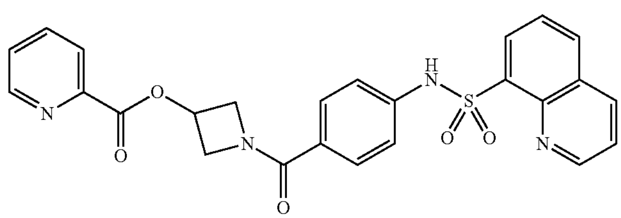 [SMILES: O=C(OC1CN(C(=O)c2ccc(NS(=O)(=O)c3cccc4cccnc34)cc2)C1)c1ccccn1] |
| 103 | 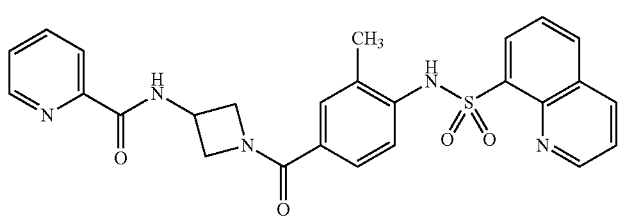 [SMILES: Cc1cc(C(=O)N2CC(NC(=O)c3ccccn3)C2)ccc1NS(=O)(=O)c1cccc2cccnc12] |
| 104 | 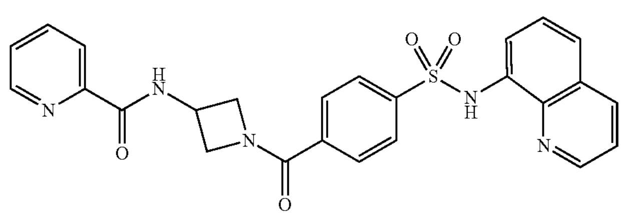 [SMILES: O=C(NC1CN(C(=O)c2ccc(S(=O)(=O)Nc3cccc4cccnc34)cc2)C1)c1ccccn1] |
| 105 | 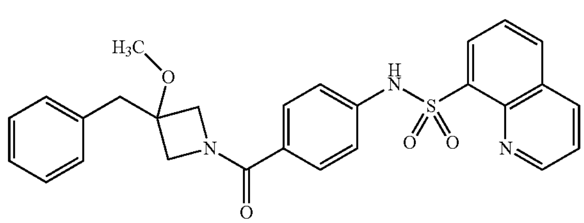 [SMILES: COC1(Cc2ccccc2)CN(C(=O)c2ccc(NS(=O)(=O)c3cccc4cccnc34)cc2)C1] |

TABLE 2-continued

Exemplary Compounds of Formula I:

| Compound | Structure |
|---|---|
| 106 | 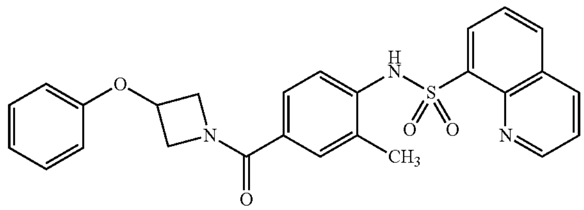 [SMILES: Cc1cc(C(=O)N2CC(Oc3ccccc3)C2)ccc1NS(=O)(=O)c1cccc2cccnc12] |
| 107 | 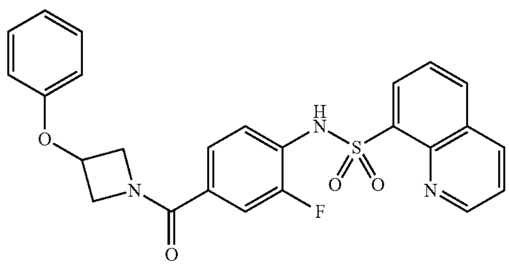 [SMILES: O=C(c1ccc(NS(=O)(=O)c2cccc3cccnc23)c(F)c1)N1CC(Oc2ccccc2)C1] |
| 108 | 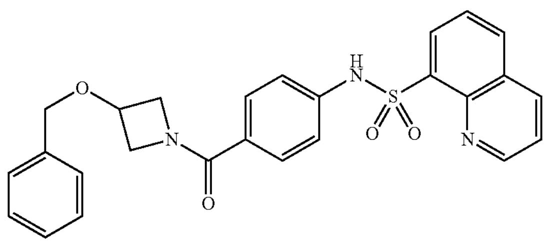 [SMILES: O=C(c1ccc(NS(=O)(=O)c2cccc3cccnc23)cc1)N1CC(OCc2ccccc2)C1] |
| 109 | 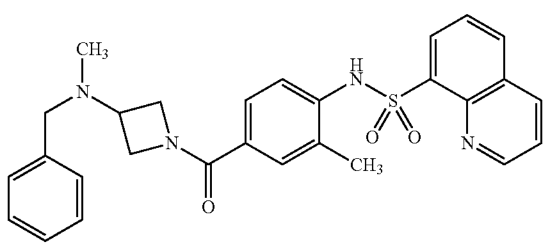 [SMILES: Cc1cc(C(=O)N2CC(N(C)Cc3ccccc3)C2)ccc1NS(=O)(=O)c1cccc2cccnc12] |
| 110 | 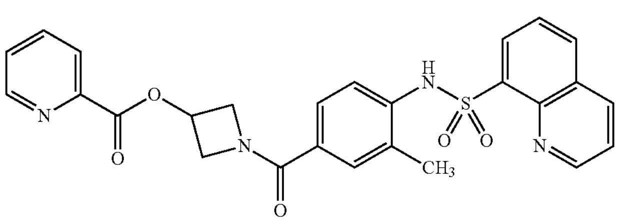 [SMILES: Cc1cc(C(=O)N2CC(OC(=O)c3ccccn3)C2)ccc1NS(=O)(=O)c1cccc2cccnc12] |
| 111 | 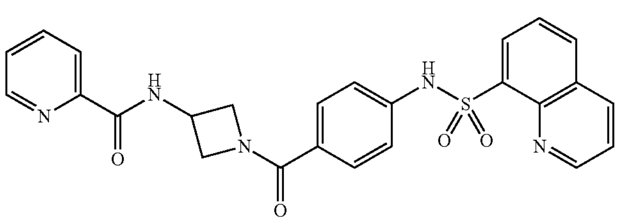 [SMILES: O=C(NC1CN(C(=O)c2ccc(NS(=O)(=O)c3cccc4cccnc34)cc2)C1)c1ccccn1] |

TABLE 2-continued

Exemplary Compounds of Formula I:

| Compound | Structure |
|---|---|
| 112 | 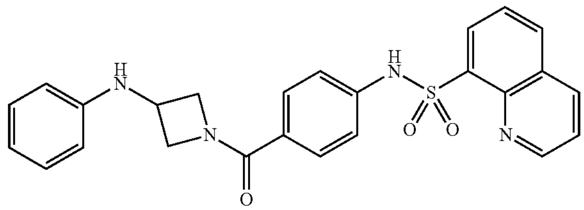 [SMILES: O=C(c1ccc(NS(=O)(=O)c2cccc3cccnc23)cc1)N1CC(Nc2ccccc2)C1] |
| 113 | 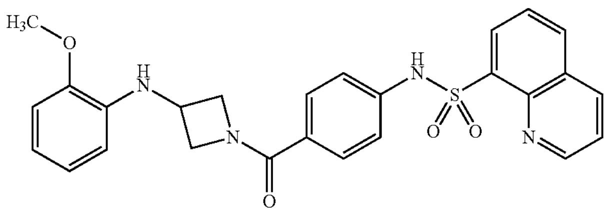 [SMILES: COc1ccccc1NC1CN(C(=O)c2ccc(NS(=O)(=O)c3cccc4cccnc34)cc2)C1] |
| 114 | 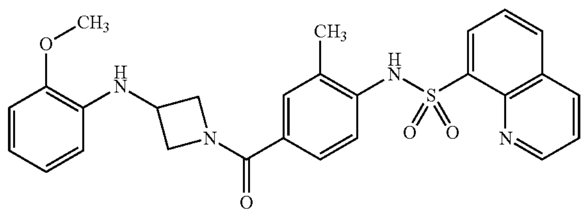 [SMILES: COc1ccccc1NC1CN(C(=O)c2ccc(NS(=O)(=O)c3cccc4cccnc34)c(C)c2)C1] |
| 115 | 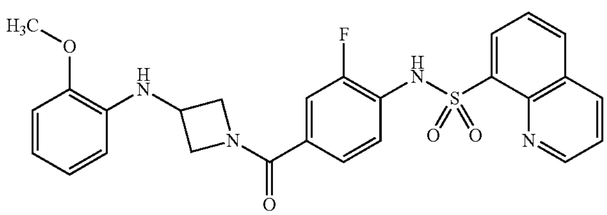 [SMILES: COc1ccccc1NC1CN(C(=O)c2ccc(NS(=O)(=O)c3cccc4cccnc34)c(F)c2)C1] |
| 116 | 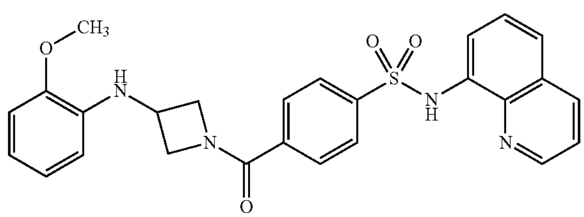 [SMILES: COc1ccccc1NC1CN(C(=O)c2ccc(S(=O)(=O)Nc3cccc4cccnc34)cc2)C1] |
| 117 | 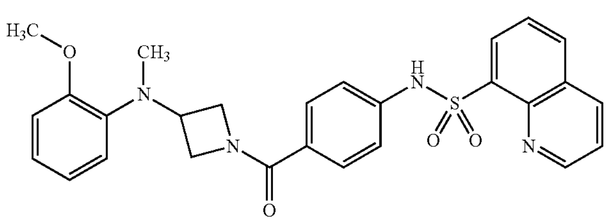 [SMILES: COc1ccccc1N(C)C1CN(C(=O)c2ccc(NS(=O)(=O)c3cccc4cccnc34)cc2)C1] |
| 118 | 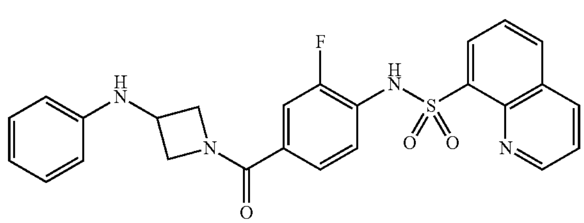 [SMILES: O=C(c1ccc(NS(=O)(=O)c2cccc3cccnc23)c(F)c1)N1CC(Nc2ccccc2)C1] |

TABLE 2-continued
Exemplary Compounds of Formula I:
| Compound | Structure |
|---|---|
| 119 | 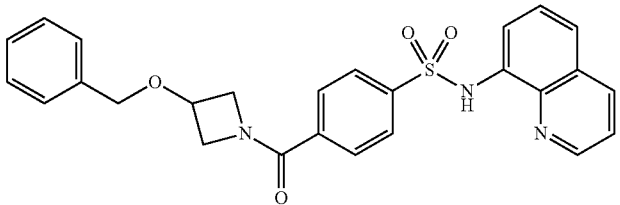 [SMILES: O=C(c1ccc(S(=O)(=O)Nc2cccc3cccnc23)cc1)N1CC(OCc2ccccc2)C1] |
| 120 | 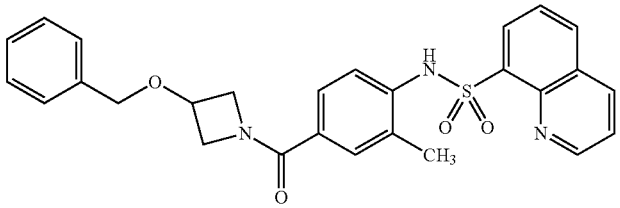 [SMILES: Cc1cc(C(=O)N2CC(OCc3ccccc3)C2)ccc1NS(=O)(=O)c1cccc2cccnc12] |
| 121 | 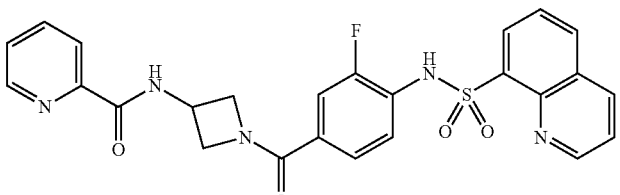 |
| 122 | 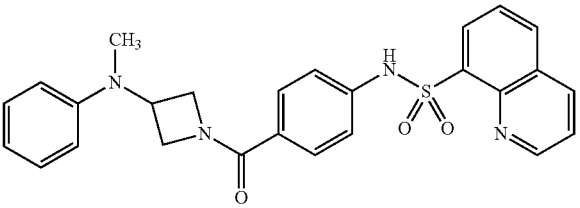 [SMILES: CN(c1ccccc1)C1CN(C(=O)c2ccc(NS(=O)(=O)c3cccc4cccnc34)cc2)C1] |
| 123 | 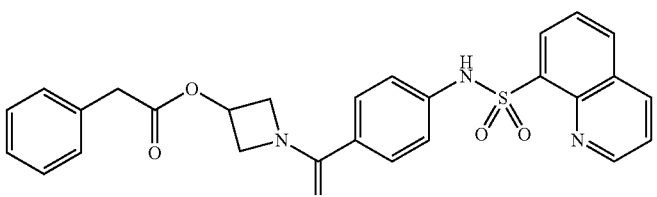 |
| 124 | 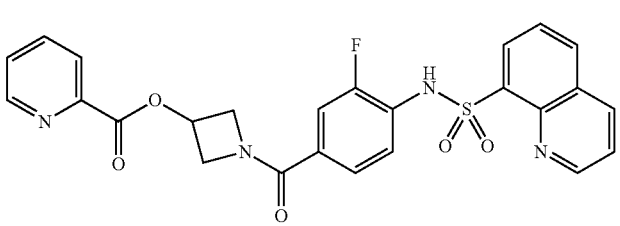 [SMILES: O=C(OC1CN(C(=O)c2ccc(NS(=O)(=O)c3cccc4cccnc34)c(F)c2)C1)c1ccccn1] |
| 125 | 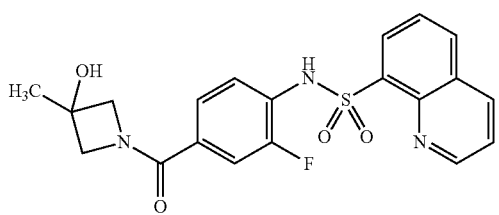 [SMILES: CC1(O)CN(C(=O)c2ccc(NS(=O)(=O)c3cccc4cccnc34)c(F)c2)C1] |

TABLE 2-continued

Exemplary Compounds of Formula I:

| Compound | Structure |
|---|---|
| 126 | 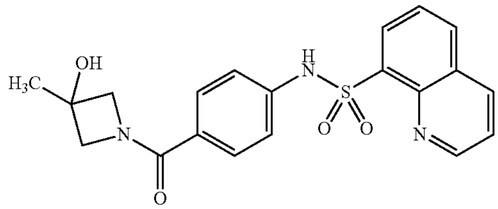 [SMILES: CC1(O)CN(C(=O)c2ccc(NS(=O)(=O)c3cccc4cccnc34)cc2)C1] |
| 127 | 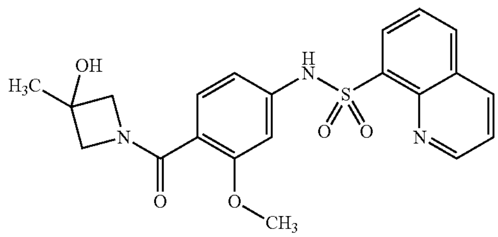 [SMILES: COc1cc(NS(=O)(=O)c2cccc3cccnc23)ccc1C(=O)N1CC(C)(O)C1] |
| 128 | 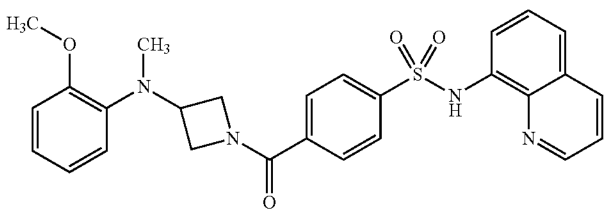 [SMILES: COc1ccccc1N(C)C1CN(C(=O)c2ccc(S(=O)(=O)Nc3cccc4cccnc34)cc2)C1] |
| 129 | 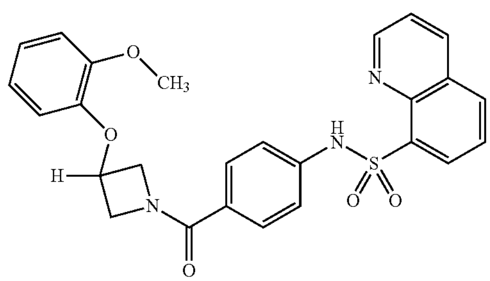 [SMILES: COc1ccccc1OC1CN(C(=O)c2ccc(NS(=O)(=O)c3cccc4cccnc34)cc2)C1] |
| 130 | 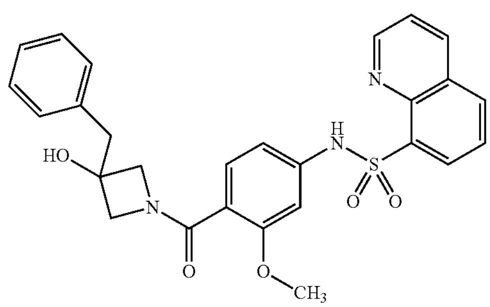 |
| 131 | 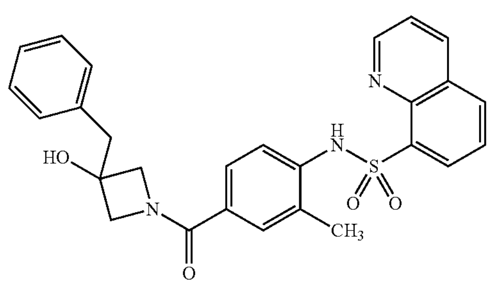 [SMILES: Cc1cc(C(=O)N2CC(O)(Cc3ccccc3)C2)ccc1NS(=O)(=O)c1cccc2cccnc12] |

TABLE 2-continued

Exemplary Compounds of Formula I:

| Compound | Structure |
|---|---|
| 132 | 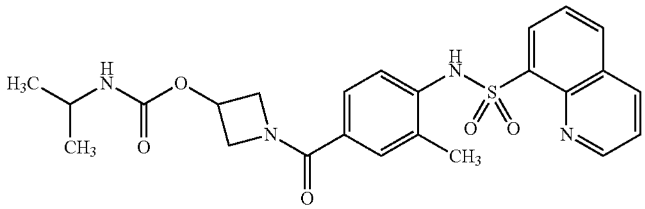 [SMILES: Cc1cc(C(=O)N2CC(OC(=O)NC(C)C)C2)ccc1NS(=O)(=O)c1cccc2cccnc12] |
| 133 | 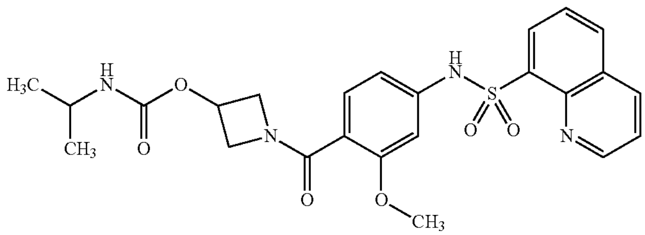 [SMILES: COc1cc(NS(=O)(=O)c2cccc3cccnc23)ccc1C(=O)N1CC(OC(=O)NC(C)C)C1] |
| 134 | 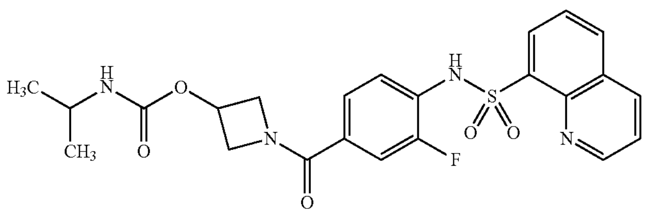 [SMILES: CC(C)NC(=O)OC1CN(C(=O)c2ccc(NS(=O)(=O)c3cccc4cccnc34)c(F)c2)C1] |
| 135 | 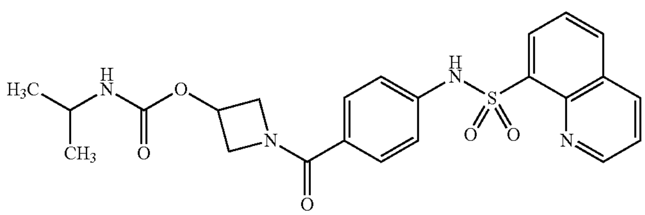 [SMILES: CC(C)NC(=O)OC1CN(C(=O)c2ccc(NS(=O)(=O)c3cccc4cccnc34)cc2)C1] |
| 136 | 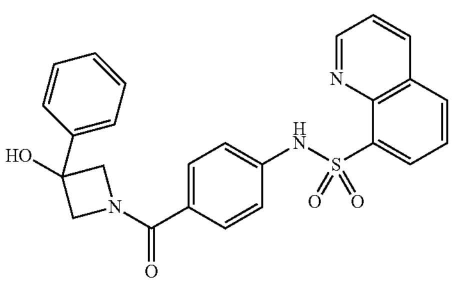 [SMILES: O=C(c1ccc(NS(=O)(=O)c2cccc3cccnc23)cc1)N1CC(O)(c2ccccc2)C1] |
| 137 | 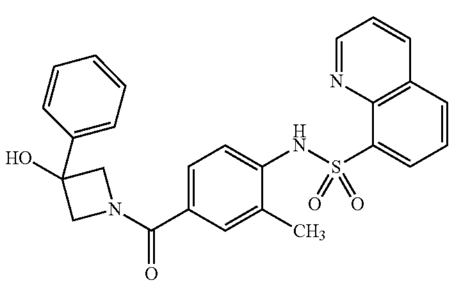 [SMILES: Cc1cc(C(=O)N2CC(O)(c3ccccc3)C2)ccc1NS(=O)(=O)c1cccc2cccnc12] |

TABLE 2-continued

Exemplary Compounds of Formula I:

| Compound | Structure |
|---|---|
| 138 | 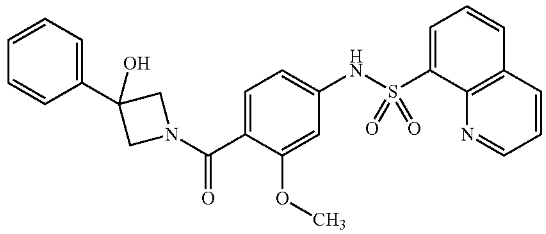 [SMILES: COc1cc(NS(=O)(=O)c2cccc3cccnc23)ccc1C(=O)N1CC(O)(c2ccccc2)C1] |
| 139 | 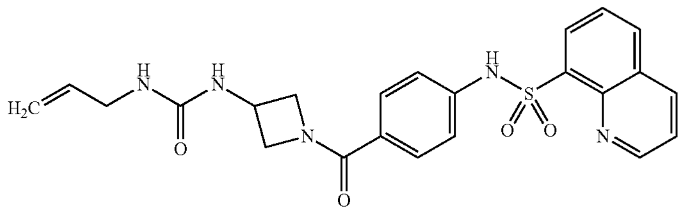 [SMILES: C=CCNC(=O)NC1CN(C(=O)c2ccc(NS(=O)(=O)c3cccc4cccnc34)cc2)C1] |
| 140 | 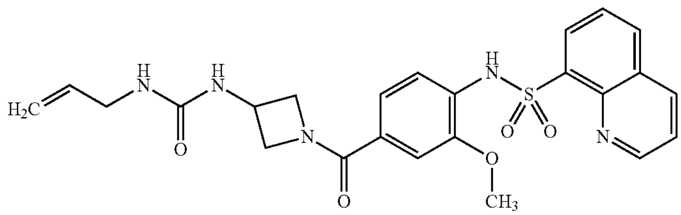 [SMILES: C=CCNC(=O)NC1CN(C(=O)c2ccc(NS(=O)(=O)c3cccc4cccnc34)c(OC)c2)C1] |
| 141 | 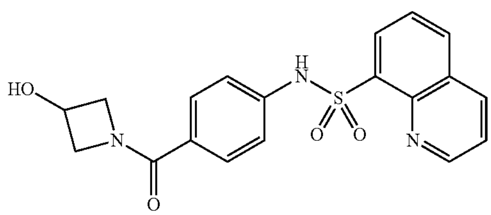 [SMILES: O=C(c1ccc(NS(=O)(=O)c2cccc3cccnc23)cc1)N1CC(O)C1] |
| 142 | 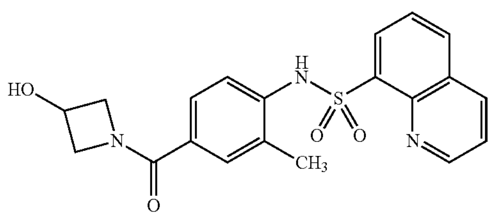 [SMILES: Cc1cc(C(=O)N2CC(O)C2)ccc1NS(=O)(=O)c1cccc2cccnc12] |
| 143 | 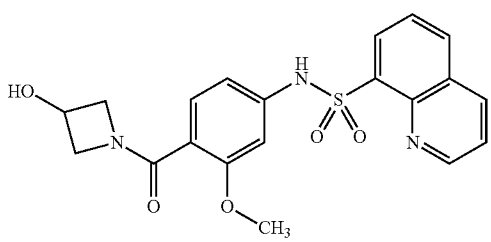 [SMILES: COc1cc(NS(=O)(=O)c2cccc3cccnc23)ccc1C(=O)N1CC(O)C1] |
| 144 | 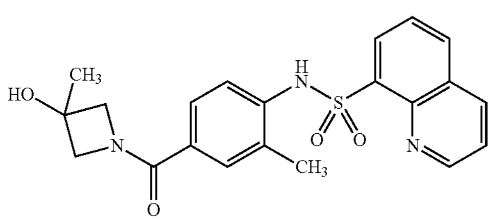 [SMILES: Cc1cc(C(=O)N2CC(C)(O)C2)ccc1NS(=O)(=O)c1cccc2cccnc12] |

TABLE 2-continued

Exemplary Compounds of Formula I:

| Compound | Structure |
|---|---|
| 145 | 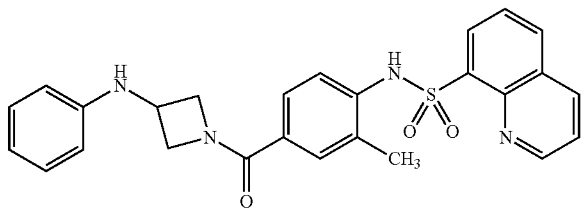 [SMILES: Cc1cc(C(=O)N2CC(Nc3ccccc3)C2)ccc1NS(=O)(=O)c1cccc2cccnc12] |
| 146 | 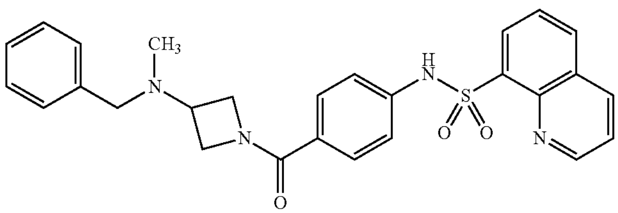 [SMILES: CN(Cc1ccccc1)C1CN(C(=O)c2ccc(NS(=O)(=O)c3cccc4cccnc34)cc2)C1] |
| 147 | 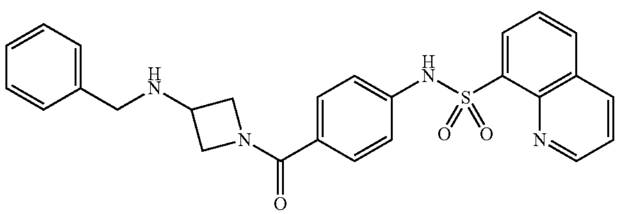 [SMILES: O=C(c1ccc(NS(=O)(=O)c2cccc3cccnc23)cc1)N1CC(NCc2ccccc2)C1] |
| 148 | 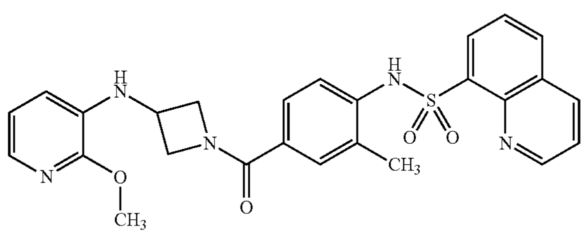 [SMILES: COc1ncccc1NC1CN(C(=O)c2ccc(NS(=O)(=O)c3cccc4cccnc34)c(C)c2)C1] |
| 149 | 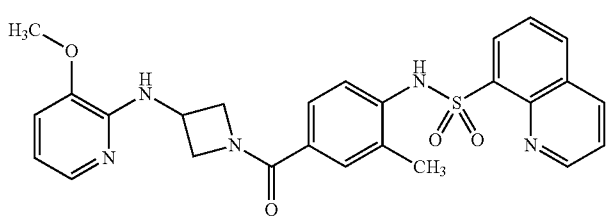 [SMILES: COc1cccnc1NC1CN(C(=O)c2ccc(NS(=O)(=O)c3cccc4cccnc34)c(C)c2)C1] |
| 150 | 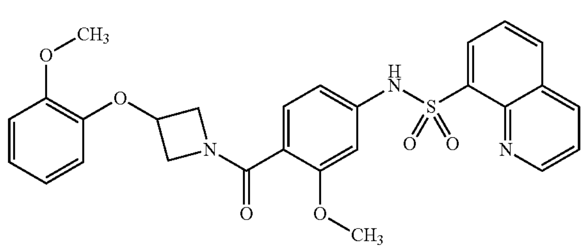 [SMILES: COc1ccccc1OC1CN(C(=O)c2ccc(NS(=O)(=O)c3cccc4cccnc34)cc2OC)C1] |

TABLE 2-continued

Exemplary Compounds of Formula I:

| Compound | Structure |
|---|---|
| 151 | 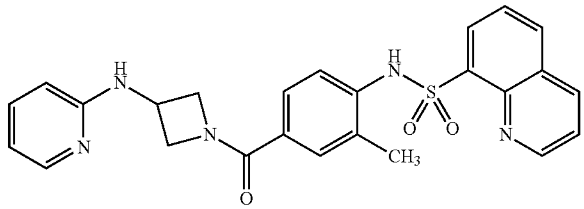 [SMILES: Cc1cc(C(=O)N2CC(Nc3ccccn3)C2)ccc1NS(=O)(=O)c1cccc2cccnc12] |
| 152 | 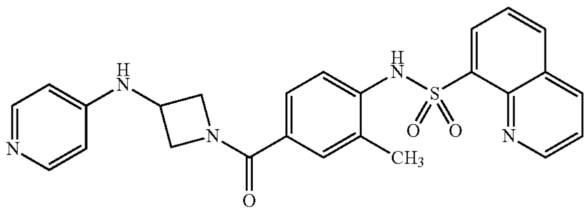 [SMILES: Cc1cc(C(=O)N2CC(Nc3ccncc3)C2)ccc1NS(=O)(=O)c1cccc2cccnc12] |
| 153 | 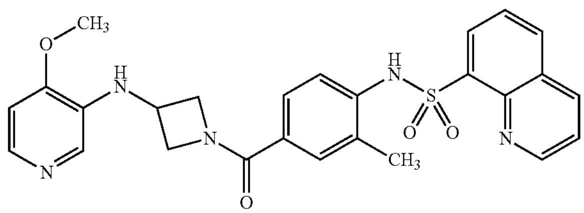 [SMILES: COc1ccncc1NC1CN(C(=O)c2ccc(NS(=O)(=O)c3cccc4cccnc34)c(C)c2)C1] |
| 154 | 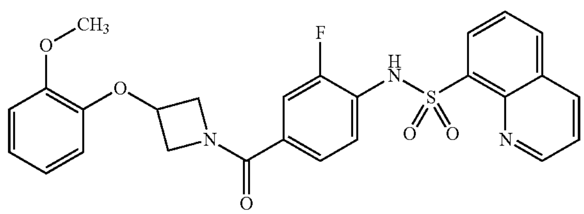 [SMILES: COc1ccccc1OC1CN(C(=O)c2ccc(NS(=O)(=O)c3cccc4cccnc34)c(F)c2)C1] |
| 155 | 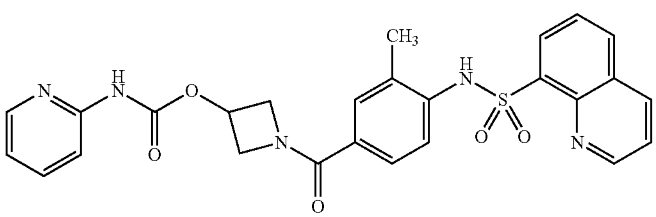 [SMILES: Cc1cc(C(=O)N2CC(OC(=O)Nc3ccccn3)C2)ccc1NS(=O)(=O)c1cccc2cccnc12] |
| 156 | 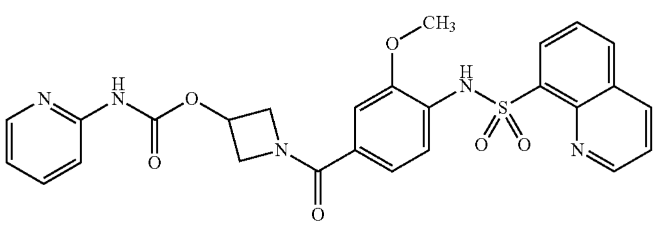 [SMILES: COc1cc(C(=O)N2CC(OC(=O)Nc3ccccn3)C2)ccc1NS(=O)(=O)c1cccc2cccnc12] |
| 157 | 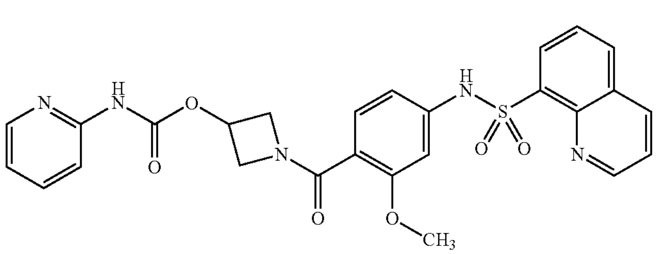 [SMILES: COc1cc(NS(=O)(=O)c2cccc3cccnc23)ccc1C(=O)N1CC(OC(=O)Nc2ccccn2)C1] |

TABLE 2-continued

Exemplary Compounds of Formula I:

| Compound | Structure |
|---|---|
| 158 | 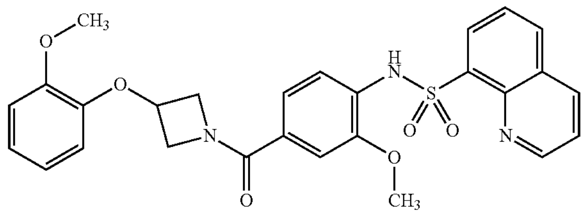 [SMILES: COc1cc(C(=O)N2CC(Oc3ccccc3OC)C2)ccc1NS(=O)(=O)c1cccc2cccnc12] |
| 159 | 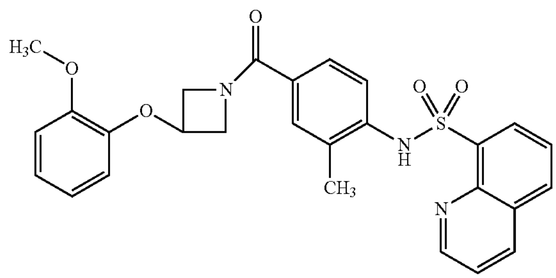 [SMILES: COc1ccccc1OC1CN(C(=O)c2ccc(NS(=O)(=O)c3cccc4cccnc34)c(C)c2)C1] |
| 160 | 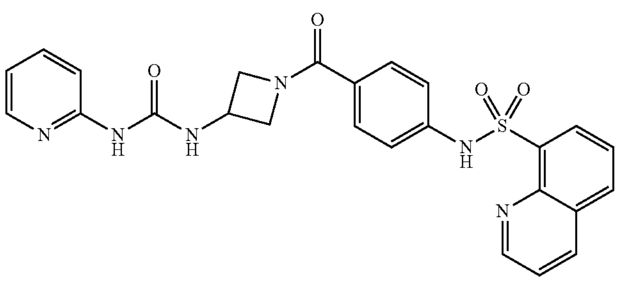 [SMILES: O=C(Nc1ccccn1)NC1CN(C(=O)c2ccc(NS(=O)(=O)c3cccc4cccnc34)cc2)C1] |
| 161 | 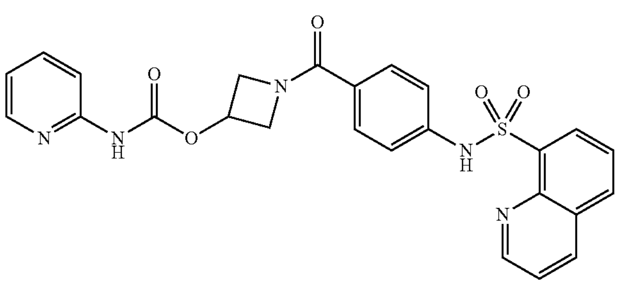 [SMILES: O=C(Nc1ccccn1)OC1CN(C(=O)c2ccc(NS(=O)(=O)c3cccc4cccnc34)cc2)C1] |
| 162 | 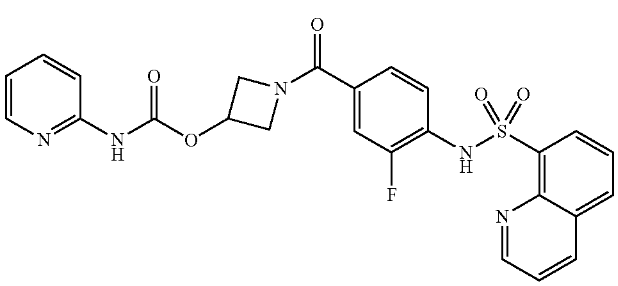 [SMILES: O=C(Nc1ccccn1)OC1CN(C(=O)c2ccc(NS(=O)(=O)c3cccc4cccnc34)c(F)c2)C1] |

TABLE 2-continued

Exemplary Compounds of Formula I:

| Compound | Structure |
|---|---|
| 163 | 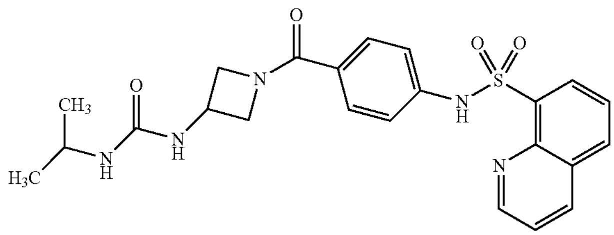 [SMILES: CC(C)NC(=O)NC1CN(C(=O)c2ccc(NS(=O)(=O)c3cccc4cccnc34)cc2)C1] |
| 164 | 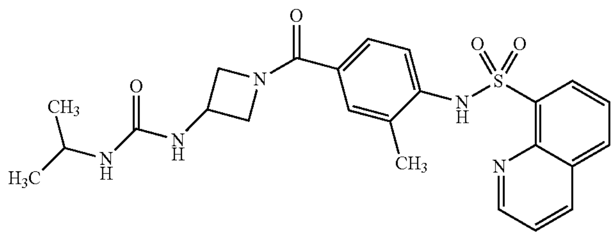 [SMILES: Cc1cc(C(=O)N2CC(NC(=O)NC(C)C)C2)ccc1NS(=O)(=O)c1cccc2cccnc12] |
| 165 | 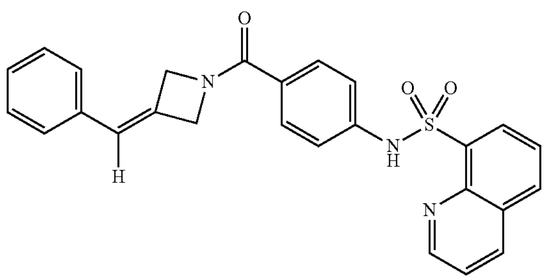 [SMILES: O=C(c1ccc(NS(=O)(=O)c2cccc3cccnc23)cc1)N1CC(=Cc2ccccc2)C1] |
| 166 | 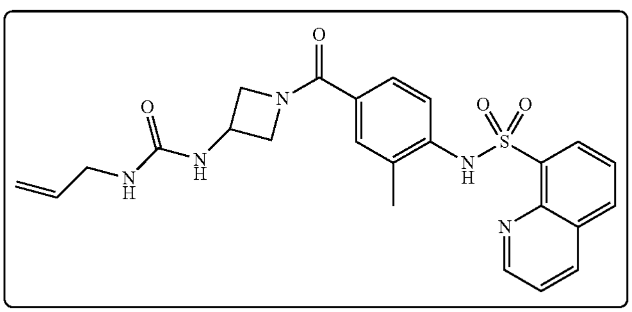 [SMILES: C=CCNC(=O)NC1CN(C(=O)c2ccc(NS(=O)(=O)c3cccc4cccnc34)c(C)c2)C1] |

The compounds described herein can be made using a variety of synthetic techniques, general and specific examples of which are set forth in Example section.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g., restriction resulting from the presence of a ring or double bond. Accordingly, all cis/trans and E/Z isomers are expressly included.

The compounds provided herein (e.g., of Formula I) may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Certain activator compounds useful as PKR wild type and/or mutant activators are those that demonstrate specificity and activation of PKR enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (II), or in Figure 1).

The compounds and compositions described herein can be administered to cells in culture, e.g., in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a disorder (e.g., a disorder as described herein), a symptom of a disorder, with the purpose to cure, heal, alleviate, relieve, alter, remedy, ameliorate, improve or affect the disorder, or one or more symptoms of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "prevent" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a predisposition toward a disorder, with the purpose to prevent the occurrence of at least one symptom of the disorder or to delay onset of at least one symptom of the disorder).

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

Example 1

Synthesis of Compounds of Formula II, Wherein $R^{1a}$ is Benzyl $R^{1b}$ and is Hydroxyl or Methoxy Compounds of Formula II, wherein $R^{1a}$ is benzyl $R^{1b}$ and is hydroxyl or methoxy are produced by Scheme 1 as follows:

Scheme 1:

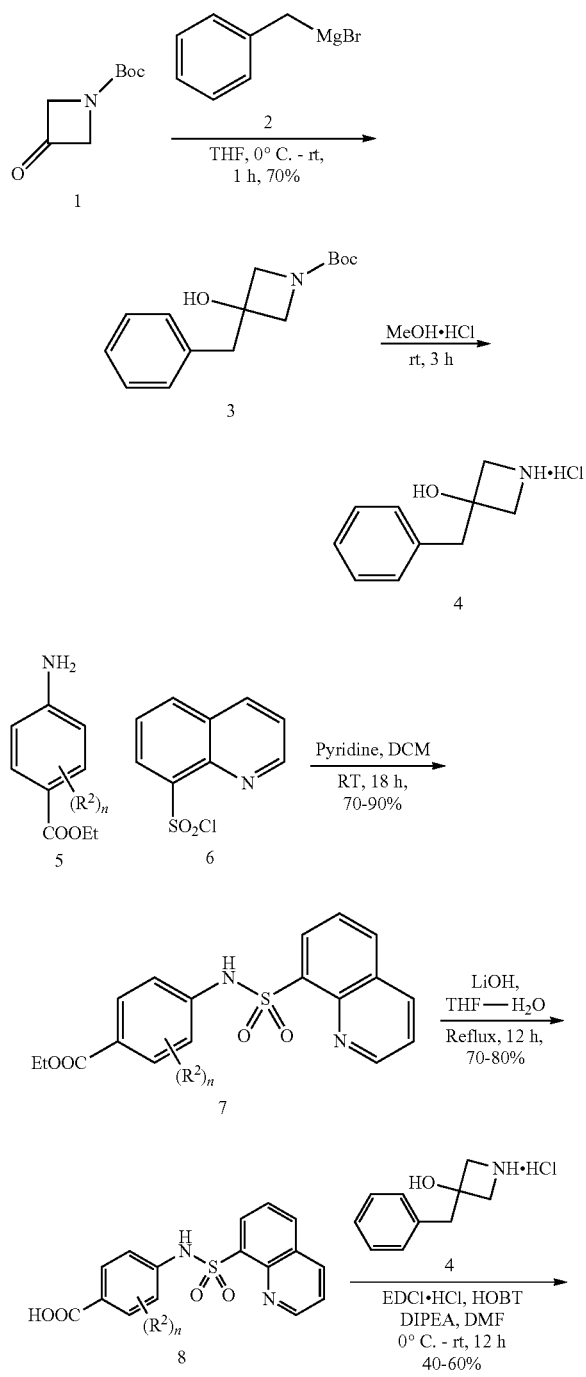

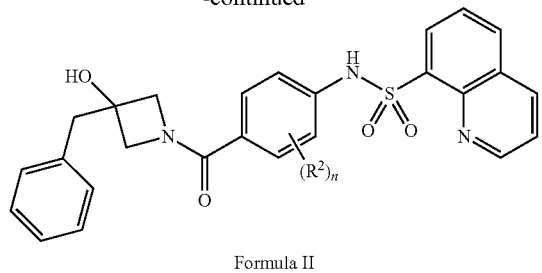

Formula II

Procedure for preparation of tert-butyl 3-benzyl-3-hydroxyazetidine-1-carboxylate (3)

1-Boc-3-azetidinone (1) (2.0 gm, 11.68 mmol) was dissolved in dry THF (20 ml) under nitrogen and cooled to 0° C. Then the solution was added 2.0 M solution of Benzyl magnesium bromide (2) in THF (8.76 ml, 17.52 mmol) under nitrogen atmosphere. The reaction mixture was then allowed to warm to room temperature and stirred for 1 h. The reaction completion was monitored by TLC. The reaction was quenched by the addition of saturated ammonium chloride solution and extracted ethyl acetate. The organic layer was dried over anhydrous sodium sulfate, filtered and concentrated under vacuum. Crude product was then purified by column chromatography to give compound 3 (2.15 gm, 70%). $^1$H NMR (400 MHz, DMSOd$_6$) δ: 1.40 (s, 9H), 2.25 (s, 2H), 4.00 (d, 2H), 4.35 (d, 2H), 6.05 (s, 1H), 7.18 (m, 3H), 7.25 (d, 2H); MS: m/z 263.90 (M+1)$^+$.

Procedure for preparation of 3-benzylazetidin-3-ol hydrochloride (4)

tert-butyl 3-benzyl-3-hydroxyazetidine-1-carboxylate 3 (2.0 gm, 7.59 mmol) was taken into a round bottomed flask and was added methanolic-HCl (25 mL, 20%) and was stirred for 3 h at room temperature. After completion of the reaction (monitored by TLC), the solvent was removed under vacuum to get a white solid as a crude product. The crude product was washed with ethyl acetate repeatedly and then dried well to obtain compound 4 as a white solid (1.36 gm, 90%) which was used without further purification.

General Procedure for Preparation of Compound 7

To stirred a solution of amine 5 (30.16 mmol) in a 1:1 mixture of DCM-pyridine (50+50 ml) was added quinoline-8-sulfonyl chloride (6) (8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 mL), 1N HCl solution (3×50 ml) and brine (50 ml). The organic extracts were dried over anhydrous sodium sulfate, filtered and concentrated under vacuum to obtain the crude product. Crude product was co-distilled with toluene to remove the remnants of pyridine and dried to get ester (7) (70-90%) as an off-white solid. This product was used as such for the next step without further purification.

General Procedure for Preparation of Compound 8

A stirred solution of ester 7 (10.05 mmol) in a mixture of THF-water (50+50 ml) was added LiOH (2.11 g, 50.25 mmol) and the resultant solution was refluxed overnight. After completion of the reaction (monitored by TLC), the reaction mixture was extracted with ethyl acetate (3×50 ml) and then acidified with dilute HCl. The resultant suspension was filtered and residue was co-distilled with toluene. The product was then dried under vacuum to get carboxylic acid 8 (70-80%) as an off-white solid.

General Procedure for Compounds of Formula II, Wherein $R^{1a}$ is Benzyl $R^{1b}$ and is Hydroxyl or Methoxy To a stirred solution of the carboxylic acid 8 (0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine hydrochloride 4 (0.61 mmol) was then added at 0° C. and stirred overnight at room temperature. After completion of the reaction (monitored by TLC), the reaction mixture was poured into 1.0 M HCl and extracted with EtOAc. The organic layer was washed with sat. aq. NaHCO$_3$, dried over NaSO$_4$ and filtered. The solvent was removed by rotary evaporation and the product was isolated by chromatography on silica gel (60-120 silica gel, 2% MeOH-DCM) or preparative HPLC to yield amide final compound (40-60%) as an off-white solid.

Compound 101

N-(4-(3-benzyl-3-hydroxyazetidine-1-carbonyl)phenyl)quinoline-8-sulfonamide

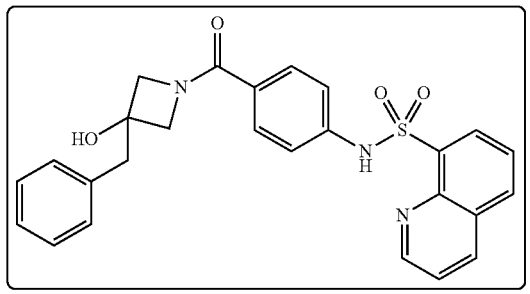 [SMILES: O=C(c1ccc(NS(=O)(=O)c2cccc3cccnc23)cc1)N1CC(O)(Cc2ccccc2)C1]

$^1$H NMR (400 MHz, DMSOd$_6$) δ: 2.2 (dd, 3H), 4.1-4.2 (dd, 2H), 4.5 (d, 1H), 4.8 (d, 1H), 6.1 (s, 1H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 96.0%; MS: m/z 474.0 (M+1)$^+$.

Compound 105

N-(4-(3-benzyl-3-methoxyazetidine-1-carbonyl)phenyl)quinoline-8-sulfonamide

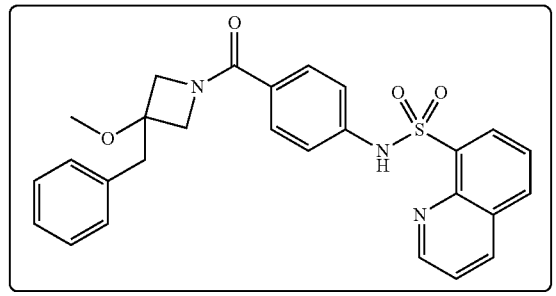 [SMILES: COC1(Cc2ccccc2)CN(C(=O)c2ccc(NS(=O)(=O)c3cccc4cccnc34)cc2)C1]

$^1$H NMR (400 MHz, DMSOd$_6$) δ: 3.8 (s, 3H), 3.9 (s, 2H), 4.1 (s, 2H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 97.0%; MS: m/z 488.1 (M+1)$^+$.

Compound 131

N-(4-(3-benzyl-3-hydroxyazetidine-1-carbonyl)-2-methylphenyl)quinoline-8-sulfonamide

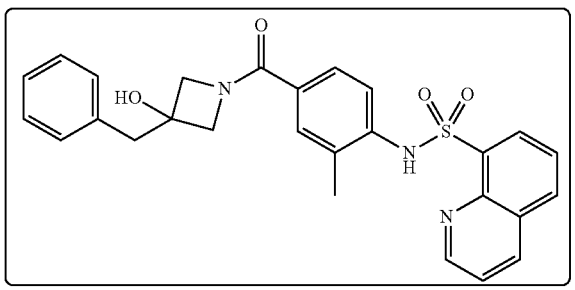 [SMILES: Cc1cc(C(=O)N2CC(O)(Cc3ccccc3)C2)ccc1NS(=O)(=O)c1cccc2cccnc12]

$^1$H NMR (400 MHz, DMSOd$_6$) δ: 2.1 (s, 3H), 2.2 (s, 2H), 2.6 (s, 2H), 2.7 (s, 2H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 96.9%; MS: m/z 488.1 (M+1)$^+$.

Compound 130

N-(4-(3-benzyl-3-hydroxyazetidine-1-carbonyl)-3-methoxyphenyl)quinoline-8-sulfonamide

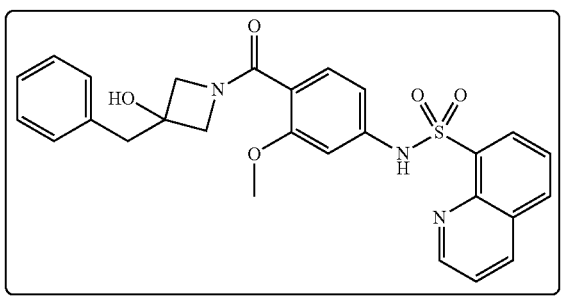 [SMILES: COc1cc(NS(=O)(=O)c2cccc3cccnc23)ccc1C(=O)N1CC(O)(Cc2ccccc2)C1]

$^1$H NMR (400 MHz, DMSOd$_6$) δ: 2.2 (s, 2H), 2.6 (s, 2H), 2.7 (s, 2H), 3.9 (s, 3H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 96.9%; MS: m/z 504.2 (M+1)$^+$.

Example 2

Synthesis of Compounds of Formula II Wherein $R^{1a}$ is H and $R^{1b}$ is —N(CH$_3$)-Benzyl or —NH-Benzyl Compounds of Formula II wherein $R^{1a}$ is H and $R^{1b}$ is —N(CH$_3$)-benzyl or —NH-benzyl are produced according to Scheme 2:

Scheme 2:

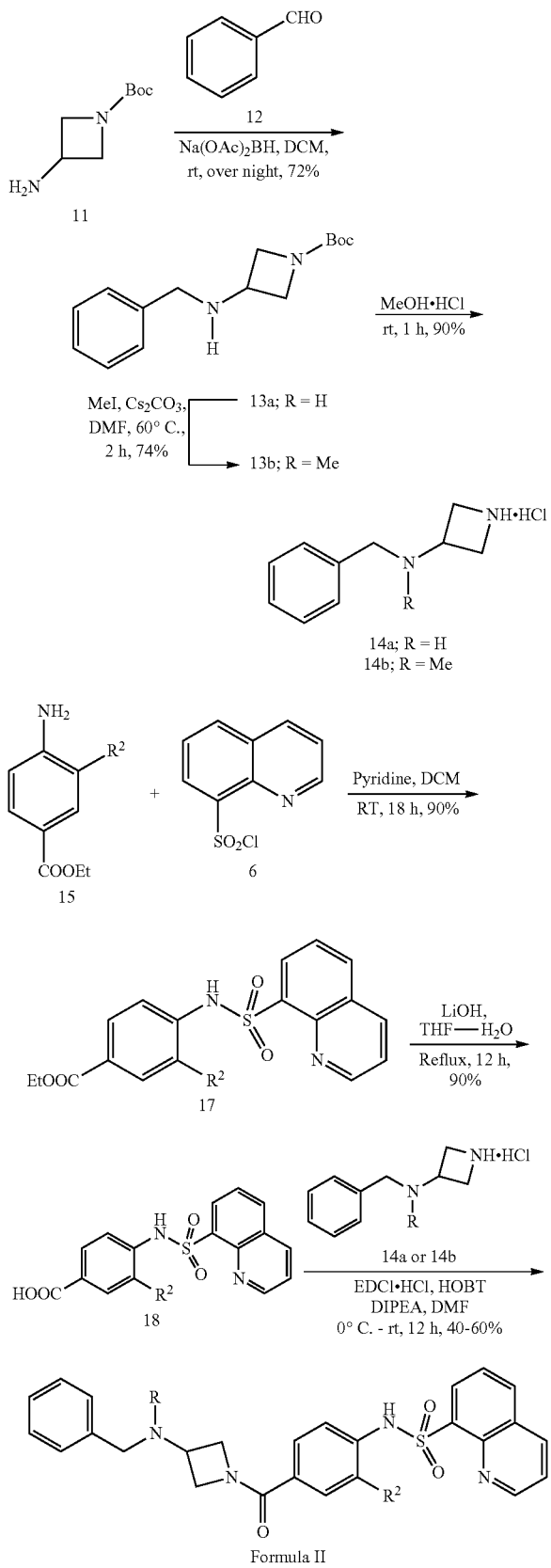

Procedure for preparation of tert-butyl 3-(benzylamino)azetidine-1-carboxylate (13a)

1-Boc-3-aminoazetidine (11) (2.2 gm, 12.78 mmol) was dissolved in DCM (20 ml) under nitrogen and cooled to 0° C. Then the solution was added benzaldehyde (12; 1.35 gm, 12.78 mmol) followed by sodium triacetoxyborohydride (8.13 gm, 38.34 mmol) under nitrogen atmosphere. The reaction mixture was then allowed to warm to room temperature and stirred over night. The reaction's completion was monitored by TLC. After completion of the reaction it was quenched by the addition of water (5 ml) and extracted with DCM. The organic layer was washed with brine (10 ml), dried over anhydrous sodium sulfate, filtered and concentrated under vacuum. Crude product was then purified by column chromatography to give compound (13a) (2.46 gm, 72%). $^1$H NMR (400 MHz, CDCl$_3$) δ: 1.40 (s, 9H), 3.60 (m, 3H), 3.73 (s, 2H), 4.05 (m, 2H), 7.3 (m, 5H); MS: m/z 263.20 (M+1)$^+$.

Procedure for preparation of tert-butyl 3-(benzyl(methyl)amino)azetidine-1-carboxylate (13b)

A solution of tert-butyl 3-(benzylamino)azetidine-1-carboxylate (13a) (0.55 gm, 2.09 mmol) in DMF was added methyl iodide (0.26 ml, 4.18 mmol) and cesium carbonate (1.36 gm, 4.18 mmol). The resultant reaction mixture was then warmed to 60° C. and stirred for 2 h. The reaction mixture was then diluted with ethyl acetate (100 ml), washed with water (3×25 ml), brine, dried over sodium sulfate and concentrated under vacuum. The crude product was purified by column chromatography to give compound (13b) (2.46 gm, 72%). $^1$H NMR (400 MHz, CDCl$_3$) δ: 1.40 (s, 9H), 3.40 (m, 5H), 4.00 (m, 2H), 4.20 (m, 2H), 5.2 (m, 1H), 7.50 (m, 3H), 7.70 (d, 2H); MS: m/z 277.10 (M+1)$^+$.

General Procedure for N-Boc Deprotection (14a & 14b)

Amine (13a or 13b) (2.0 gm) was taken into a round bottomed flask and was added methanolic-HCl (25 mL, 20%) and was stirred for 1 h at room temperature. After completion of the reaction (monitored by TLC), the solvent was removed under vacuum to get a white solid as a crude product. The crude product was washed with ethyl acetate repeatedly and then dried well to obtain compound 14a or 14b, respectively as a white solid (90%) and was used further without purification.

General Procedure for Preparation of Compound 17

To stirred a solution of amine 15 (30.16 mmol) in a 1:1 mixture of DCM-pyridine (50+50 ml) was added quinoline-8-sulfonyl chloride (6) (8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 mL), 1N HCl solution (3×50 ml) and brine (50 ml). The organic extracts were dried over anhydrous sodium sulfate, filtered and concentrated under vacuum to obtain the crude product. Crude product was co-distilled with toluene to remove the remnants of pyridine and dried to get ester 17 (70-90%) as an off-white solid. This product was used as such for the next step without further purification.

General Procedure for Preparation of Compound 18

A stirred solution of ester 17 (10.05 mmol) in a mixture of THF-water (50+50 ml) was added LiOH (2.11 g, 50.25 mmol) and the resultant solution was refluxed overnight. After completion of the reaction (monitored by TLC), the reaction mixture was extracted with ethyl acetate (3×50 ml) and then acidified with dilute HCl. The resultant suspension was filtered and residue was co-distilled with toluene. The product was then dried under vacuum to get carboxylic acid 18 (70-80%) as an off-white solid.

General Procedure for Compounds of Formula II Wherein $R^{1a}$ is H and $R^{1b}$ is —N(CH$_3$)-Benzyl or —NH-Benzyl To a stirred solution of the carboxylic acid 18 (0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine hydrochloride 14a or 14b) (0.61 mmol) was then added at 0° C. and stirred overnight at room temperature. After completion of the reaction (monitored by TLC), the reaction mixture was poured into 1.0 M HCl and extracted with EtOAc. The organic layer was washed with sat. aq. NaHCO$_3$, dried over NaSO$_4$ and filtered. The solvent was removed by rotary evaporation and the product was isolated by chromatography on silica gel (60-120 silica gel, 2% MeOH-DCM) or preparative HPLC to yield final compound (50-60%) as an off-white solid.

Compound 147

N-(4-(3-(benzylamino)azetidine-1-carbonyl)phenyl)quinoline-8-sulfonamide

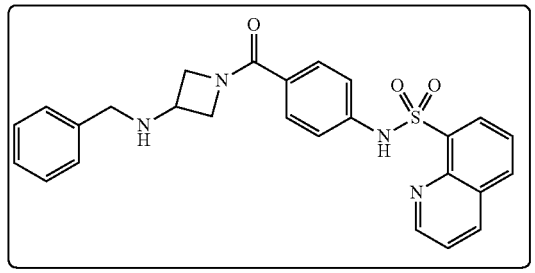 [SMILES: O=C(c1ccc(NS(=O)(=O)c2cccc3cccnc23)cc1)N1CC(NCc2ccccc2)C1]

$^1$H NMR (400 MHz, DMSOd$_6$) δ: 1.8-1.85 (m, 1H), 2.2 (dd, 2H), 2.6 (dd, 2H), 2.7 (s, 2H), 7.16-7.4 (m, 5H), 7.37-7.57 (m, 4H), 7.79-7.84 (m, 2H), 8.2-8.40 (m, 2H), 9.10 (d, 1H), 10.4 (s, 1H); HPLC purity: 96.9%; MS: m/z 473.1 (M+1)$^+$.

Compound 109

N-(4-(3-(benzyl(methyl)amino)azetidine-1-carbonyl)-2-methylphenyl)quinoline-8-sulfonamide

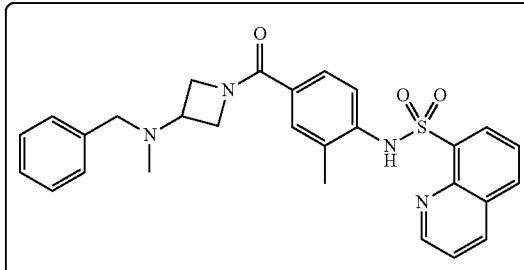

$^1$H NMR (400 MHz, DMSOd$_6$) δ: 1.8-1.85 (m, 1H), 2.1 (s, 3H), 2.2 (dd, 2H), 2.6 (dd, 2H), 2.7 (s, 2H), 3.1 (s, 3H), 7.16-7.4 (m, 5H), 7.37-7.57 (m, 3H), 7.79-7.84 (m, 2H), 8.2-8.40 (m, 2H), 9.10 (d, 1H), 10.4 (s, 1H); HPLC purity: 96.9%; MS: m/z 488.1 (M+1)$^+$.

Example 3

Synthesis of Compounds of Formula II Wherein $R^{1a}$ is Hydrogen and $R^{1b}$ is —O-Benzyl Compounds of Formula II wherein $R^{1a}$ is hydrogen and $R^{1b}$ is —O-benzyl are prepared according to Scheme 3:

Scheme 3:

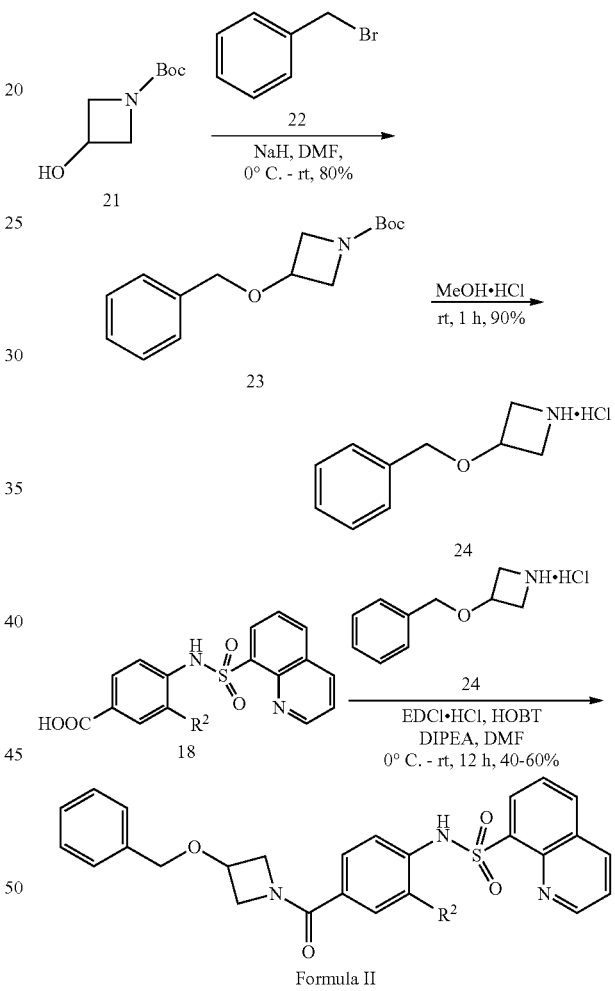

Procedure for preparation of tert-butyl 3-(benzyloxy)azetidine-1-carboxylate (23)

tert-butyl 3-hydroxyazetidine-1-carboxylate (21) (1 gm, 5.77 mmol) was dissolved in dry DMF (15 ml) and was cooled to 0° C. under nitrogen and was added sodium hydride (0.35 gm, 8.66 mmol). The reaction mixture was allowed to stir at room temperature for 30 min and was added benzylbromide (22; 1.08 gm, 6.35 mmol) at 0° C. The reaction mixture was then allowed warm to room temperature and stirred for 2 h. After completion of the reaction it was quenched by the addition of sat. ammonium chloride solution and extracted with ether. The organic layer was then dried over sodium sulfate and concentrated under vacuum. The crude product was purified column chromatography to yield compound 23 (1.21 gm, 80%).

$^1$H NMR ((400 MHz, DMSOd$_6$) δ: 1.4 (s, 9H), 3.65 (m, 2H), 4.00 (t, 2H), 4.30 (m, 1H), 4.40 (s, 2H), 7.35 (m, 5H); MS: m/z 264.20 (M+1)$^+$.

Procedure for preparation of 3-(benzyloxy)azetidine hydrochloride 24 tert-butyl 3-(benzyloxy)azetidine-1-carboxylate 23 (1.0 μm) was taken into a round bottomed flask and was added methanolic-HCl (15 mL, 20%) and was stirred for 1 h at room temperature. After completion of the reaction (monitored by TLC), the solvent was removed under vacuum to get a white solid as a crude product. The crude product was washed with ethyl acetate repeatedly and then dried well to obtain compound 24 as a white solid (92%) and was used further without purification.

General Procedure for Compound of Formula II Wherein R$^{1a}$ is Hydrogen and R$^{1b}$ is —O-benzyl To a stirred solution of the carboxylic acid 18 (0.61 mmol) (prepared as in Example 2) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine hydrochloride 24 (0.61 mmol) was then added at 0° C. and stirred overnight at room temperature. After completion of the reaction (monitored by TLC), the reaction mixture was poured into 1.0 M HCl and extracted with EtOAc. The organic layer was washed with sat. aq. NaHCO$_3$, dried over NaSO$_4$ and filtered. The solvent was removed by rotary evaporation and the product was isolated by chromatography on silica gel (60-120 silica gel, 2% MeOH-DCM) or preparative HPLC to yield final compound (50-60%) as an off-white solid.

Compound 108

N-(4-(3-(benzyloxy)azetidine-1-carbonyl)phenyl)quinoline-8-sulfonamide

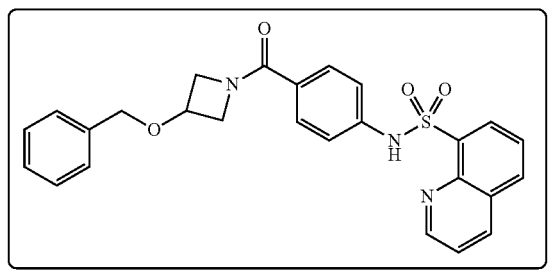 [SMILES: O=C(c1ccc(NS(=O)(=O)c2cccc3cccnc23)cc1)N1CC(OCc2ccccc2)C1]

$^1$H NMR (400 MHz, DMSOd$_6$) δ: 2.6 (s, 2H), 2.2 (dd, 2H), 4.1-4.2 (dd, 3H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 98.9%; MS: m/z 474.1 (M+1)$^+$.

Compound 120

N-(4-(3-(benzyloxy)azetidine-1-carbonyl)-2-methylphenyl)quinoline-8-sulfonamide

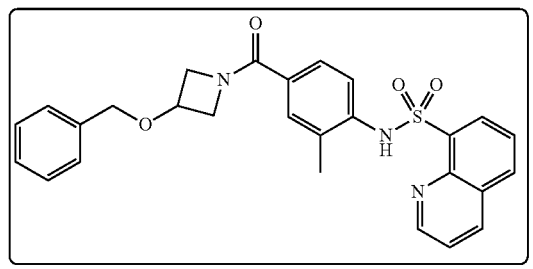 [SMILES: Cc1cc(C(=O)N2CC(OCc3ccccc3)C2)ccc1NS(=O)(=O)c1cccc2cccnc12]

$^1$H NMR (400 MHz, DMSOd$_6$) δ: 2.2 (s, 3H), 2.6 (s, 2H), 2.2 (dd, 2H), 4.1-4.2 (dd, 3H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 98.5%; MS: m/z 488.3 (M+1)$^+$.

Example 4

Syntheses of Compounds of Formula II Wherein R$^{1a}$ is Hydrogen and R$^{1b}$ is —NH—C(O)—R$^a$ Compounds of Formula II wherein R$^{1a}$ is Hydrogen and R$^{1b}$ is —NH—C(O)—Ar are prepared as set forth in Scheme 4:

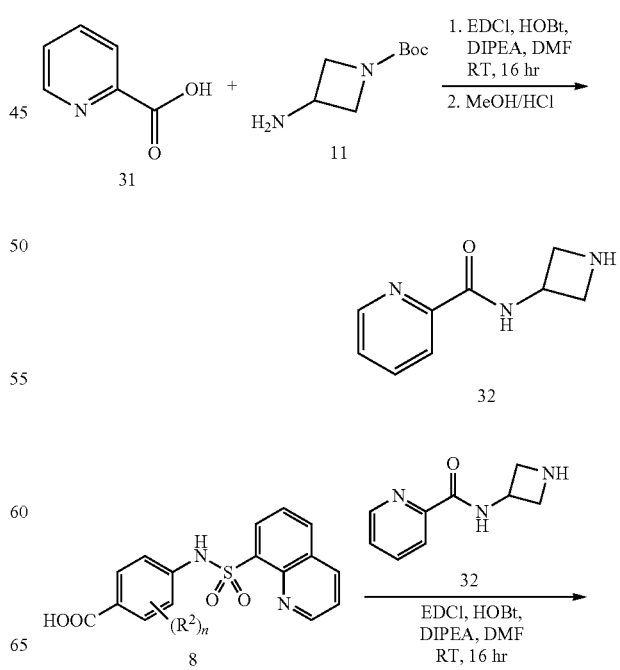

-continued

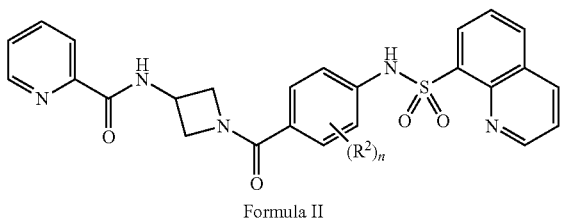

Formula II

General Procedure for the Synthesis of Urea 32

EDCI (3.8 g, 19.8 mmol) and HOBT (2.67 g, 19.8 mmol) were added to a stirred solution of the acid 31 (19.8 mmol) in anhydrous DMF. The temperature of the mixture was reduced to 0° C., at which time DIPEA (11 ml, 59.45 mmol) was added under nitrogen atmosphere and the resultant solution (or suspension) was stirred at room temperature for 30 min. 3-amino-1-Boc azetidine (11; 19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-32 (81%; not shown) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried with anhydrous Na$_2$SO$_4$ and the solvent removed under low pressure to get the free amine 32 as off white solid (95%).

General Procedure for the Synthesis of Amides 22a-c

EDCI (48 mg, 0.2525 mmol) and HOBT (34 mg, 0.2525 mmol) were added to a stirred solution of 8 (0.2525 mmol; prepared as in Example 1) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min. Amine 32 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 45-65% yields.

Compound 103

N-(1-(3-Methyl-4-(quinoline-8-sulfonamido)benzoyl)azetidin-3-yl)picolinamide

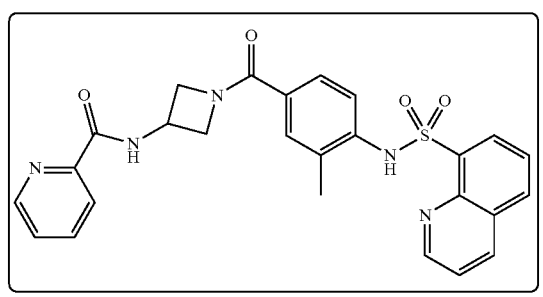 [SMILES: Cc1cc(C(=O)N2CC(NC(=O)c3ccccn3)C2)ccc1NS(=O)(=O)c1cccc2cccnc12]

$^1$H NMR (400 MHz, CDCl$_3$) δ: 2.1 (s, 3H), 4.2 (d, 2H), 4.4 (d, 2H), 5.2 (m, 1H), 7.0-8.0 (m, 8H), 8.0-8.4 (m, 4H), 9.1 (m, 1H); HPLC Purity: 97.5%; LCMS, m/z found 502.1 (M+1)$^+$.

Compound 111

N-(1-(4-(Quinoline-8-sulfonamido)benzoyl)azetidin-3-yl)picolinamide

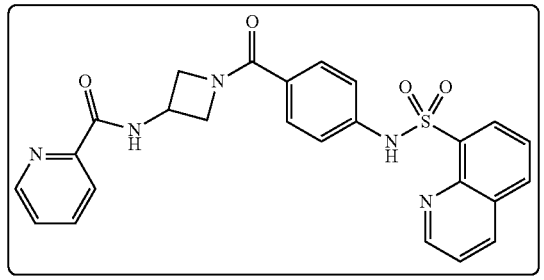 [SMILES: O=C(NC1CN(C(=O)c2ccc(NS(=O)(=O)c3cccc4cccnc34)cc2)C1)c1ccccn1]

$^1$H NMR (400 MHz, CDCl$_3$) δ: 4.2 (d, 2H), 4.4 (d, 2H), 5.2 (m, 1H), 7.0-8.0 (m, 8H), 8.0-8.4 (m, 5H), 9.1 (m, 1H); HPLC Purity: 98.6%; LCMS, m/z found 488.2 (M+1)$^+$.

Compound 121

N-(1-(3-Fluoro-4-(quinoline-8-sulfonamido)benzoyl)azetidin-3-yl)picolinamide (22c)

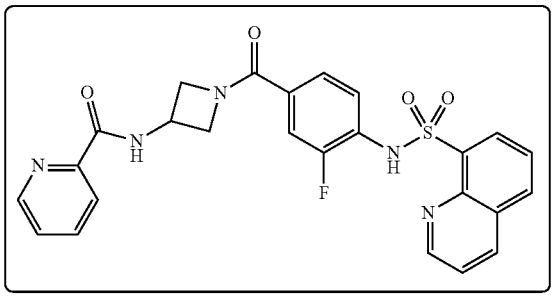 [SMILES: O=C(NC1CN(C(=O)c2ccc(NS(=O)(=O)c3cccc4cccnc34)c(F)c2)C1)c1ccccn1]

$^1$H NMR (400 MHz, CDCl$_3$) δ: 4.2 (d, 2H), 4.4 (d, 2H), 5.2 (m, 1H), 7.0-8.0 (m, 8H), 8.0-8.4 (m, 4H), 9.1 (m, 1H); HPLC Purity: 99.0%; LCMS, m/z found 506.3 (M+1)$^+$.

Example 5

Syntheses of Compounds of Formula II, Wherein R$^{1a}$ is Hydrogen and R$^{1b}$ is —NH—C(O)—NH—R$^a$ Compounds of Formula II, wherein R$^{1a}$ is hydrogen and R$^{1b}$ is —NH—C(O)—NH—R$^a$ are prepared according to Scheme 5:

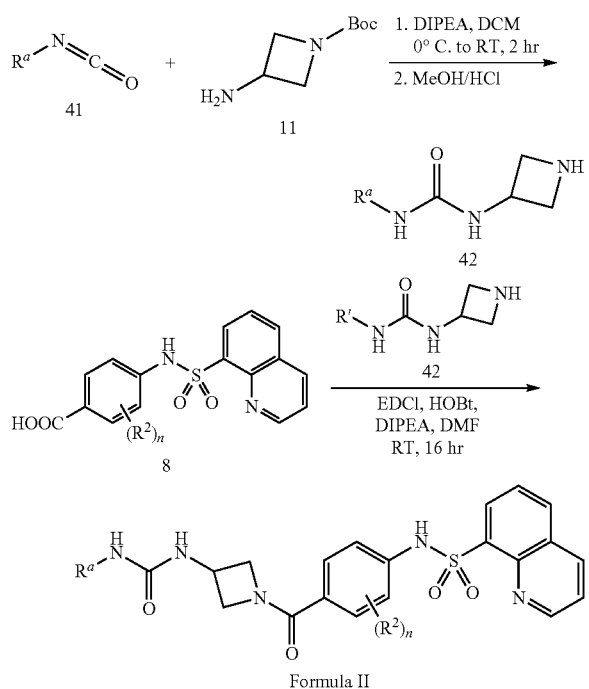

Formula II

General Procedure for the Synthesis of Urea 42

To a stirred solution of 3-amino-1-Boc azetidine (11; 100 mg, 0.5813 mmol) and DIPEA (160 mg, 0.8719 mmol) in DCM (2 ml) at 0° C. was slowly added isocyanate 41. The resulting mixture was stirred for 2 hr at RT. After completion of the reaction, the reaction mixture was dilute with water and the product was extracted in DCM (2×20 ml). The organic layer was washed with water (2×15 ml), dried over anhydrous sodium sulfate, filtered and concentrated over the rotary evaporator to get the crude product. Crude product was purified by column chromatography (60-120 silica gel, 2% MeOH-DCM) to get pure product, Boc-42 (59%; not shown) as an off-white solid, which was subjected to the treatment with methanolic HCl (10 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried over anhydrous Na$_2$SO$_4$ and the solvent removed under low pressure to get the free amine 42 as off white solid (87%).

General Procedure for the Synthesis of Compounds of Formula II, Wherein R$^{1a}$ is Hydrogen and R$^{1b}$ is —NH—C(O)—NH—R$^a$ EDCI (48 mg, 0.2525 mmol) and HOBT (34 mg, 0.2525 mmol) were added to a stirred solution of 8 (0.2525 mmol; prepared as in Example 1) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min. Amine 42 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 53-63% yields.

Compound 139

N-(4-(3-(3-Allylureido)azetidine-1-carbonyl)phenyl)quinoline-8-sulfonamide

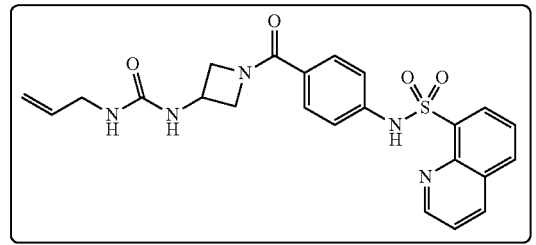 [SMILES: C=CCNC(=O)NC1CN(C(=O)c2ccc(NS(=O)(=O)c3cccc4cccnc34)cc2)C1]

$^1$H NMR (400 MHz, CDCl$_3$) δ: 4.2 (d, 2H), 4.3 (s, 2H), 4.4 (d, 2H), 5.0 (m, 1H), 5.2 (m, 2H), 5.9 (m, 1H), 7.0-8.0 (m, 5H), 8.0-8.4 (m, 4H), 9.1 (m, 1H); HPLC Purity: 97.8%; LCMS, m/z found 484.3 (M+1)$^+$.

Compound 140

N-(4-(3-(3-Allylureido)azetidine-1-carbonyl)-2-methoxyphenyl)quinoline-8-sulfonamide

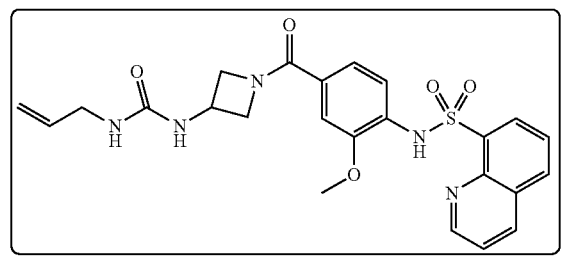 [SMILES: C=CCNC(=O)NC1CN(C(=O)c2ccc(NS(=O)(=O)c3cccc4cccnc34)c(OC)c2)C1]

$^1$H NMR (400 MHz, CDCl$_3$) δ: 3.9 (s, 3H), 4.2 (d, 2H), 4.3 (s, 2H), 4.4 (d, 2H), 5.0 (m, 1H), 5.2 (m, 2H), 5.9 (m, 1H), 7.0-8.0 (m, 4H), 8.0-8.4 (m, 4H), 9.1 (m, 1H); HPLC Purity: 99.1%; LCMS, m/z found 496.2 (M+1)⁺.

Compound 166

N-(4-(3-(3-Allylureido)azetidine-1-carbonyl)-2-methylphenyl)quinoline-8-sulfonamide

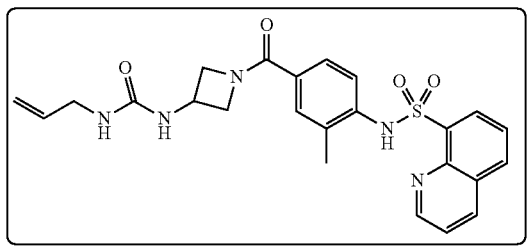 [SMILES: C=CCNC(=O)NC1CN(C(=O)c2ccc(NS(=O)(=O)c3cccc4cccnc34)c(C)c2)C1]

¹H NMR (400 MHz, CDCl₃) δ: 2.1 (s, 3H), 4.2 (d, 2H), 4.3 (s, 2H), 4.4 (d, 2H), 5.0 (m, 1H), 5.2 (m, 2H), 5.9 (m, 1H), 7.0-8.0 (m, 4H), 8.0-8.4 (m, 4H), 9.1 (m, 1H); HPLC Purity: 98.6%; LCMS, m/z found 480.3 (M+1)⁺.

Compound 160

N-(4-(3-(3-(Pyridin-2-yl)ureido)azetidine-1-carbonyl)phenyl)quinoline-8-sulfonamide

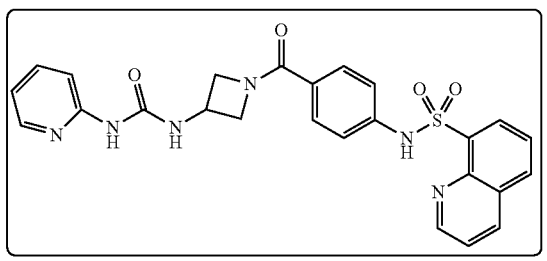 [SMILES: O=C(Nc1ccccn1)NC1CN(C(=O)c2ccc(NS(=O)(=O)c3cccc4cccnc34)cc2)C1]

¹H NMR (400 MHz, CDCl₃) δ: 4.2 (d, 2H), 4.4 (d, 2H), 5.2 (m, 1H), 7.0-8.0 (m, 8H), 8.0-8.2 (m, 5H), 9.1 (m, 1H); HPLC Purity: 99.2%; LCMS, m/z found 503.1 (M+1)⁺.

Example 6

Syntheses of Compounds of Formula II Wherein $R^{1a}$ is Hydrogen and $R^{1b}$ is —O—C(O)—$R^a$ Compounds of Formula II wherein $R^{1a}$ is hydrogen and $R^{1b}$ is —O—C(O)—$R^a$ are prepared according to Scheme 6.

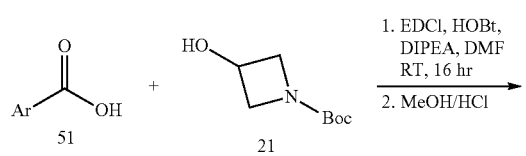

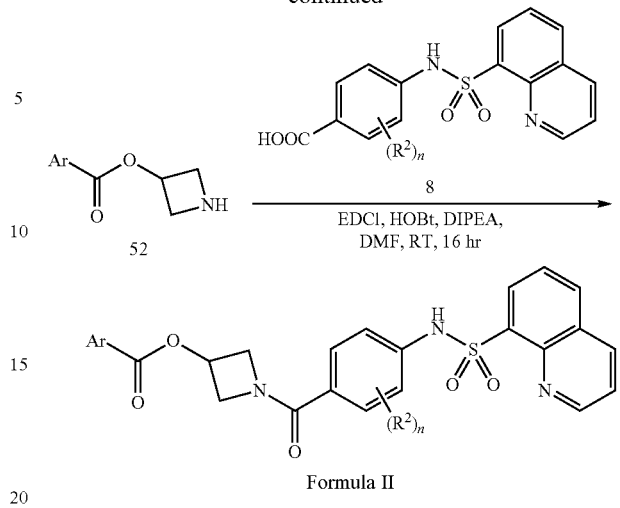

Formula II

General Procedure for the Synthesis of Ester 52

EDCI (48 mg, 0.2525 mmol) and HOBT (34 mg, 0.2525 mmol) were added to a stirred solution of the Ar—COOH (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min. 3-Hydroxy-1-Boc azetidine 21 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get crude product. The crude product was purified by column chromatography (60-120 silica gel, 2% MeOH-DCM) to get pure product, Boc-52 (66%; not shown) as an off-white solid, which was subjected to the treatment with methanolic HCl (10 ml) for 2 hr at RT. After the complete cleavage of Boc-group, the solvent was removed under low pressure, to give the crude product as an HCl salt. The aqueous solution of the salt was washed with diethylether and basified with NaHCO₃ (pH 10). The desired product was then partitioned into ethyl acetate, dried over anhydrous Na₂SO₄ and the solvent removed under low pressure to get the free amine 52 as off white solid (83%).

General Procedure for the Synthesis of Compounds of Formula II Wherein $R^{1a}$ is Hydrogen and $R^{1b}$ is —O—C(O)—$R^a$ EDCI (48 mg, 0.2525 mmol) and HOBT (34 mg, 0.2525 mmol) were added to a stirred solution of the carboxylic acid 8 (0.2525 mmol; prepared as in Example 1) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min. Amine 52 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get crude product. Crude product was purified by either by silica column chromatography or preparative HPLC to obtain the pure products in 47-68% yields.

Compound 102

1-(4-(Quinoline-8-sulfonamido)benzoyl)azetidin-3-yl picolinate

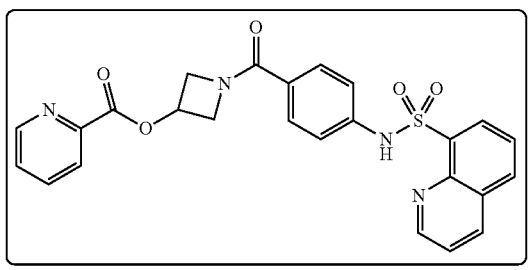 [SMILES: O=C(OC1CN(C(=O)c2ccc(NS(=O)(=O)c3cccc4cccnc34)cc2)C1)c1ccccn1]

$^1$H NMR (400 MHz, CDCl$_3$) δ: 4.2-4.8 (m, 4H), 5.5 (m, 1H), 7.2-7.7 (m, 7H), 8.0-8.7 (m, 6H), 9.1 (m, 1H); HPLC Purity: 91.0%; LCMS, m/z found 489.3 (M+1)$^+$.

Compound 110

1-(3-Methyl-4-(quinoline-8-sulfonamido)benzoyl)azetidin-3-yl picolinate

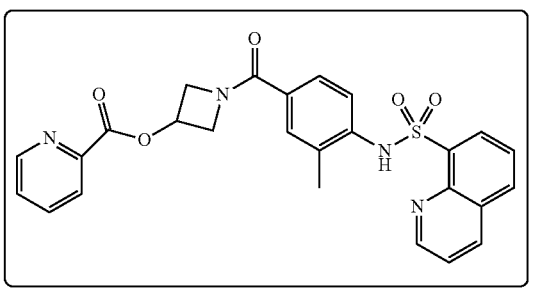 [SMILES: Cc1cc(C(=O)N2CC(OC(=O)c3ccccn3)C2)ccc1NS(=O)(=O)c1cccc2cccnc12]

$^1$H NMR (400 MHz, CDCl$_3$) δ: 2.1 (s, 3H), 4.2-4.8 (m, 4H), 5.5 (m, 1H), 7.2-7.7 (m, 6H), 8.0-8.7 (m, 6H), 9.1 (m, 1H); HPLC Purity: 98.4%; LCMS, m/z found 503.1 (M+1)$^+$.

Compound 123

1-(4-(Quinoline-8-sulfonamido)benzoyl)azetidin-3-yl 2-phenylacetate

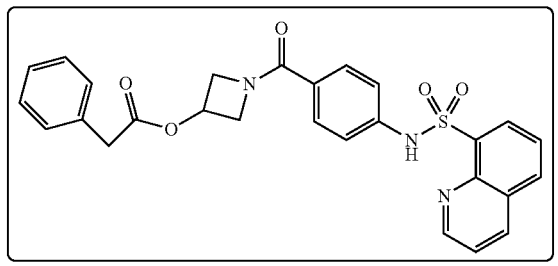 [SMILES: O=C(Cc1ccccc1)OC1CN(C(=O)c2ccc(NS(=O)(=O)c3cccc4cccnc34)cc2)C1]

$^1$H NMR (400 MHz, CDCl$_3$) δ: 3.6 (m, 1H), 4.2 (d, 2H), 4.4-4.6 (d, 2H), 5.3 (m, 2H), 7.2-7.8 (m, 7H), 8.0-8.7 (m, 7H), 9.1 (m, 1H); HPLC Purity: 97.0%; LCMS, m/z found 502.2 (M+1)$^+$.

Compound 124

1-(3-Fluoro-4-(quinoline-8-sulfonamido)benzoyl)azetidin-3-yl picolinate

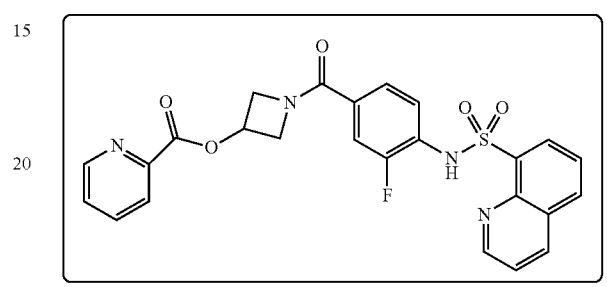

$^1$H NMR (400 MHz, CDCl$_3$) δ: 4.2 (d, 2H), 4.6 (d, 2H), 4.7 (m, 1H), 7.2-7.8 (m, 6H), 8.0-8.7 (m, 6H), 9.1 (m, 1H); HPLC Purity: 99.0%; LCMS, m/z found 507.4 (M+1)$^+$.

Example 7

Syntheses of Compounds of Formula II Wherein R$^{1a}$ is Hydrogen and R$^{1b}$ is —O—C(O)—NH—R$^a$ Compounds of Formula II wherein R$^{1a}$ is hydrogen and R$^{1b}$ is —O—C(O)—NH—R$^a$ are prepared according to Scheme 7.

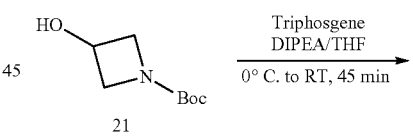

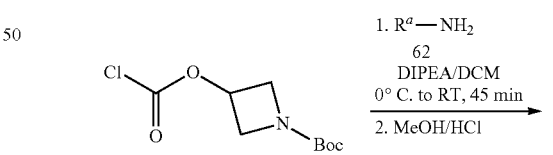

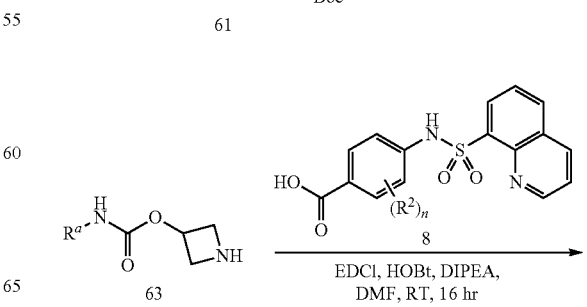

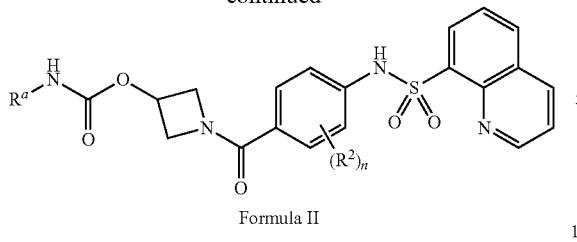

Formula II tert-Butyl 3-((chlorocarbonyl)oxy)azetidine-1-carboxylate 61

To a stirred solution of 3-hydroxy-1-Boc azetidine (21; 350 mg, 2.023 mmol) and DIPEA (1.3 ml, 7.080 mmol) in THF (5 ml) at 0° C. was slowly added triphosgene (898 mg, 3.034 mmol). The resulting mixture was stirred for 2 hr at RT. After completion of the reaction, the reaction mixture was filtered and washed with fresh THF to get rid of inorganic salts. The filtrate was concentrated under reduced pressure to get crude product 61 in 55% yield. The crude product, thus obtained, was immediately used for the next reaction.

General Procedure for the Synthesis of Carbamate 63

To a stirred solution of amine 62 (100 mg, 1.694 mmol) and DIPEA (0.47 ml, 2.541 mmol) in DCM (2 ml) at 0° C. was slowly added a solution of compound 61 (477 mg, 2.033 mmol) in DCM (1 ml). The resulting mixture was stirred for 2 hr at RT. After completion of the reaction, the reaction mixture was dilute with water and the product was extracted in DCM (2×20 ml). The organic layer was washed with water (2×15 ml), dried over anhydrous sodium sulfate, filtered and concentrated over the rotary evaporator to get the crude product. Crude product was purified by column chromatography (60-120 silica gel, 2% MeOH-DCM) to get pure product, Boc-63 (54%; not shown) as an off-white solid, which was subjected to the treatment with methanolic HCl (10 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried over anhydrous Na$_2$SO$_4$ and the solvent removed under low pressure to get the free amine 63 as off white solid (88%).

General Procedure for the Synthesis of Compounds of Formula II Wherein R$^{1a}$ is Hydrogen and R$^{1b}$ is —O—C(O)—NH—R$^a$ EDCI (58 mg, 0.3048 mmol) and HOBT (41 mg, 0.3048 mmol) were added to a stirred solution of the acid 8 (100 mg, 0.3048 mmol; prepared as in Example 1) in anhydrous DMF. The temperature of the mixture was reduced to 0° C., at which time DIPEA (196 µl, 1.067 mmol) was added under nitrogen atmosphere and the resultant solution (or suspension) was stirred at room temperature for 30 min. Amine 63 (0.3048 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 53-78% yields.

Compound 132

1-(3-Methyl-4-(quinoline-8-sulfonamido)benzoyl) azetidin-3-yl isopropylcarbamate

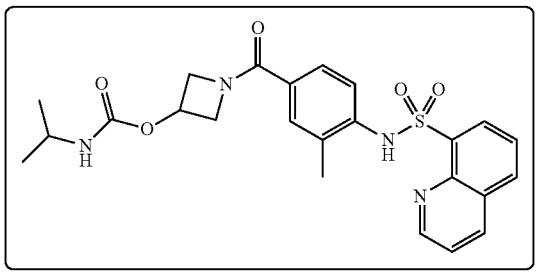 [SMILES: Cc1cc(C(=O)N2CC(OC(=O)NC(C)C)C2)ccc1NS(=O)(=O)c1cccc2cccnc12]

$^1$H NMR (400 MHz, CDCl$_3$) δ: 1.2 (s, 3H), 2.2 (d, 3H), 2.6 (d, 3H), 3.8 (m, 1H), 4.2 (d, 2H), 4.7 (d, 2H), 5.2 (m, 1H), 7.2-7.8 (m, 5H), 8.0-8.7 (m, 3H), 9.1 (m, 1H); HPLC Purity: 99.0%; LCMS, m/z found 483.1 (M+1)$^+$.

Compound 133

1-(2-Methoxy-4-(quinoline-8-sulfonamido)benzoyl) azetidin-3-yl isopropylcarbamate

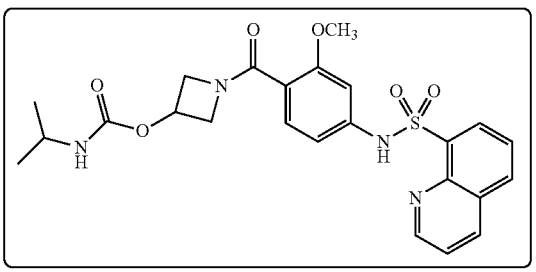 [SMILES: COc1cc(NS(=O)(=O)c2cccc3cccnc23)ccc1C(=O)N1CC(OC(=O)NC(C)C)C1]

$^1$H NMR (400 MHz, CDCl$_3$) δ: 1.6 (d, 6H), 3.9 (s, 3H), 4.2 (d, 2H), 4.7 (d, 2H), 5.2 (m, 1H), 6.3-7.0 (m, 3H), 7.6-8.4 (m, 5H), 9.1 (m, 1H); HPLC Purity: 99.7%; LCMS, m/z found 499.1 (M+1)$^+$.

Compound 134

1-(3-Fluoro-4-(quinoline-8-sulfonamido)benzoyl) azetidin-3-yl isopropylcarbamate

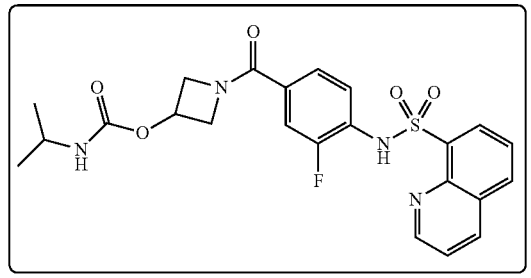 [SMILES: CC(C)NC(=O)OC1CN(C(=O)c2ccc(NS(=O)(=O)c3cccc4cccnc34)c(F)c2)C1]

¹H NMR (400 MHz, CDCl₃) δ: 1.4 (d, 6H), 3.7 (m, 1H), 3.8 (d, 2H), 4.2 (d, 2H), 5.2 (m, 1H), 7.0-7.6 (m, 5H), 8.0-8.4 (m, 3H), 9.1 (m, 1H); HPLC Purity: 98.6%; LCMS, m/z found 509 (M+Na)⁺.

Compound 135

1-(4-(Quinoline-8-sulfonamido)benzoyl)azetidin-3-yl isopropylcarbamate

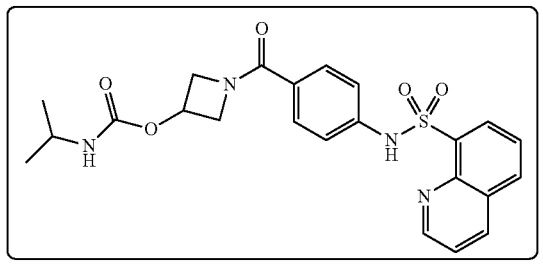 [SMILES: CC(C)NC(=O)OC1CN(C(=O)c2ccc(NS(=O)(=O)c3cccc4cccnc34)cc2)C1]

¹H NMR (400 MHz, CDCl₃) δ: 1.4 (d, 6H), 3.8 (m, 1H), 4.1 (d, 2H), 4.4 (d, 2H), 5.2 (m, 1H), 7.0-7.6 (m, 5H), 8.0-8.4 (m, 4H), 9.1 (m, 1H); HPLC Purity: 98.6%; LCMS, m/z found 469.2 (M+1)±.

Compound 155

1-(3-Methyl-4-(quinoline-8-sulfonamido)benzoyl)azetidin-3-yl pyridin-2-ylcarbamate

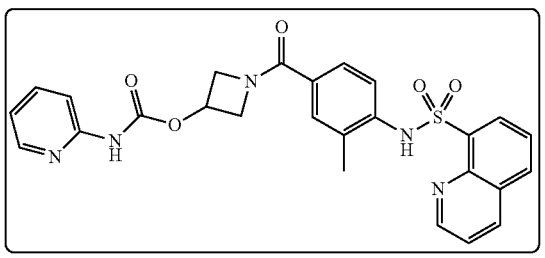 [SMILES: Cc1cc(C(=O)N2CC(OC(=O)Nc3ccccn3)C2)ccc1NS(=O)(=O)c1cccc2cccnc12]

¹H NMR (400 MHz, CDCl₃) δ: 2.1 (s, 3H), 3.8 (m, 1H), 4.1 (d, 2H), 4.4 (d, 2H), 5.2 (m, 1H), 7.0-7.6 (m, 7H), 8.0-8.4 (m, 5H), 9.1 (m, 1H); HPLC Purity: 96.1%; LCMS, m/z found 518.3 (M+1)±.

Compound 156

1-(3-Methoxy-4-(quinoline-8-sulfonamido)benzoyl)azetidin-3-ylpyridin-2-ylcarbamate (40f)

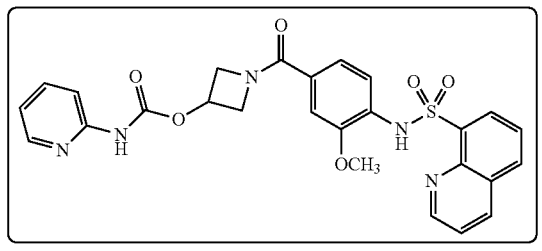 [SMILES: COc1cc(C(=O)N2CC(OC(=O)Nc3ccccn3)C2)ccc1NS(=O)(=O)c1cccc2cccnc12]

¹H NMR (400 MHz, CDCl₃) δ: 3.6 (s, 3H), 4.1 (d, 2H), 4.4 (d, 2H), 5.2 (m, 1H), 7.0-7.6 (m, 7H), 8.0-8.4 (m, 5H), 9.1 (m, 1H); HPLC Purity: 99.1%; LCMS, m/z found 534.3 (M+1)⁺.

Compound 157

1-(2-Methoxy-4-(quinoline-8-sulfonamido)benzoyl)azetidin-3-ylpyridin-2-ylcarbamate

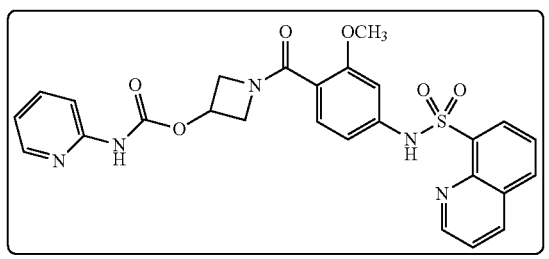 [SMILES: COc1cc(NS(=O)(=O)c2cccc3cccnc23)ccc1C(=O)N1CC(OC(=O)Nc2ccccn2)C1]

¹H NMR (400 MHz, CDCl₃) δ: 3.8 (s, 3H), 4.2 (d, 2H), 4.4 (d, 2H), 5.2 (m, 1H), 6.6-7.6 (m, 7H), 8.0-8.4 (m, 5H), 9.1 (m, 1H); HPLC Purity: 96.1%; LCMS, m/z found 534.3 (M+1)⁺.

Compound 161

1-(4-(Quinoline-8-sulfonamido)benzoyl)azetidin-3-ylpyridin-2-ylcarbamate

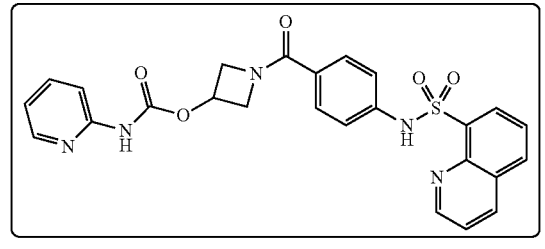 [SMILES: O=C(Nc1ccccn1)OC1CN(C(=O)c2ccc(NS(=O)(=O)c3cccc4cccnc34)cc2)C1]

¹H NMR (400 MHz, CDCl₃) δ: 4.2 (d, 2H), 4.4 (d, 2H), 5.2 (m, 1H), 7.0-8.0 (m, 9H), 8.0-8.4 (m, 4H), 9.1 (m, 1H); HPLC Purity: 98.3%; LCMS, m/z found 504.3 (M+1)±.

Compound 162

1-(3-Fluoro-4-(quinoline-8-sulfonamido)benzoyl)azetidin-3-ylpyridin-2-ylcarbamate

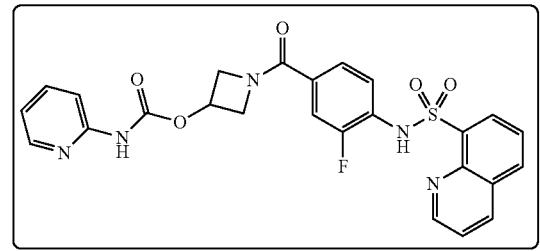 [SMILES: O=C(Nc1ccccn1)OC1CN(C(=O)c2ccc(NS(=O)(=O)c3cccc4cccnc34)c(F)c2)C1]

¹H NMR (400 MHz, CDCl₃) δ: 4.2 (d, 2H), 4.4 (d, 2H), 5.2 (m, 1H), 7.0-8.0 (m, 8H), 8.0-8.4 (m, 4H), 9.1 (m, 1H); HPLC Purity: 98.8%; LCMS, m/z found 522.3 (M+1)⁺.

Example 8

PKR Mutant Assay

Procedure:
PKR or PKR mutant enzyme solution was diluted in assay buffer.
2 μL of test compound was added into wells first, and then 180 μL reaction mix was added.
Reactions mixture with test compound was assembled except for ADP, and plates were stored for 60 minutes at room temperature.
20 uL ADP was added to start reaction at room temperature and reaction progress was measured as changes in absorbance at 340 nm wavelength at room temperature.

Test Compound Preparation:
Test compound stock was made at 100× concentration in 100% DMSO (10 mM)
1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)
1 to 100 dilution into assay (2 μl in 200 μl) yielded starting concentration of 100 μM, decreasing 3 fold for 11 points.

Assay Buffer:
100 mM KCl, 50 mM Tris 7.5, 5 mM MgCl2, 1 mM DTT, 0.03% BSA

Reaction Mixture:
PKR mutant enzyme: 80-400 ng/well; ADP: 0.22-1.65 mM; PEP: 0.1-0.5 mM; NADH: 180 uM; LDH: 0.5 units (Sigma#59023); DTT: 1 mM; BSA: 0.03%.

Example 9

PKR WT Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl₂, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:
PKR wt (100 ng/well), Tris pH 7.5 (50 mM), KCl (100 mM), MgCl₂ (5 mM), ADP (0.48 mM), PEP (0.15 mM), NADH (180 μM), LDH (0.5 units, Sigma 59023), DTT (1 mM) and BSA (0.03%).

Example 10

PKR R510Q Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl₂, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:
PKR R510Q (40 ng/well), Tris pH 7.5 (50 mM), KCl (100 mM), MgCl₂ (5 mM), ADP (0.2 mM), PEP (0.11 mM), NADH (180 μM), LDH (0.5 units, Sigma 59023), DTT (1 mM) and BSA (0.03%).

Example 11

PKR R532W Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl₂, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:
PKR R532W (100 ng/well), Tris pH 7.5 (50 mM), KCl (100 mM), MgCl2 (5 mM), ADP (0.36 mM), PEP (0.1 mM), NADH (180 μM), LDH (0.5 units, Sigma 59023), DTT (1 mM) and BSA (0.03%).

Example 12

PKR T384W Single Point Percent Activation Assay

A compound described herein was diluted with DMSO and tested at 1 μM concentration. The enzyme was diluted in 1× Buffer: (100 mM KCl, 50 mM Tris 7.5, 5 mM MgCl₂, 1 mM DTT, 0.03% BSA). 2 μL of compound solution was first added into wells, and then 180 μL enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:
PKR T384W soluble (300 ng/well), Tris pH 7.5 (50 mM), KCl (100 mM), MgCl2 (5 mM), ADP (0.08 mM), PEP (0.23 mM), NADH (180 μM), LDH (0.5 units, Sigma 59023), DTT (1 mM) and BSA (0.03%).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A method for increasing the lifetime of red blood cells (RBCs) in need thereof comprising contacting blood with an effective amount of (1) a compound of formula I or a pharmaceutically acceptable salt thereof; (2) a composition comprising a compound of formula I or a salt thereof, and a carrier or (3) a pharmaceutically acceptable composition comprising a compound of formula I or a pharmaceutically acceptable salt thereof, and a pharmaceutically acceptable carrier, wherein:

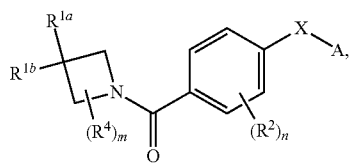

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

R$^{1a}$ is selected from hydrogen, alkyl, and arylalkyl; and R$^{1b}$ is selected from OR$^3$, N(alkyl)R$^3$ and NHR$^3$; or R$^{1a}$ is alken-1-yl and R$^{1b}$ is absent;

each R$^2$ is independently selected from halo, haloalkyl, alkyl, alkoxy and hydroxyl;

R$^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted;

each R$^4$ is independently selected from haloalkyl, alkyl, alkoxy and hydroxyl;

n is 0, 1, or 2; and m is 0, 1, or 2.

2. The method of claim 1, wherein the compound is added directly to whole blood or packed cells extracorporeally.

3. The method of claim 1, wherein the pharmaceutical composition is administered to a subject in need thereof.

4. A method for regulating 2,3-diphosphoglycerate levels in blood in need thereof comprising contacting blood with an effective amount of (1) a compound of formula I or a pharmaceutically acceptable salt thereof; (2) a composition comprising a compound of formula I or a salt thereof, and a carrier or (3) a pharmaceutically acceptable composition comprising a compound of formula I or a pharmaceutically acceptable salt thereof, and a pharmaceutically acceptable carrier, wherein:

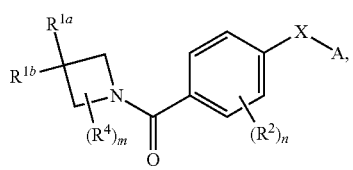

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

R$^{1a}$ is selected from hydrogen, alkyl, and arylalkyl; and R$^{1b}$ is selected from OR$^3$, N(alkyl)R$^3$ and NHR$^3$; or R$^{1a}$ is alken-1-yl and R$^{1b}$ is absent;

each R$^2$ is independently selected from halo, haloalkyl, alkyl, alkoxy and hydroxyl;

R$^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted;

each R$^4$ is independently selected from haloalkyl, alkyl, alkoxy and hydroxyl;

n is 0, 1, or 2; and m is 0, 1, or 2.

5. A method for treating hemolytic anemia comprising administering to a subject in need thereof a therapeutically effective amount of (1) a compound of formula I or a pharmaceutically acceptable salt thereof; or (2) a pharmaceutically acceptable composition comprising a compound of formula I or a pharmaceutically acceptable salt thereof, and a pharmaceutically acceptable carrier, wherein:

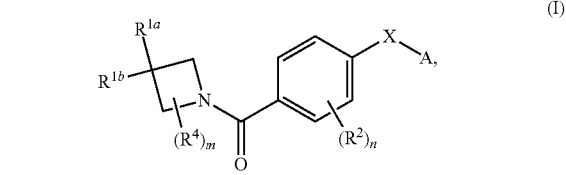

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

R$^{1a}$ is selected from hydrogen, alkyl, and arylalkyl; and R$^{1b}$ is selected from OR$^3$, N(alkyl)R$^3$ and NHR$^3$; or R$^{1a}$ is alken-1-yl and R$^{1b}$ is absent;

each R$^2$ is independently selected from halo, haloalkyl, alkyl, alkoxy and hydroxyl;

R$^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted;

each R$^4$ is independently selected from haloalkyl, alkyl, alkoxy and hydroxyl;

n is 0, 1, or 2; and m is 0, 1, or 2.

6. A method for treating sickle cell anemia comprising administering to a subject in need thereof a therapeutically effective amount of (1) a compound of formula I or a pharmaceutically acceptable salt thereof; or (2) a pharmaceutically acceptable composition comprising a compound of formula I or a pharmaceutically acceptable salt thereof, and a pharmaceutically acceptable carrier, wherein:

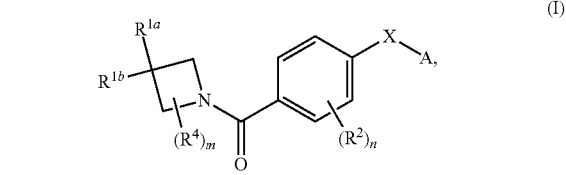

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)₂—, —N(alkyl)-S(O)₂—, —S(O)₂—N(H)—, and —S(O)₂—N(alkyl)-;

R$^{1a}$ is selected from hydrogen, alkyl, and arylalkyl; and R$^{1b}$ is selected from OR³, N(alkyl)R³ and NHR³; or R$^{1a}$ is alken-1-yl and R$^{1b}$ is absent;

each R² is independently selected from halo, haloalkyl, alkyl, alkoxy and hydroxyl;

R³ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted;

each R⁴ is independently selected from haloalkyl, alkyl, alkoxy and hydroxyl;

n is 0, 1, or 2; and m is 0, 1, or 2.

7. The method of claim 1, wherein m is 0, the compound having Formula (Ia):

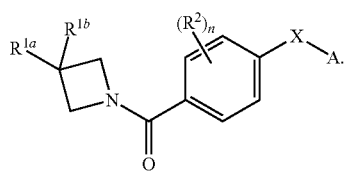

(Ia)

8. The method of claim 7, wherein A is a bicyclic heterocycle.

9. The method of claim 8, wherein A is quinolin-8-yl, and the compound is a compound having Formula II:

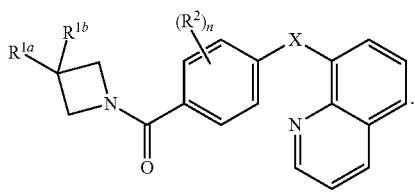

(II)

10. The method of claim 1, wherein R$^{1a}$ is selected from hydrogen, optionally substituted phenyl, methyl and optionally substituted benzyl.

11. The method of claim 1, wherein R$^{1b}$ is selected from hydroxyl, methoxy, optionally substituted benzoxy, optionally substituted —OC(O)-benzyl, optionally substituted —OC(O)-pyridinyl, —OC(O)NH(CH(CH₃)₂), optionally substituted —OC(O)NH(pyridinyl), —NH(optionally substituted phenyl), —N(CH₃)(optionally substituted phenyl), —NH(optionally substituted benzyl), —NH(optionally substituted pyridinyl), —NH(C(O)-pyridinyl), —NH(C(O)—NH—CH(CH₃)₂), and —NH(C(O)—NH—CH₂—CH=CH₂).

12. The method of claim 1, wherein n is 0, or where n is 1 R² is selected from fluoro, methyl, and methoxy.

13. The method of claim 9, wherein:

X is —NH—S(O)₂—;

R$^{1a}$ is phenyl or benzyl, wherein the ring portion of R$^{1a}$ is optionally substituted;

R$^{1b}$ is hydroxyl; and n is 0 or 1.

14. The method of claim 9, wherein:

X is —NH—S(O)₂—;

R$^{1a}$ is hydrogen;

R$^{1b}$ is selected from —NH-phenyl, phenoxy, —NH-pyridin-2-yl, and —N(CH₃)-phenyl, wherein the phenyl or pyridinyl portion of R$^{1b}$ is optionally substituted; and n is 0 or 1.

15. The method of claim 13, wherein n is 1 R² is selected from methyl and methoxy.

16. The method of claim 1, selected from any one of the compounds in the table below:

| Compound | Structure |
|---|---|
| 100 | 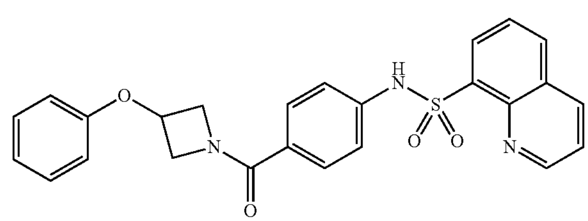 [SMILES: O=C(c1ccc(NS(=O)(=O)c2cccc3cccnc23)cc1)N1CC(Oc2ccccc2)C1] |

-continued

| Compound | Structure |
|---|---|
| 101 | 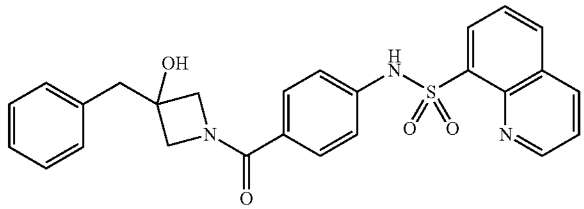 [SMILES: O=C(c1ccc(NS(=O)(=O)c2cccc3cccnc23)cc1)N1CC(O)(Cc2ccccc2)C1] |
| 102 | 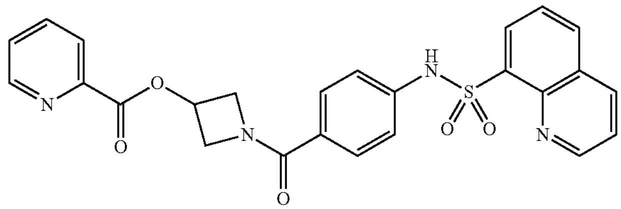 [SMILES: O=C(OC1CN(C(=O)c2ccc(NS(=O)(=O)c3cccc4cccnc34)cc2)C1)c1ccccn1] |
| 103 | 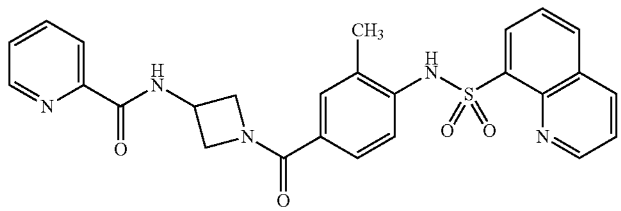 [SMILES: Cc1cc(C(=O)N2CC(NC(=O)c3ccccn3)C2)ccc1NS(=O)(=O)c1cccc2cccnc12] |
| 104 | 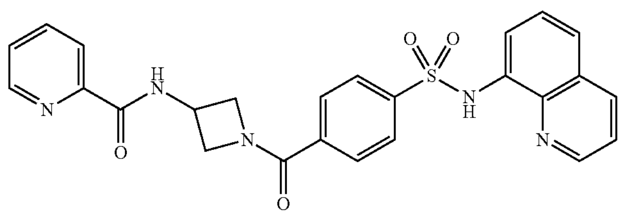 [SMILES: O=C(NC1CN(C(=O)c2ccc(S(=O)(=O)Nc3cccc4cccnc34)cc2)C1)c1ccccn1] |
| 105 | 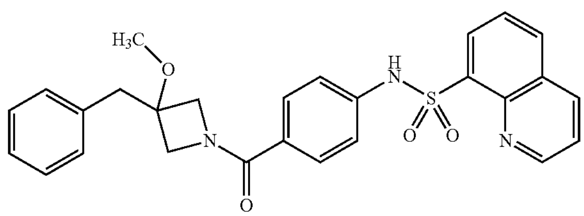 [SMILES: COC1(Cc2ccccc2)CN(C(=O)c2ccc(NS(=O)(=O)c3cccc4cccnc34)cc2)C1] |
| 106 | 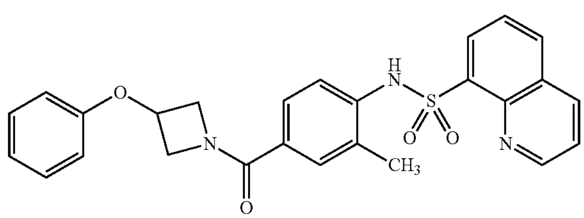 [SMILES: Cc1cc(C(=O)N2CC(Oc3ccccc3)C2)ccc1NS(=O)(=O)c1cccc2cccnc12] |
| 107 | 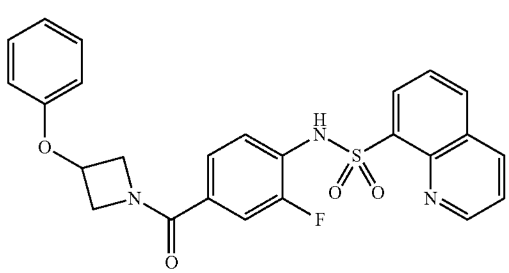 [SMILES: O=C(c1ccc(NS(=O)(=O)c2cccc3cccnc23)c(F)c1)N1CC(Oc2ccccc2)C1] |

-continued
| Compound | Structure |
|---|---|
| 108 | 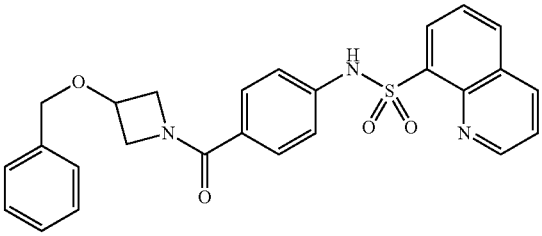 [SMILES: O=C(c1ccc(NS(=O)(=O)c2cccc3cccnc23)cc1)N1CC(OCc2ccccc2)C1] |
| 109 | 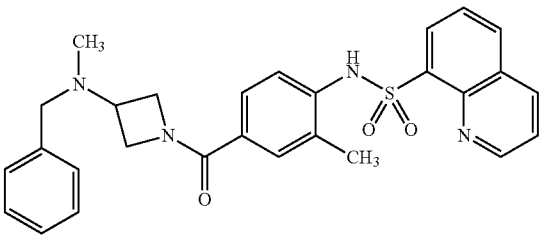 [SMILES: Cc1cc(C(=O)N2CC(N(C)Cc3ccccc3)C2)ccc1NS(=O)(=O)c1cccc2cccnc12] |
| 110 | 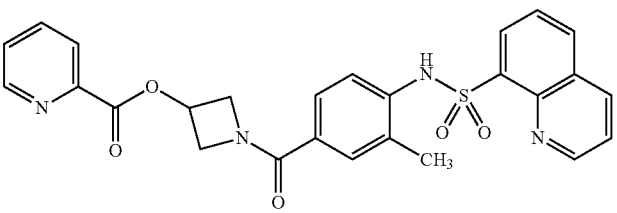 [SMILES: Cc1cc(C(=O)N2CC(OC(=O)c3ccccn3)C2)ccc1NS(=O)(=O)c1cccc2cccnc12] |
| 111 | 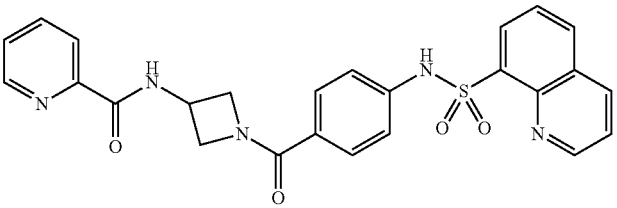 [SMILES: O=C(NC1CN(C(=O)c2ccc(NS(=O)(=O)c3cccc4cccnc34)cc2)C1)c1ccccn1] |
| 112 | 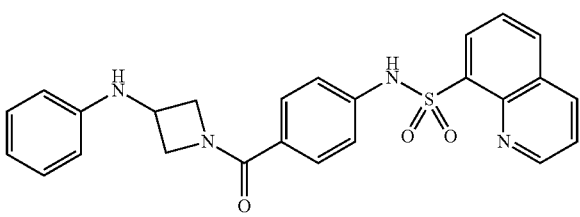 [SMILES: O=C(c1ccc(NS(=O)(=O)c2cccc3cccnc23)cc1)N1CC(Nc2ccccc2)C1] |
| 113 | 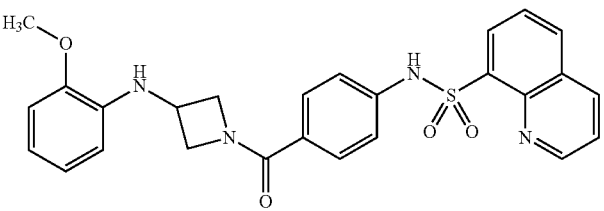 [SMILES: COc1ccccc1NC1CN(C(=O)c2ccc(NS(=O)(=O)c3cccc4cccnc34)cc2)C1] |
| 114 | 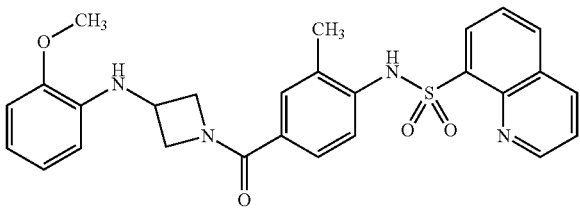 [SMILES: COc1ccccc1NC1CN(C(=O)c2ccc(NS(=O)(=O)c3cccc4cccnc34)c(C)c2)C1] |

-continued
| Compound | Structure |
|---|---|
| 115 | 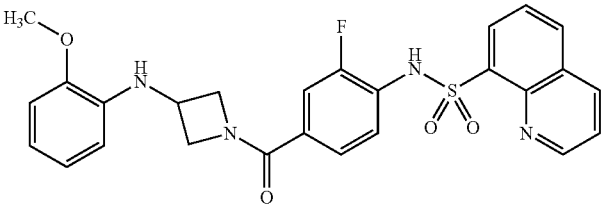 [SMILES: COc1ccccc1NC1CN(C(=O)c2ccc(NS(=O)(=O)c3cccc4cccnc34)c(F)c2)C1] |
| 116 | 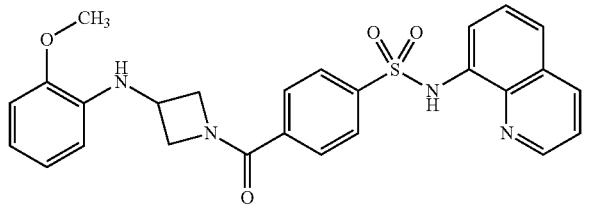 [SMILES: COc1ccccc1NC1CN(C(=O)c2ccc(S(=O)(=O)Nc3cccc4cccnc34)cc2)C1] |
| 117 | 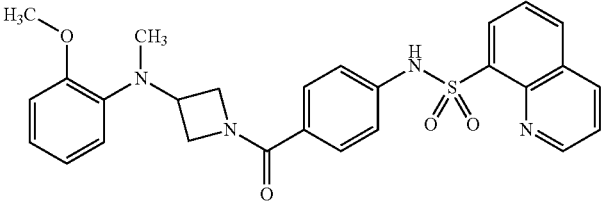 [SMILES: COc1ccccc1N(C)C1CN(C(=O)c2ccc(NS(=O)(=O)c3cccc4cccnc34)cc2)C1] |
| 118 | 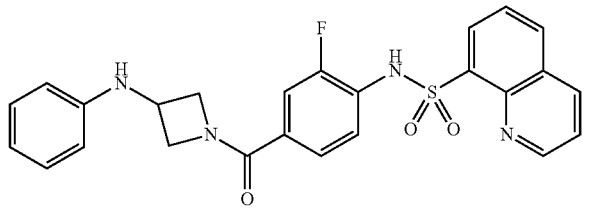 [SMILES: O=C(c1ccc(NS(=O)(=O)c2cccc3cccnc23)c(F)c1)N1CC(Nc2ccccc2)C1] |
| 119 | 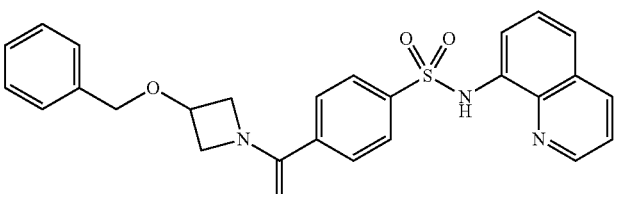 |
| 120 | 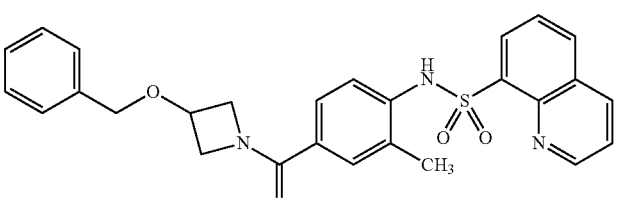 |
| 121 | 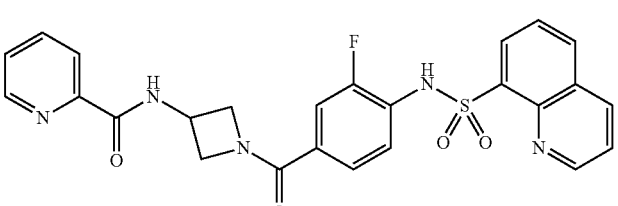 |

| Compound | Structure |
|---|---|
| 122 | 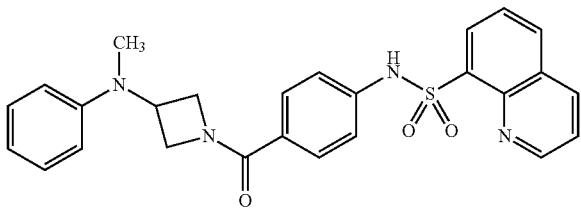 [SMILES: CN(c1ccccc1)C1CN(C(=O)c2ccc(NS(=O)(=O)c3cccc4cccnc34)cc2)C1] |
| 123 | 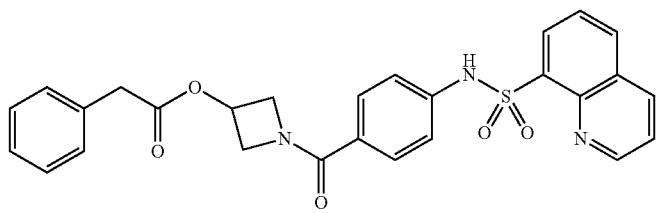 [SMILES: O=C(Cc1ccccc1)OC1CN(C(=O)c2ccc(NS(=O)(=O)c3cccc4cccnc34)cc2)C1] |
| 124 | 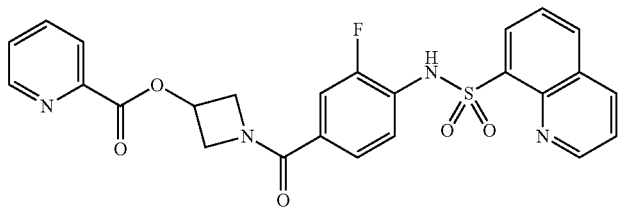 [SMILES: O=C(OC1CN(C(=O)c2ccc(NS(=O)(=O)c3cccc4cccnc34)c(F)c2)C1)c1ccccn1] |
| 125 | 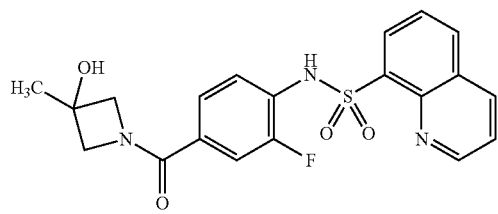 [SMILES: CC1(O)CN(C(=O)c2ccc(NS(=O)(=O)c3cccc4cccnc34)c(F)c2)C1] |
| 126 | 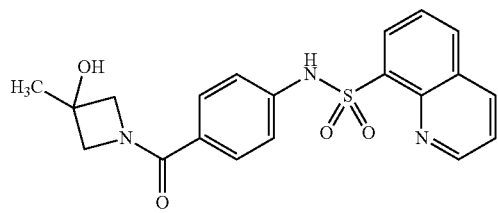 [SMILES: CC1(O)CN(C(=O)c2ccc(NS(=O)(=O)c3cccc4cccnc34)cc2)C1] |
| 127 | 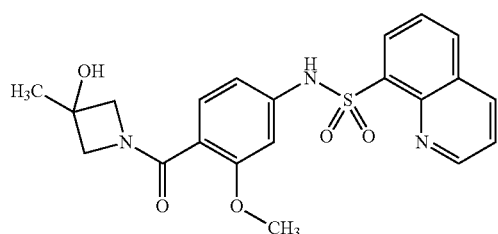 |
| 128 | 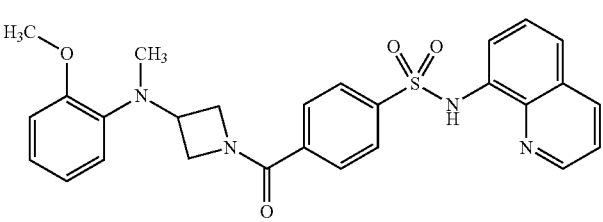 [SMILES: COc1ccccc1N(C)C1CN(C(=O)c2ccc(S(=O)(=O)Nc3cccc4cccnc34)cc2)C1] |

-continued
| Compound | Structure |
|---|---|
| 129 | 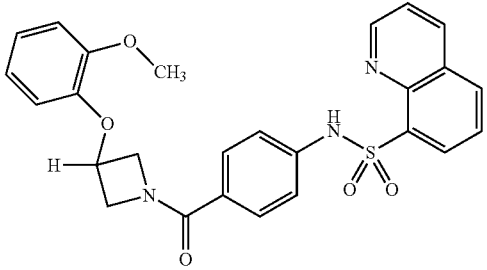 [SMILES: COc1ccccc1OC1CN(C(=O)c2ccc(NS(=O)(=O)c3cccc4cccnc34)cc2)C1] |
| 130 | 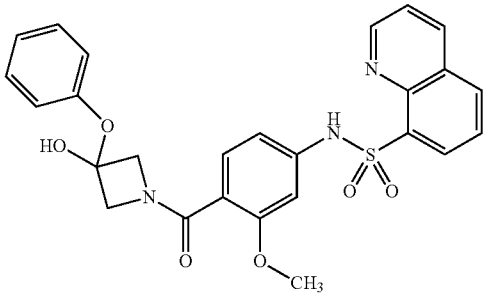 [SMILES: COc1cc(NS(=O)(=O)c2cccc3cccnc23)ccc1C(=O)N1CC(O)(Oc2ccccc2)C1] |
| 131 | 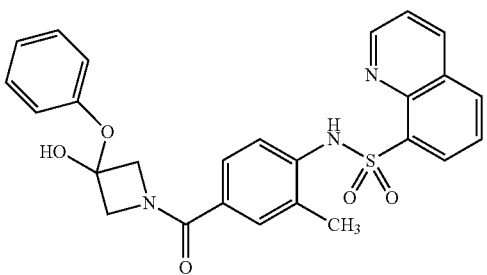 [SMILES: Cc1cc(C(=O)N2CC(O)(Oc3ccccc3)C2)ccc1NS(=O)(=O)c1cccc2cccnc12] |
| 132 | 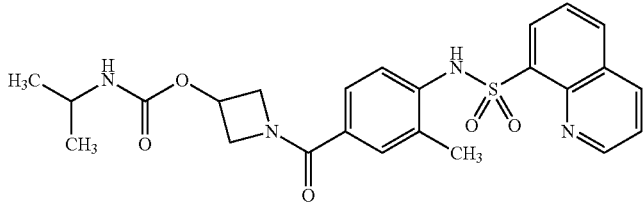 |
| 133 | 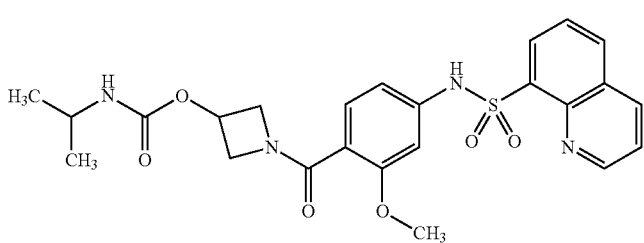 [SMILES: COc1cc(NS(=O)(=O)c2cccc3cccnc23)ccc1C(=O)N1CC(OC(=O)NC(C)C)C1] |
| 134 | 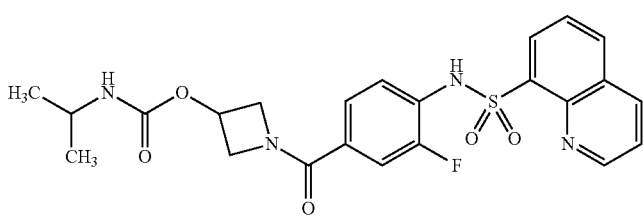 [SMILES: CC(C)NC(=O)OC1CN(C(=O)c2ccc(NS(=O)(=O)c3cccc4cccnc34)c(F)c2)C1] |

-continued

| Compound | Structure |
|---|---|
| 135 | 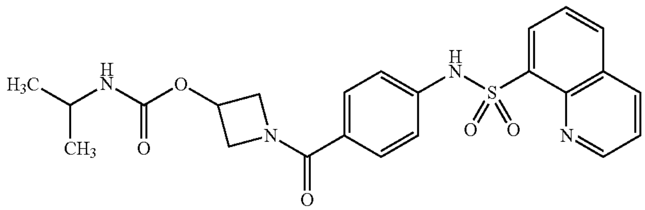 [SMILES: CC(C)NC(=O)OC1CN(C(=O)c2ccc(NS(=O)(=O)c3cccc4cccnc34)cc2)C1] |
| 136 | 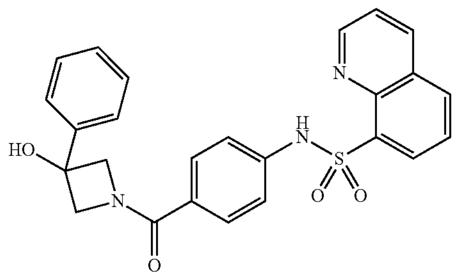 [SMILES: O=C(c1ccc(NS(=O)(=O)c2cccc3cccnc23)cc1)N1CC(O)(c2ccccc2)C1] |
| 137 | 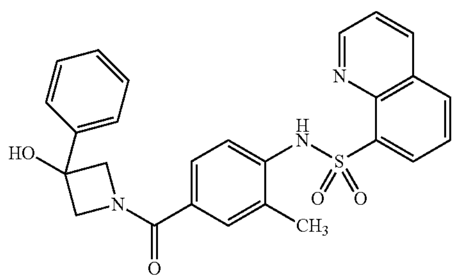 [SMILES: Cc1cc(C(=O)N2CC(O)(c3ccccc3)C2)ccc1NS(=O)(=O)c1cccc2cccnc12] |
| 138 | 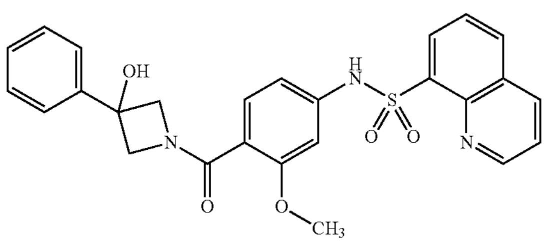 [SMILES: COc1cc(NS(=O)(=O)c2cccc3cccnc23)ccc1C(=O)N1CC(O)(c2ccccc2)C1] |
| 139 | 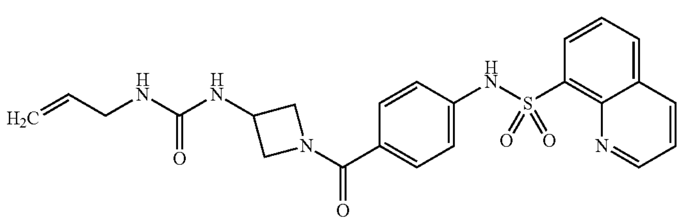 [SMILES: C=CCNC(=O)NC1CN(C(=O)c2ccc(NS(=O)(=O)c3cccc4cccnc34)cc2)C1] |
| 140 | 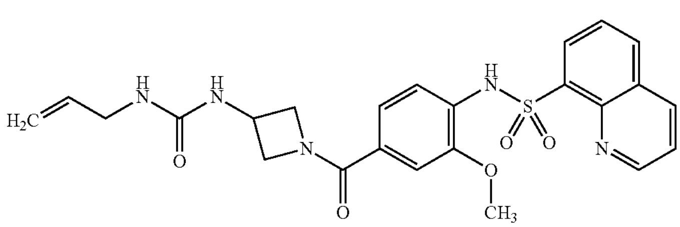 [SMILES: C=CCNC(=O)NC1CN(C(=O)c2ccc(NS(=O)(=O)c3cccc4cccnc34)c(OC)c2)C1] |

-continued
| Compound | Structure |
|---|---|
| 141 | 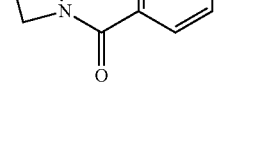 |
| 142 | 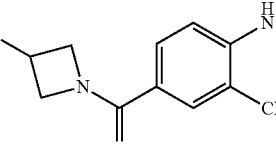 |
| 143 | 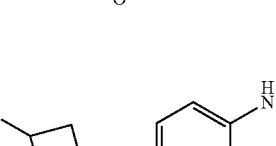 |
| 144 | 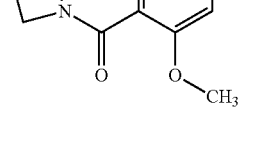 |
| 145 | 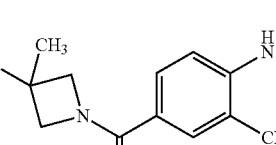 |
| 146 | 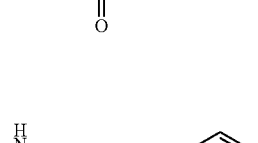 |
| 147 | 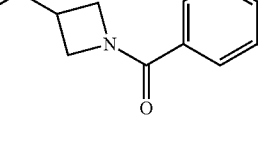 |

-continued

| Compound | Structure |
|---|---|
| 148 | 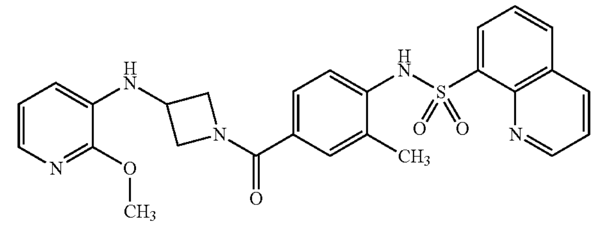 [SMILES: COc1ncccc1NC1CN(C(=O)c2ccc(NS(=O)(=O)c3cccc4cccnc34)c(C)c2)C1] |
| 149 | 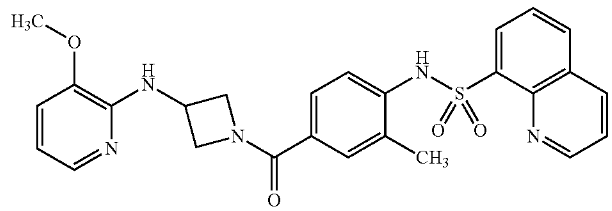 [SMILES: COc1cccnc1NC1CN(C(=O)c2ccc(NS(=O)(=O)c3cccc4cccnc34)c(C)c2)C1] |
| 150 | 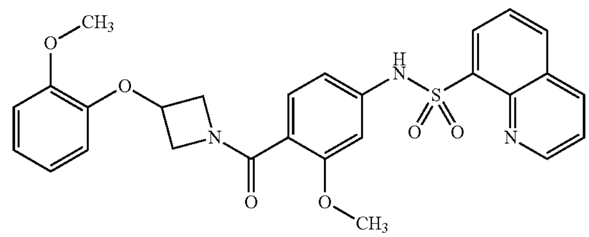 [SMILES: COc1ccccc1OC1CN(C(=O)c2ccc(NS(=O)(=O)c3cccc4cccnc34)cc2OC)C1] |
| 151 | 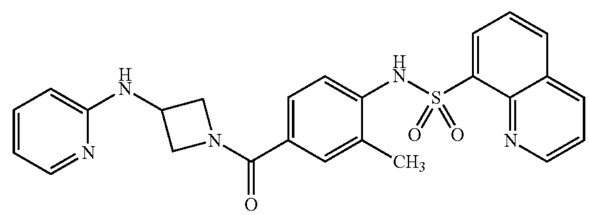 [SMILES: Cc1cc(C(=O)N2CC(Nc3ccccn3)C2)ccc1NS(=O)(=O)c1cccc2cccnc12] |
| 152 | 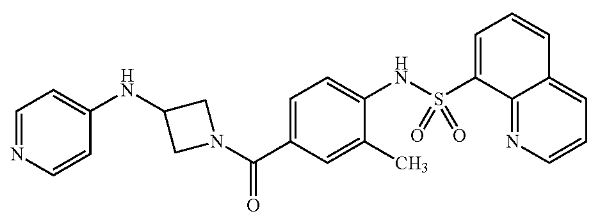 [SMILES: Cc1cc(C(=O)N2CC(Nc3ccncc3)C2)ccc1NS(=O)(=O)c1cccc2cccnc12] |
| 153 | 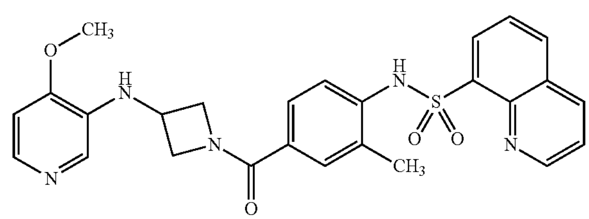 [SMILES: COc1ccncc1NC1CN(C(=O)c2ccc(NS(=O)(=O)c3cccc4cccnc34)c(C)c2)C1] |
| 154 | 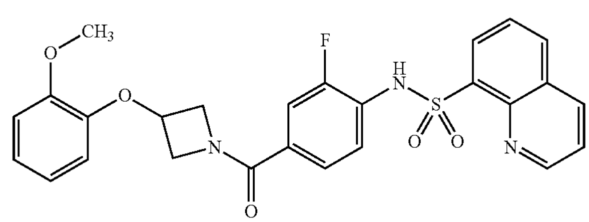 [SMILES: COc1ccccc1OC1CN(C(=O)c2ccc(NS(=O)(=O)c3cccc4cccnc34)c(F)c2)C1] |

| Compound | Structure |
|---|---|
| 155 | 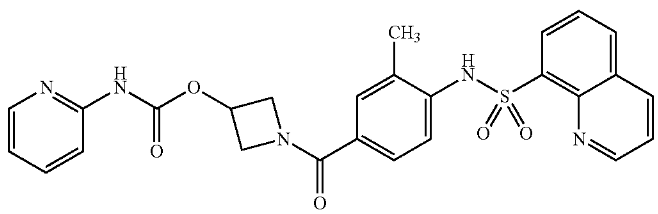 [SMILES: Cc1cc(C(=O)N2CC(OC(=O)Nc3ccccn3)C2)ccc1NS(=O)(=O)c1cccc2cccnc12] |
| 156 | 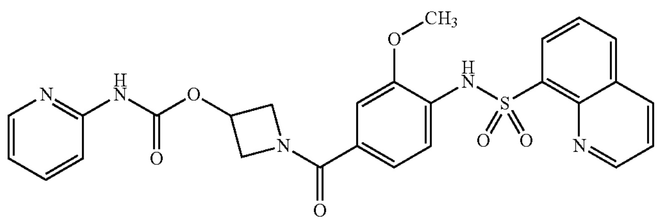 [SMILES: COc1cc(C(=O)N2CC(OC(=O)Nc3ccccn3)C2)ccc1NS(=O)(=O)c1cccc2cccnc12] |
| 157 | 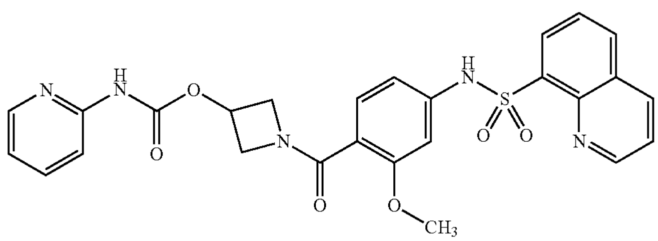 [SMILES: COc1cc(NS(=O)(=O)c2cccc3cccnc23)ccc1C(=O)N1CC(OC(=O)Nc2ccccn2)C1] |
| 158 | 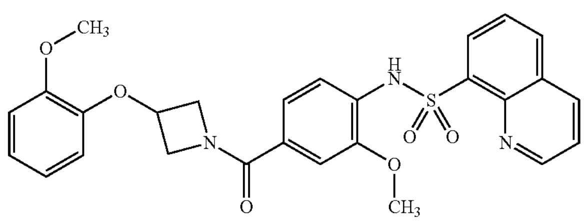 [SMILES: COc1cc(C(=O)N2CC(Oc3ccccc3OC)C2)ccc1NS(=O)(=O)c1cccc2cccnc12] |
| 159 | 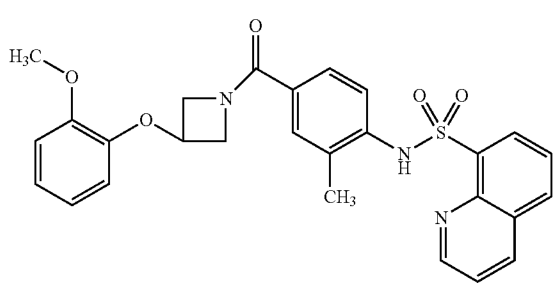 [SMILES: COc1ccccc1OC1CN(C(=O)c2ccc(NS(=O)(=O)c3cccc4cccnc34)c(C)c2)C1] |
| 160 | 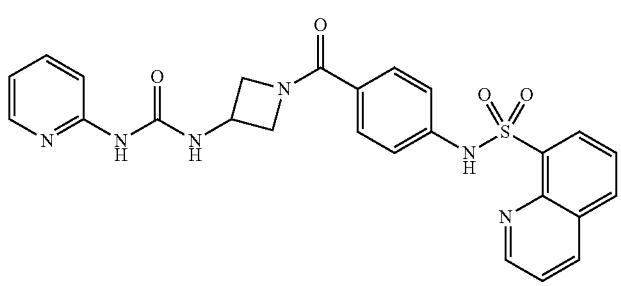 [SMILES: O=C(Nc1ccccn1)NC1CN(C(=O)c2ccc(NS(=O)(=O)c3cccc4cccnc34)cc2)C1] |

| Compound | Structure |
|---|---|
| 161 | 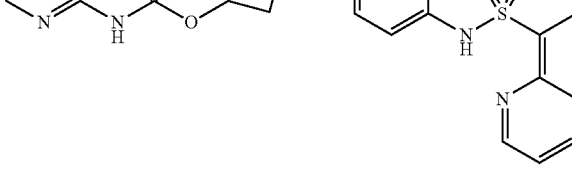 |
| 162 | 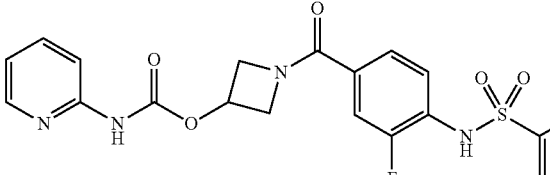 |
| 163 | 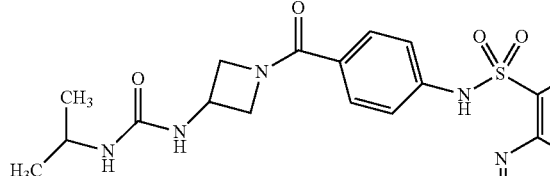 |
| 164 | 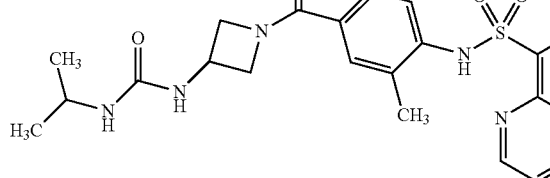 |
| 165 | 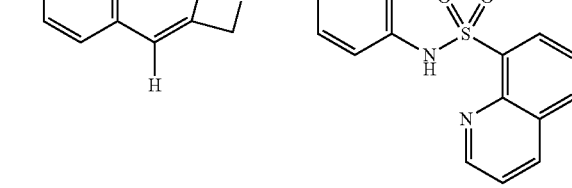 |

| Compound | Structure |
|---|---|
| 166 | 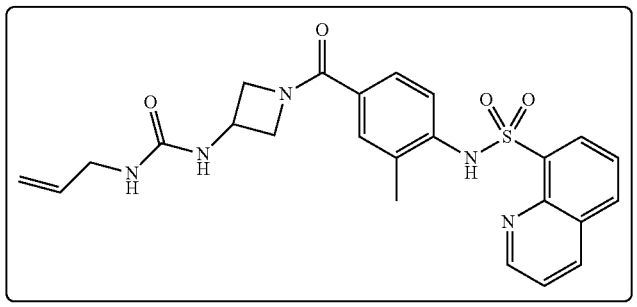 [SMILES: C=CCNC(=O)NC1CN(C(=O)c2ccc(NS(=O)(=O)c3cccc4cccnc34)c(C)c2)C1] |

17. The method of claim 5, wherein the hemolytic anemia is hereditary non-spherocytic hemolytic anemia.

18. A method of treating pyruvate kinase deficiency (PKD) in a subject comprising administering to a subject in need thereof a therapeutically effective amount of (1) a compound of formula I or a pharmaceutically acceptable salt thereof; or (2) a pharmaceutically acceptable composition comprising a compound of formula I or a pharmaceutically acceptable salt thereof, and a pharmaceutically acceptable carrier, wherein:

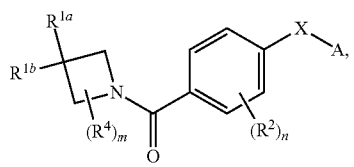 (I)

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

$R^{1a}$ is selected from hydrogen, alkyl, and arylalkyl; and $R^{1b}$ is selected from OR$^3$, N(alkyl)R$^3$ and NHR$^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted;

each $R^4$ is independently selected from haloalkyl, alkyl, alkoxy and hydroxyl;

n is 0, 1, or 2; and m is 0, 1, or 2.

19. A method for activating PKR in red blood cells comprising (1) a compound of formula I or a pharmaceutically acceptable salt thereof; or (2) a pharmaceutical composition comprising a compound of formula I or a pharmaceutically acceptable salt thereof, and a pharmaceutically acceptable carrier, wherein:

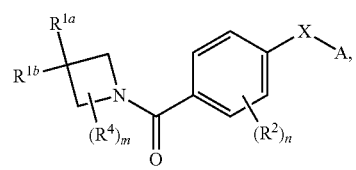 (I)

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

$R^{1a}$ is selected from hydrogen, alkyl, and arylalkyl; and $R^{1b}$ is selected from OR$^3$, N(alkyl)R$^3$ and NHR$^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted;

each $R^4$ is independently selected from haloalkyl, alkyl, alkoxy and hydroxyl;

n is 0, 1, or 2; and m is 0, 1, or 2.

20. A method for treating thalassemia; hereditary spherocytosis; hereditary elliptocytosis; abetalipoproteinemia; Bassen-Kornzweig syndrome; paroxysmal nocturnal hemoglobinuria; acquired hemolytic anemia; or anemia of chronic diseases comprising (1) a compound of formula I or a pharmaceutically acceptable salt thereof; or (2) a pharmaceutical composition comprising a compound of formula I or a pharmaceutically acceptable salt thereof, and a pharmaceutically acceptable carrier; wherein:

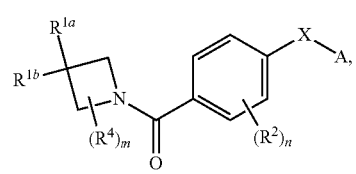 (I)

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

$R^{1a}$ is selected from hydrogen, alkyl, and arylalkyl; and $R^{1b}$ is selected from $OR^3$, N(alkyl)$R^3$ and $NHR^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, C(O)$R^a$, and C(O)N(H)$R^a$, wherein $R^a$ is selected from alkyl, alkenyl, aryl, heteroaryl, arylalkyl and heteroarylalkyl; and wherein any aryl or heteroaryl portion of $R^a$ is optionally substituted;

each $R^4$ is independently selected from haloalkyl, alkyl, alkoxy and hydroxyl;

n is 0, 1, or 2; and m is 0, 1, or 2.

21. The method of claim 1, wherein the compounds has the structure:

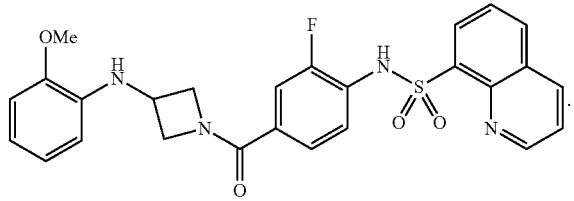 [SMILES: COc1ccccc1NC1CN(C(=O)c2ccc(NS(=O)(=O)c3cccc4cccnc34)c(F)c2)C1]

22. The method of claim 1, wherein the compounds has the structure:

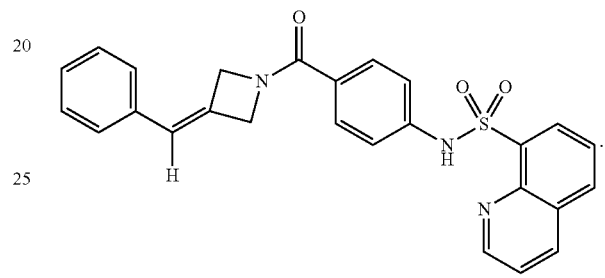

23. The method of claim 1, wherein the compounds has the structure:

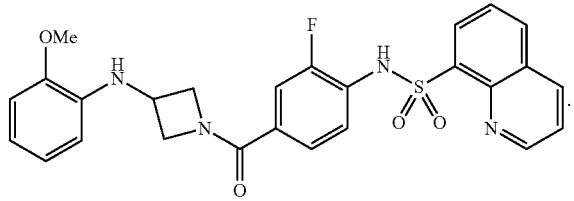 [SMILES: COc1ccccc1NC1CN(C(=O)c2ccc(NS(=O)(=O)c3cccc4cccnc34)c(F)c2)C1]

24. The method of claim 1, wherein the compounds has the structure:

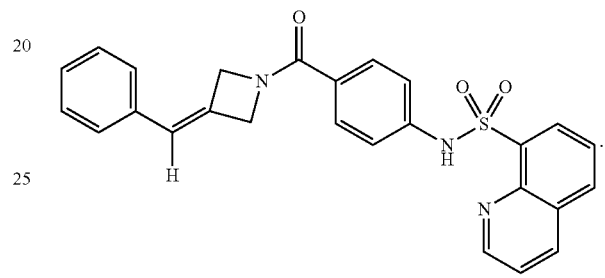

25. The method of claim 1, wherein the compounds has the structure:

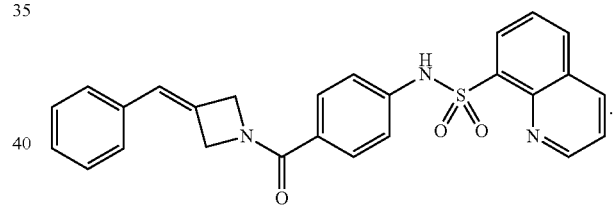

* * * * *